(12) United States Patent
Muzyczka et al.

(10) Patent No.: US 11,000,597 B2
(45) Date of Patent: May 11, 2021

(54) ENGINEERED RECEPTOR/LIGAND SYSTEM FOR DELIVERY OF THERAPEUTIC AGENTS

(71) Applicant: University of Florida Research Foundation, Incorporated, Gainesville, FL (US)

(72) Inventors: Nicholas Muzyczka, Gainesville, FL (US); Hector Ruben Mendez-Gomez, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 776 days.

(21) Appl. No.: 15/544,906

(22) PCT Filed: Jan. 21, 2016

(86) PCT No.: PCT/US2016/014398
§ 371 (c)(1),
(2) Date: Jul. 20, 2017

(87) PCT Pub. No.: WO2016/118787
PCT Pub. Date: Jul. 28, 2016

(65) Prior Publication Data
US 2018/0015172 A1 Jan. 18, 2018

Related U.S. Application Data

(60) Provisional application No. 62/105,951, filed on Jan. 21, 2015.

(51) Int. Cl.
*A61K 48/00* (2006.01)
*A61K 9/00* (2006.01)
*A61K 38/17* (2006.01)
*A61K 38/16* (2006.01)
*A61K 49/00* (2006.01)
*C12N 7/00* (2006.01)
*A61K 47/64* (2017.01)
*A61K 47/69* (2017.01)

(52) U.S. Cl.
CPC ............ *A61K 47/64* (2017.08); *A61K 9/0019* (2013.01); *A61K 38/164* (2013.01); *A61K 38/177* (2013.01); *A61K 47/6929* (2017.08); *A61K 48/0008* (2013.01); *A61K 48/0058* (2013.01); *A61K 49/0002* (2013.01); *C12N 7/00* (2013.01); *C12N 2750/14143* (2013.01)

(58) Field of Classification Search
CPC ................ A61K 47/64; A61K 48/0058; A61K 49/0002; A61K 47/6929; A61K 38/177; A61K 9/0019; C12N 7/00
See application file for complete search history.

(56) References Cited

U.S. PATENT DOCUMENTS

| | | | |
|---|---|---|---|
| 2005/0106700 A1 | 5/2005 | Nomura et al. |
| 2006/0127358 A1 | 6/2006 | Muzyczka et al. |
| 2007/0196275 A1 | 8/2007 | Li et al. |
| 2009/0286321 A1 | 11/2009 | Warrington et al. |
| 2014/0134168 A1 | 5/2014 | Zurawski et al. |
| 2014/0227268 A1 | 8/2014 | Banchereau et al. |

OTHER PUBLICATIONS

International Search Report and Written Opinion dated Apr. 1, 2016 for Application No. PCT/US2016/014398.
International Preliminary Report on Patentability dated Aug. 3, 2017 for Application No. PCT/US2016/014398.
Méndez-Gómez et al., Transcytosis in the blood-cerebrospinal fluid barrier of the mouse brain with an engineered receptor/ligand system. Mol Ther Methods Clin Dev. Oct. 7, 2015;2:15037. doi: 10.1038/mtm.2015.37. eCollection 2015.

*Primary Examiner* — Antonio Galisteo Gonzalez
(74) *Attorney, Agent, or Firm* — Wolf, Greenfield & Sacks, P.C.

(57) ABSTRACT

Provided herein are compositions and methods related to targeted delivery of a therapeutic or diagnostic agent to a subject utilizing an engineered receptor-ligand system, such as an engineered dockerin-cohesin system. As described herein, previously-developed targeted delivery systems for delivering therapeutic and diagnostic agents to a tissue of interest have drawbacks that have not been addressed to date. For example, with respect to the blood-brain barrier (BBB) and the blood-cerebrospinal fluid barrier (BCSFB), both of which hamper delivery of agents to the brain, others have relied on the use of endogenously expressed receptors, like the transferrin receptor, to assist the agent across the barriers.

20 Claims, 7 Drawing Sheets
Specification includes a Sequence Listing.

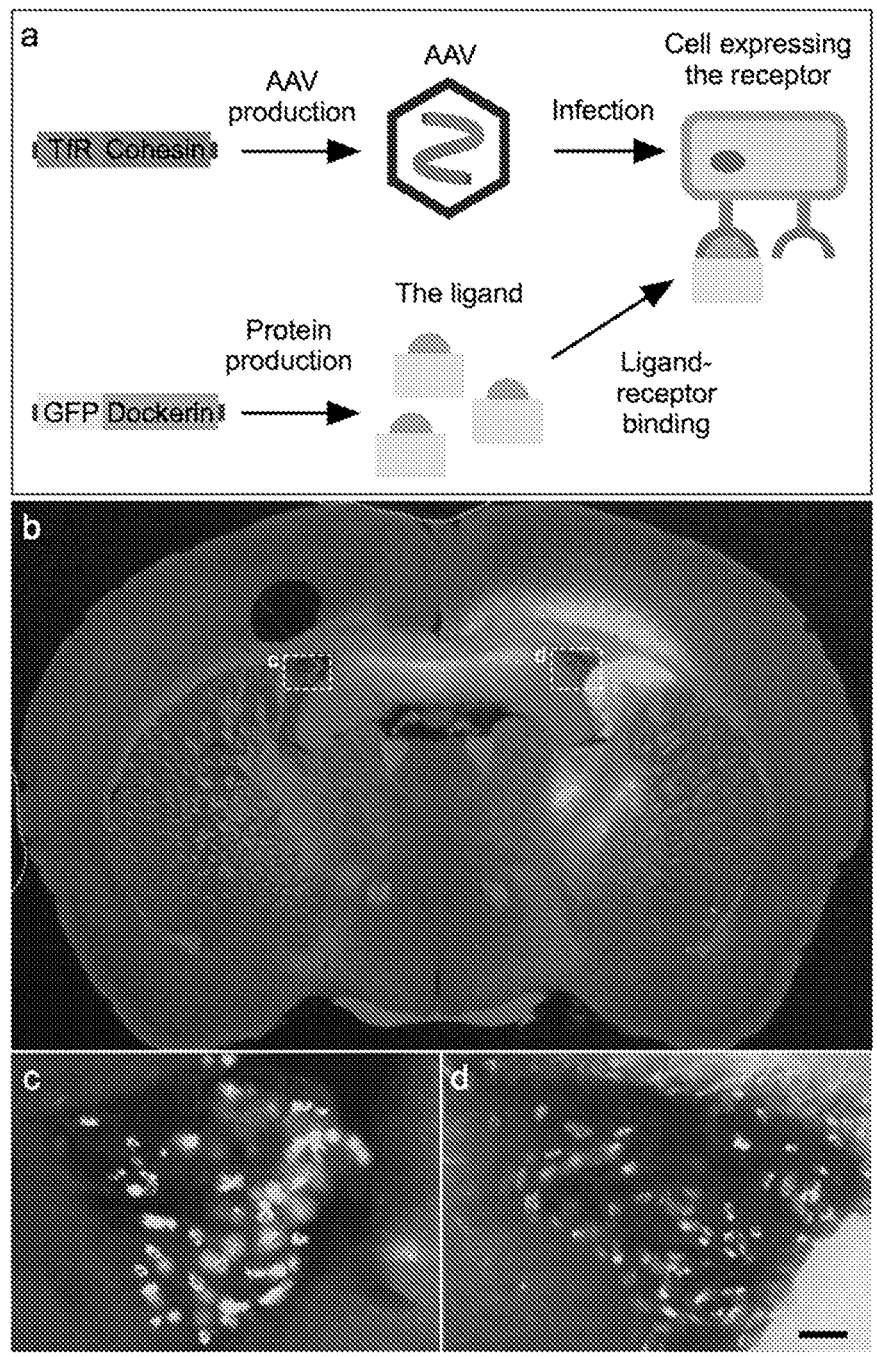
FIGS. 1A-D

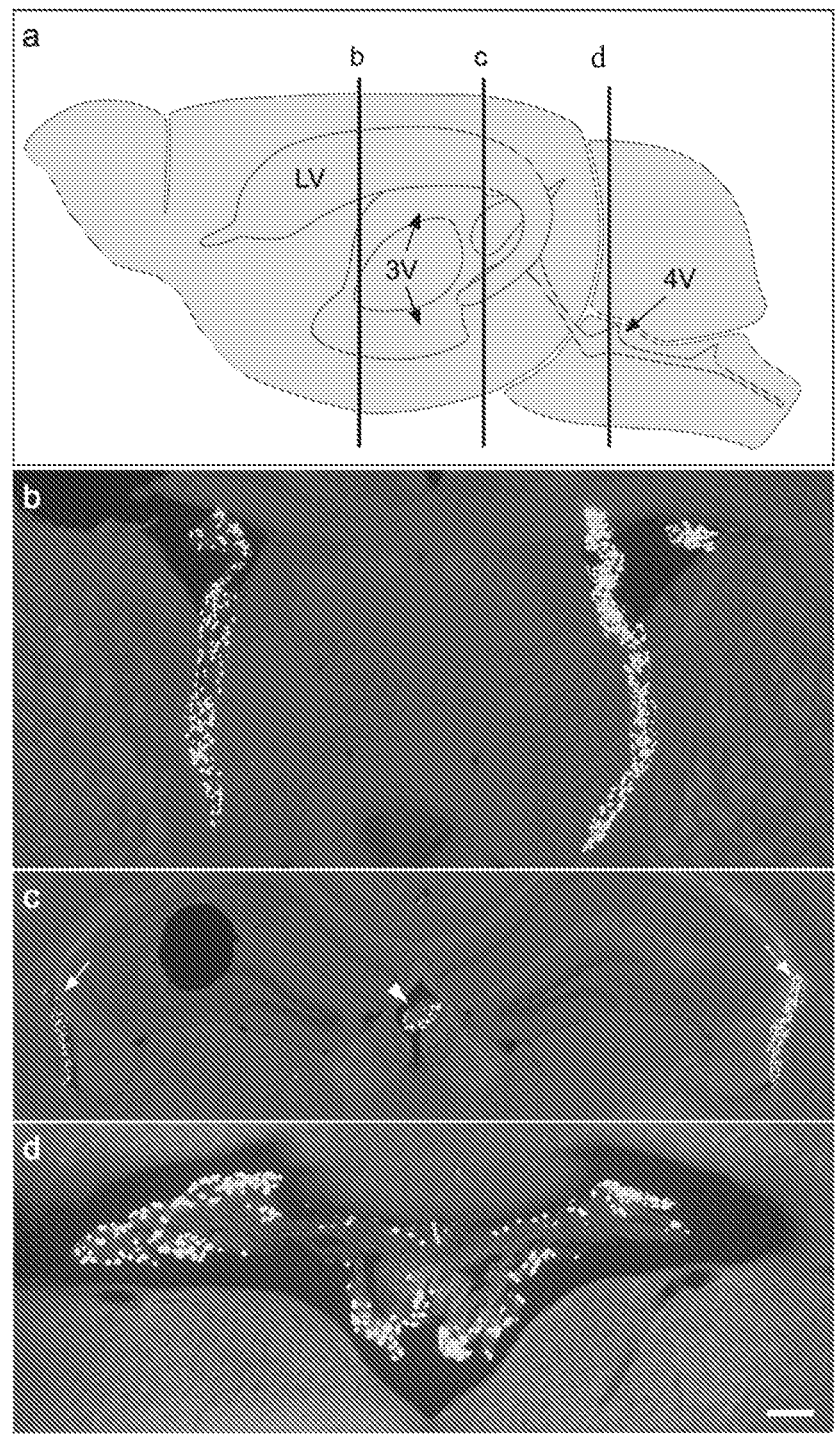
FIGS. 2A-D

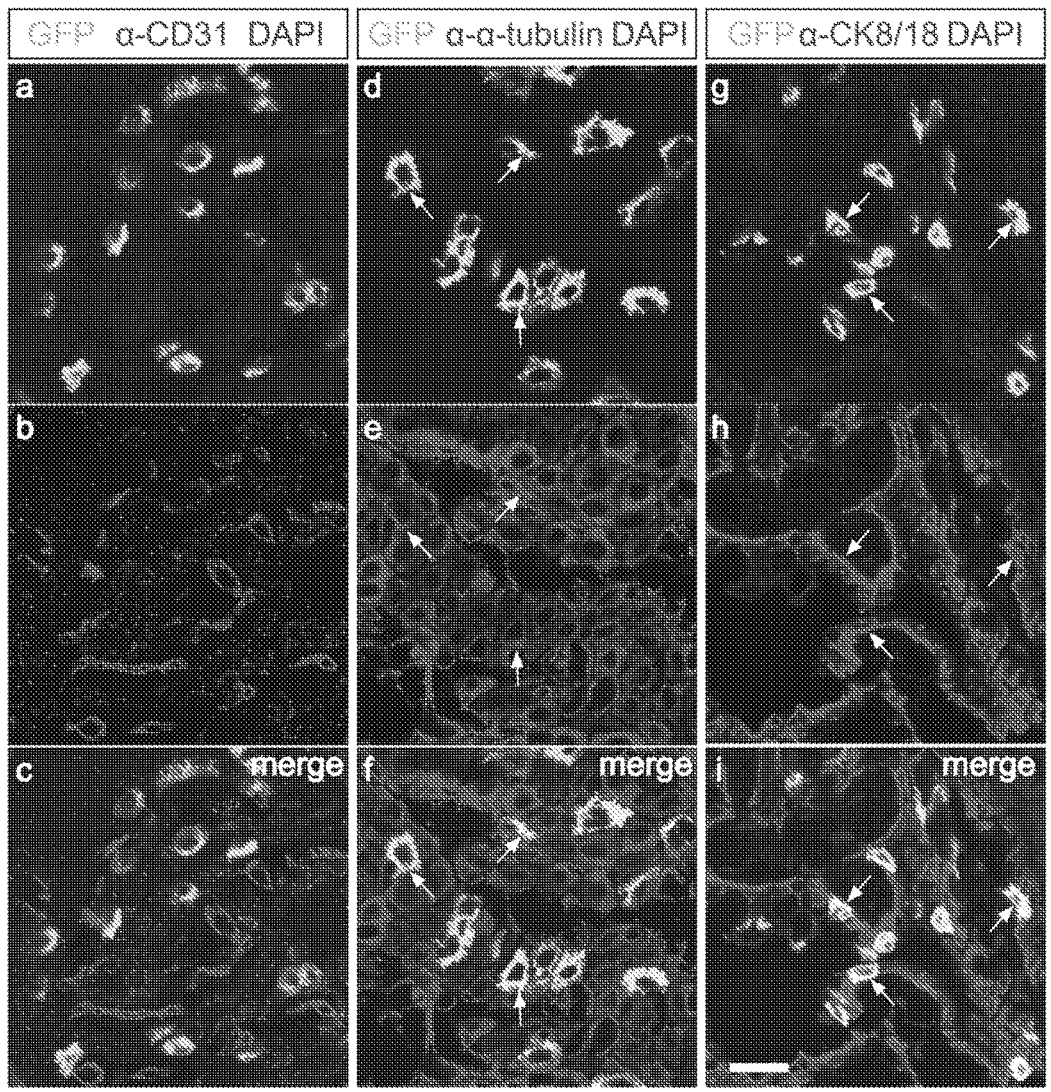
FIGS. 3A-I

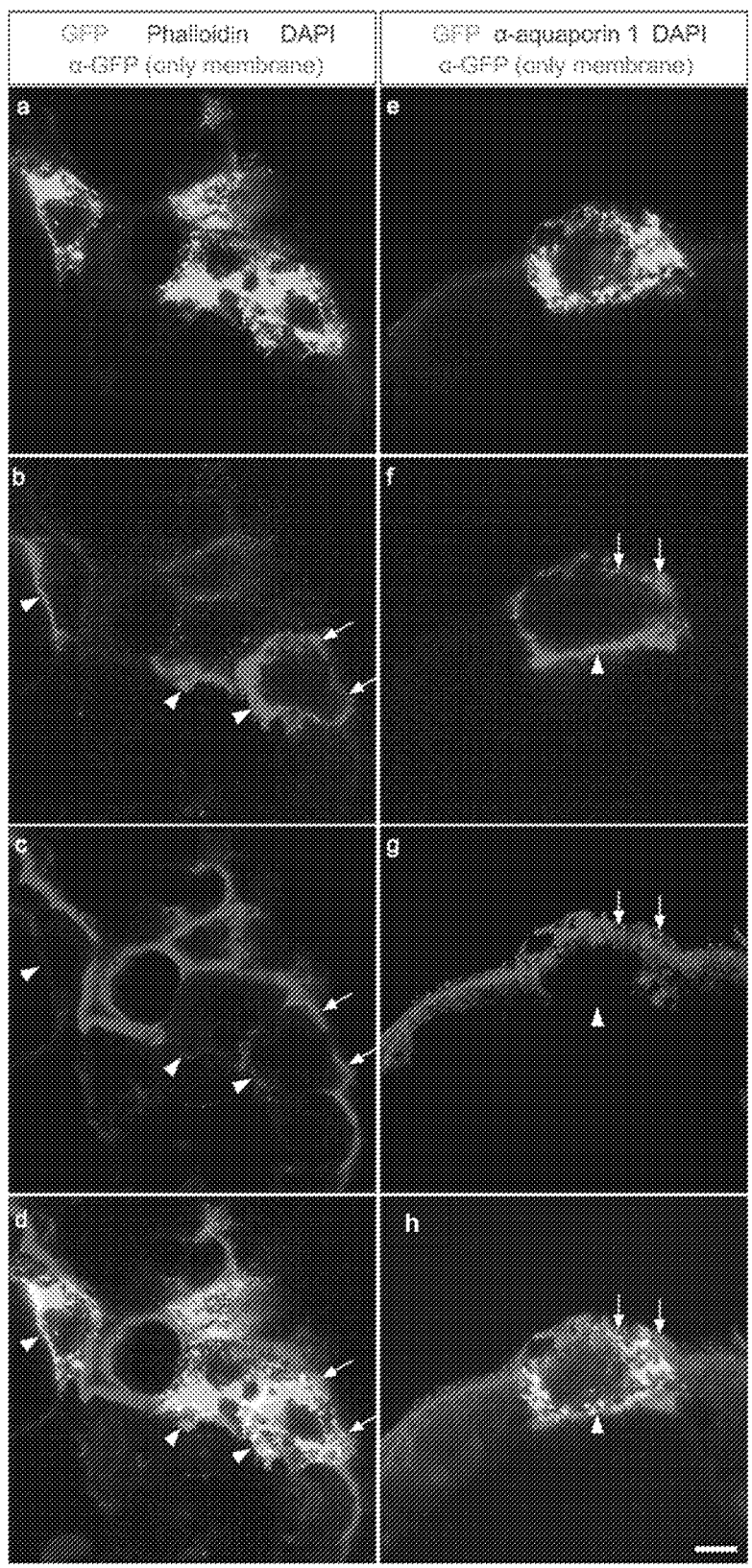
FIGS. 4A-H

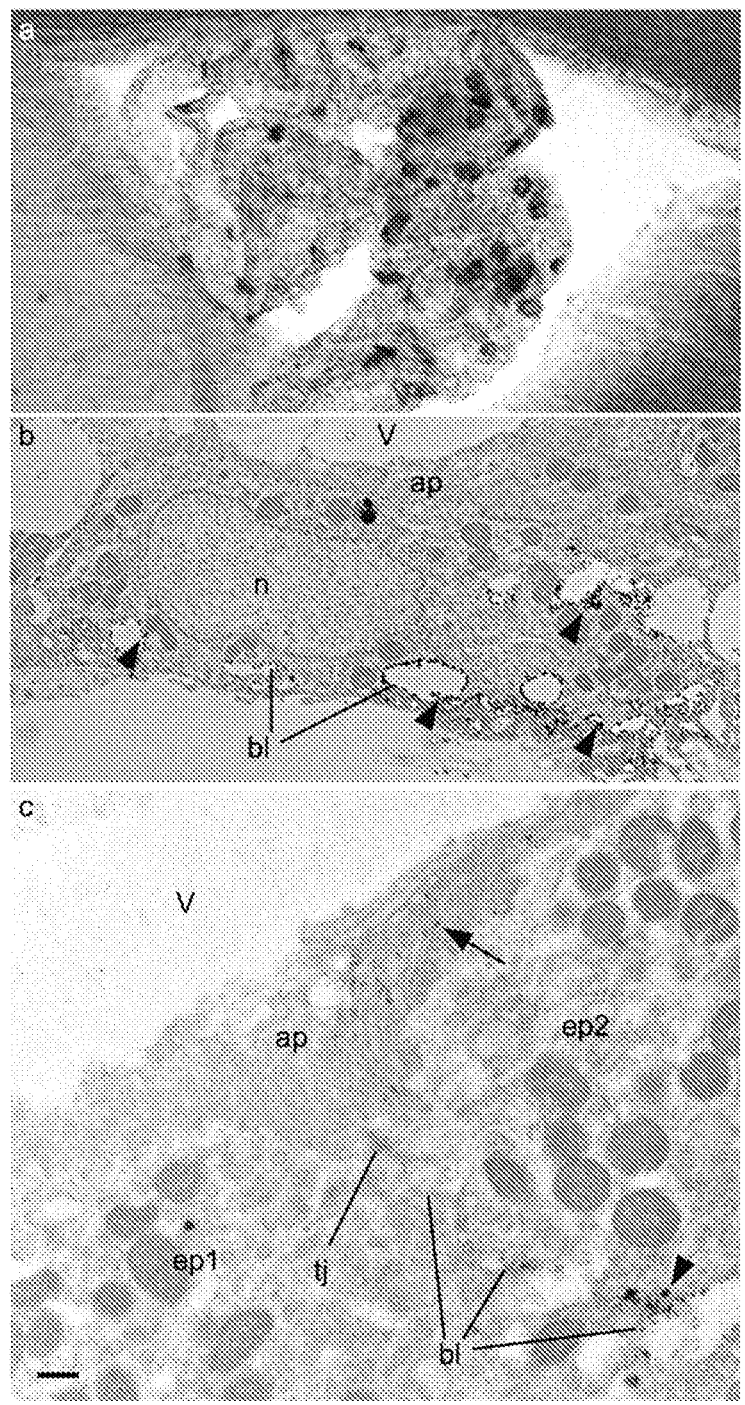
FIGS. 5A-C

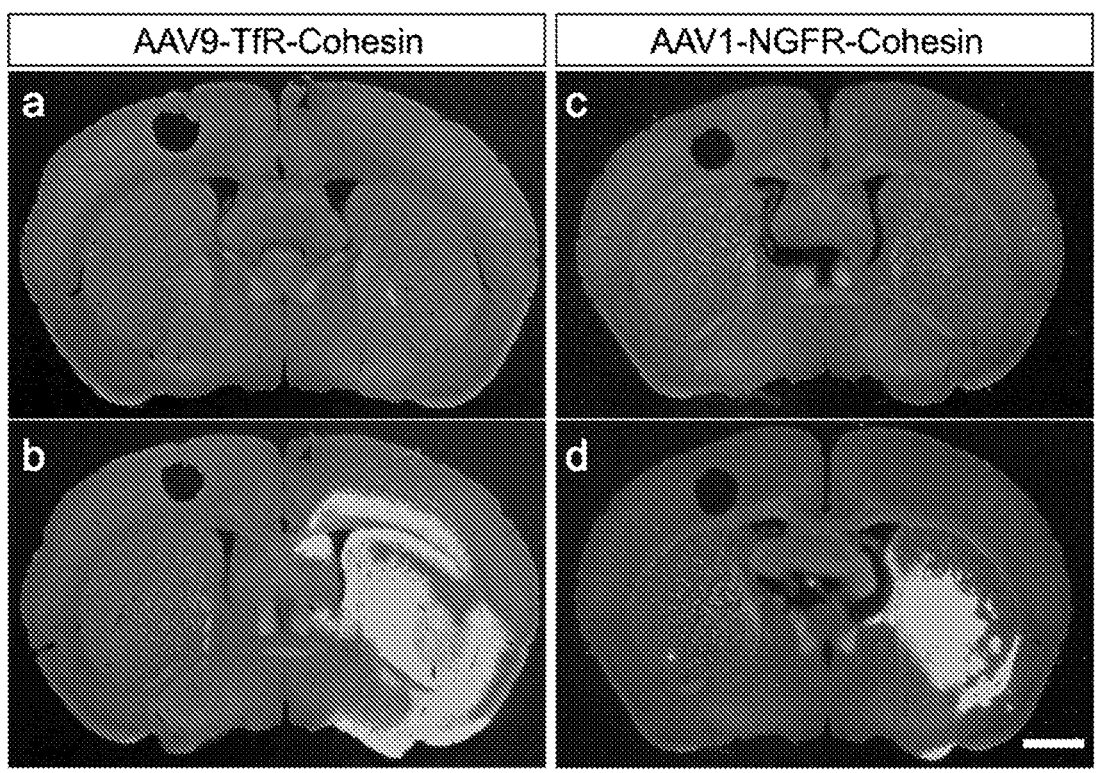
FIGS. 6A-D

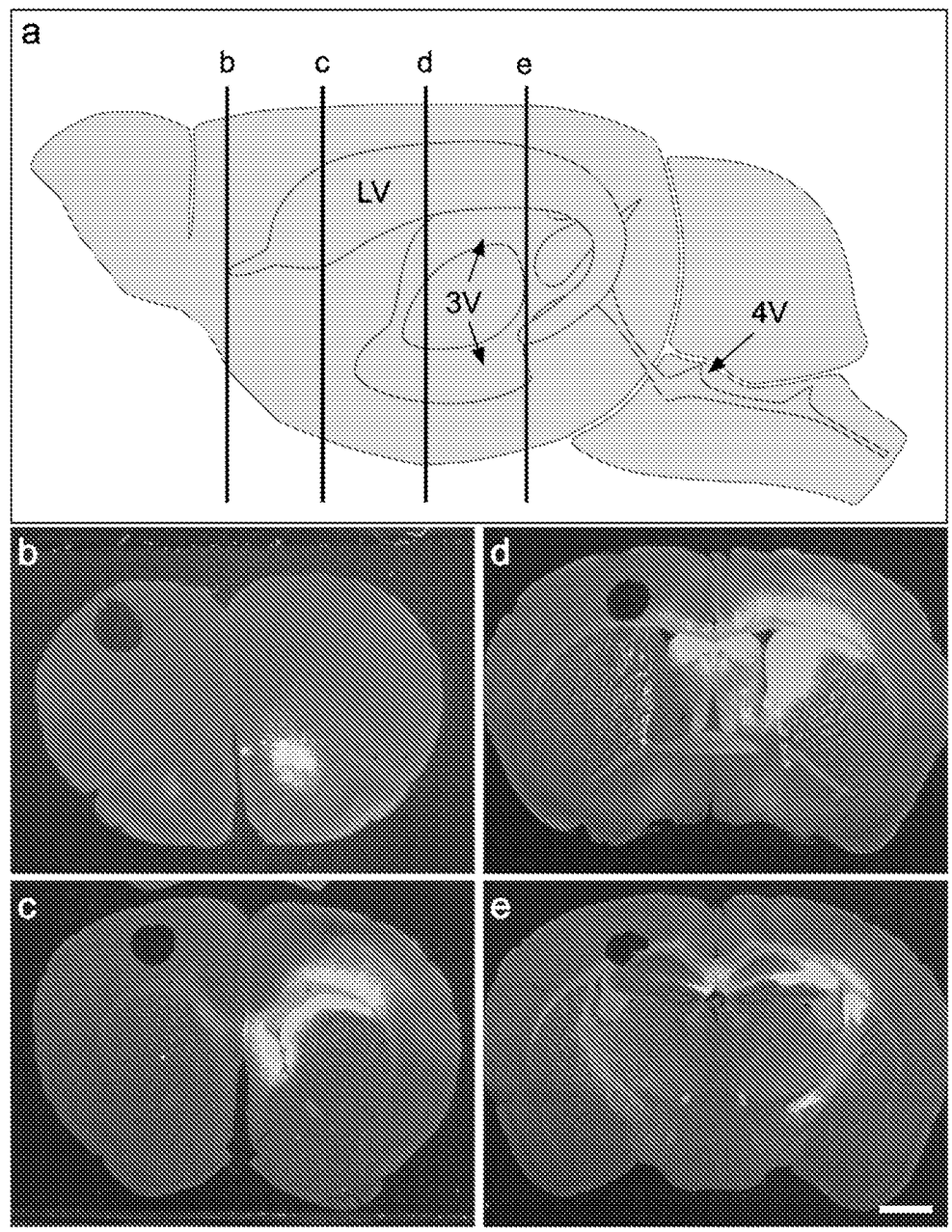
FIGS. 7A-E

SEQUENCE LISTING

<160> NUMBER OF SEQ ID NOS: 24

<210> SEQ ID NO 1
<211> LENGTH: 143
<212> TYPE: PRT
<213> ORGANISM: Artificial Sequence
<220> FEATURE:
<223> OTHER INFORMATION: Synthetic Polypeptide

<400> SEQUENCE: 1

```
Ala Val Arg Ile Lys Val Asp Thr Val Asn Ala Lys Pro Gly Asp Thr
1               5                   10                  15

Val Arg Ile Pro Val Arg Phe Ser Gly Ile Pro Ser Lys Gly Ile Ala
                20                  25                  30

Asn Cys Asp Phe Val Tyr Ser Tyr Asp Pro Asn Val Leu Glu Ile Ile
            35                  40                  45

Glu Ile Glu Pro Gly Glu Leu Ile Val Asp Pro Asn Pro Thr Lys Ser
        50                  55                  60

Phe Asp Thr Ala Val Tyr Pro Asp Arg Lys Met Ile Val Phe Leu Phe
65                  70                  75                  80

Ala Glu Asp Ser Gly Thr Gly Ala Tyr Ala Ile Thr Glu Asp Gly Val
                85                  90                  95

Phe Ala Thr Ile Val Ala Lys Val Lys Ser Gly Ala Pro Asn Gly Leu
            100                 105                 110

Ser Val Ile Lys Phe Val Glu Val Gly Gly Phe Ala Asn Asn Asp Leu
        115                 120                 125

Val Glu Gln Lys Thr Gln Phe Phe Asp Gly Gly Val Asn Val Gly
    130                 135                 140
```

<210> SEQ ID NO 2
<211> LENGTH: 2280
<212> TYPE: DNA
<213> ORGANISM: Artificial Sequence
<220> FEATURE:
<223> OTHER INFORMATION: Synthetic Polynucleotide

<400> SEQUENCE: 2

```
atgatggatc aagctagatc agcattctct aacttgtttg gtggagaacc attgtcatat      60
acccggttca gcctggctcg gcaagtagat ggcgataaca gtcatgtgga gatgaaactt     120
gctgtagatg aagaagaaaa tgctgacaat aacacaaagg ccaatgtcac aaaaccaaaa     180
aggtgtagtg aagtatctg ctatgggact attgctgtga tcgtcttttt cttgattgga      240
tttatgattg gctacttggg ctattgtaaa ggggtagaac caaaaactga gtgtgagaga     300
ctggcaggaa ccgagtctcc agtgagggag gagccaggag aggacttccc tgcagcacgt     360
cgcttatatt gggatgacct gaagagaaag ttgtcggaga aactggacag cacagacttc     420
accagcacca tcaagctgct gaatgaaaat tcatatgtcc ctcgtgaggc tggatctcaa     480
aaagatgaaa tcttgcgtt gtatgttgaa atcaatttc gtgaatttaa actcagcaaa      540
gtctggcgtg atcaacattt tgttaagatt caggtcaaag acagcgctca aaactcggtg     600
atcatagttg ataagaacgg tagacttgtt tacctggtgg agaatcctgg gggttatgtg     660
gcgtatagta aggctgcaac agttactggt aaactggtcc atgctaattt tggtactaaa     720
aaagattttg aggatttata cactcctgtg aatggatcta tagtgattgt cagagcaggg     780
aaaatcacct ttgcagaaaa ggttgcaaat gctgaaagct aaatgcaat tggtgtgttg      840 atatacatgg accagactaa atttcccatt gttaacgcag aactttcatt ctttggacat     900
```

| | |
|---|---|
| gctcatctgg ggacaggtga cccttacaca cctggattcc cttccttcaa tcacactcag | 960 |
| tttccaccat ctcggtcatc aggattgcct aatatacctg tccagacaat ctccagagct | 1020 |
| gctgcagaaa agctgtttgg gaatatggaa ggagactgtc cctctgactg gaaaacagac | 1080 |
| tctacatgta ggatggtaac ctcagaaagc aagaatgtga agctcactgt gagcaatgtg | 1140 |
| ctgaaagaga taaaaattct taacatcttt ggagttatta aaggctttgt agaaccagat | 1200 |
| cactatgttg tagttggggc ccagagagat gcatggggcc ctggagctgc aaaatccggt | 1260 |
| gtaggcacag ctctcctatt gaaacttgcc cagatgttct cagatatggt cttaaaagat | 1320 |
| gggtttcagc ccagcagaag cattatcttt gccagttgga gtgctggaga ctttggatcg | 1380 |
| gttggtgcca ctgaatggct agagggatac ctttcgtccc tgcatttaaa ggctttcact | 1440 |
| tatattaatc tggataaagc ggttcttggt accagcaact tcaaggtttc tgccagccca | 1500 |
| ctgttgtata cgcttattga gaaaacaatg caaaatgtga agcatccggt tactgggcaa | 1560 |
| tttctatatc aggacagcaa ctgggccagc aaagttgaga aactcacttt agacaatgct | 1620 |
| gctttcccct tccttgcata ttctggaatc ccagcagttt ctttctgttt ttgcgaggac | 1680 |
| acagattatc cttatttggg taccaccatg gacacctata aggaactgat tgagaggatt | 1740 |
| cctgagttga caaagtggc acgagcagct gcagaggtcg ctggtcagtt cgtgattaaa | 1800 |
| ctaacccatg atgttgaatt gaacctggac tatgagaggt acaacagcca actgctttca | 1860 |
| tttgtgaggg atctgaacca atacagagca gacataaagg aaatgggcct gagtttacag | 1920 |
| tggctgtatt ctgctcgtgg agacttcttc cgtgctactt ccagactaac aacagatttc | 1980 |
| gggaatgctg agaaaacaga cagatttgtc atgaagaaac tcaatgatcg tgtcatgaga | 2040 |
| gtggagtatc acttcctctc tccctacgta tctccaaaag agtctccttt ccgacatgtc | 2100 |
| ttctggggct ccggctctca cacgctgcca gctttactgg agaacttgaa actgcgtaaa | 2160 |
| caaaataacg gtgcttttaa tgaaacgctg ttcagaaacc agttggctct agctacttgg | 2220 |
| actattcagg gagctgcaaa tgccctctct ggtgacgttt gggacattga caatgagttt | 2280 |

<210> SEQ ID NO 3
<211> LENGTH: 957
<212> TYPE: DNA
<213> ORGANISM: Artificial Sequence
<220> FEATURE:
<223> OTHER INFORMATION: Synthetic Polynucleotide

<400> SEQUENCE: 3

| | |
|---|---|
| atggggggcag gtgccaccgg ccgcgccatg gacgggccgc gcctgctgct gttgctgctt | 60 |
| ctgggggtgt cccttggagg tgccactcga gtaggaattc caaggaggc atgccccaca | 120 |
| ggcctgtaca cacacagcgg tgagtgctgc aaagcctgca acctgggcga gggtgtggcc | 180 |
| cagccttgtg gagccaacca gaccgtgtgt gagccctgcc tggacagcgt gacgttctcc | 240 |
| gacgtggtga cgcgaccga gccgtgcaag ccgtgcaccg agtgcgtggg gctccagagc | 300 |
| atgtcggcgc cgtgcgtgga ggccgacgac gccgtgtgcc gctgcgccta cggctactac | 360 |
| caggatgaga cgactgggcg ctgcgaggcg tgccgcgtgt gcgaggcggg ctcgggcctc | 420 |
| gtgttctcct gccaggacaa gcagaacacc gtgtgcgagg agtgccccga cggcacgtat | 480 |
| tccgacgagg ccaaccacgt ggacccgtgc ctgccctgca ccgtgtgcga ggacaccgag | 540 |
| cgccagctcc gcgagtgcac acgctgggcc gacgccgagt gcgaggagat ccctggccgt | 600 |
| tggattacac ggtccacacc cccagagggc tcggacagca cagcccccag cacccaggag | 660 |
| cctgaggcac ctccagaaca agacctcata gccagcacgg tggcaggtgt ggtgaccaca | 720 |

```
gtgatgggca gctcccagcc cgtggtgacc cgaggcacca ccgacaacct catccctgtc    780
tattgctcca tcctggctgc tgtggttgtg ggccttgtgg cctacatagc cttcaagagg    840
tggaacagga gacacaaaca gaaaattgtg gcaccggtga aacagacttt gaattttgac    900
cttctcaagt tggcgggaga cgtcgagtcc aaccctgggc cggcgacac atcgatc       957
```

<210> SEQ ID NO 4
<211> LENGTH: 923
<212> TYPE: PRT
<213> ORGANISM: Artificial Sequence
<220> FEATURE:
<223> OTHER INFORMATION: Synthetic Polypeptide

<400> SEQUENCE: 4

```
Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
 50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
        115                 120                 125

Arg Lys Leu Ser Glu Lys Leu Asp Ser Thr Asp Phe Thr Ser Thr Ile
130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
    210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
    290                 295                 300

Thr Gly Asp Pro Tyr Thr Pro Gly Phe Pro Ser Phe Asn His Thr Gln
305                 310                 315                 320
```

```
Phe Pro Pro Ser Arg Ser Ser Gly Leu Pro Asn Ile Pro Val Gln Thr
            325                 330                 335

Ile Ser Arg Ala Ala Glu Lys Leu Phe Gly Asn Met Glu Gly Asp
        340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Lys Leu Ala Gln Met
            420                 425                 430

Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
    450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
```

```
              740                 745                 750
Val Trp Asp Ile Asp Asn Glu Phe Ser Glu Phe Gly Ser Thr Gly Ser
            755                 760                 765

Thr Gly Ser Thr Gly Ala Asp Pro Thr Arg Ala Ala Val Arg Ile Lys
        770                 775                 780

Val Asp Thr Val Asn Ala Lys Pro Gly Asp Thr Val Arg Ile Pro Val
785                 790                 795                 800

Arg Phe Ser Gly Ile Pro Ser Lys Gly Ile Ala Asn Cys Asp Phe Val
                805                 810                 815

Tyr Ser Tyr Asp Pro Asn Val Leu Glu Ile Ile Glu Ile Glu Pro Gly
            820                 825                 830

Glu Leu Ile Val Asp Pro Asn Pro Thr Lys Ser Phe Asp Thr Ala Val
        835                 840                 845

Tyr Pro Asp Arg Lys Met Ile Val Phe Leu Phe Ala Glu Asp Ser Gly
    850                 855                 860

Thr Gly Ala Tyr Ala Ile Thr Glu Asp Gly Val Phe Ala Thr Ile Val
865                 870                 875                 880

Ala Lys Val Lys Ser Gly Ala Pro Asn Gly Leu Ser Val Ile Lys Phe
                885                 890                 895

Val Glu Val Gly Gly Phe Ala Asn Asn Asp Leu Val Glu Gln Lys Thr
            900                 905                 910

Gln Phe Phe Asp Gly Gly Val Asn Val Gly Thr
        915                 920

<210> SEQ ID NO 5
<211> LENGTH: 465
<212> TYPE: PRT
<213> ORGANISM: Artificial Sequence
<220> FEATURE:
<223> OTHER INFORMATION: Synthetic Polypeptide

<400> SEQUENCE: 5

Met Gly Ala Gly Ala Thr Gly Arg Ala Met Asp Gly Pro Arg Leu Leu
1               5                  10                  15

Leu Leu Leu Leu Leu Gly Val Ser Leu Gly Gly Ala Thr Arg Ala Ala
            20                  25                  30

Val Arg Ile Lys Val Asp Thr Val Asn Ala Lys Pro Gly Asp Thr Val
        35                  40                  45

Arg Ile Pro Val Arg Phe Ser Gly Ile Pro Ser Lys Gly Ile Ala Asn
    50                  55                  60

Cys Asp Phe Val Tyr Ser Tyr Asp Pro Asn Val Leu Glu Ile Ile Glu
65                  70                  75                  80

Ile Glu Pro Gly Glu Leu Ile Val Asp Pro Asn Pro Thr Lys Ser Phe
                85                  90                  95

Asp Thr Ala Val Tyr Pro Asp Arg Lys Met Ile Val Phe Leu Phe Ala
            100                 105                 110

Glu Asp Ser Gly Thr Gly Ala Tyr Ala Ile Thr Glu Asp Gly Val Phe
        115                 120                 125

Ala Thr Ile Val Ala Lys Val Lys Ser Gly Ala Pro Asn Gly Leu Ser
    130                 135                 140

Val Ile Lys Phe Val Glu Val Gly Gly Phe Ala Asn Asn Asp Leu Val
145                 150                 155                 160

Glu Gln Lys Thr Gln Phe Phe Asp Gly Gly Val Asn Val Gly Thr Arg
                165                 170                 175

Val Gly Ile Pro Lys Glu Ala Cys Pro Thr Gly Leu Tyr Thr His Ser
```

```
            180                 185                 190
Gly Glu Cys Cys Lys Ala Cys Asn Leu Gly Glu Gly Val Ala Gln Pro
            195                 200                 205

Cys Gly Ala Asn Gln Thr Val Cys Glu Pro Cys Leu Asp Ser Val Thr
            210                 215                 220

Phe Ser Asp Val Val Ser Ala Thr Glu Pro Cys Lys Pro Cys Thr Glu
225                 230                 235                 240

Cys Val Gly Leu Gln Ser Met Ser Ala Pro Cys Val Glu Ala Asp Asp
                245                 250                 255

Ala Val Cys Arg Cys Ala Tyr Gly Tyr Tyr Gln Asp Glu Thr Thr Gly
            260                 265                 270

Arg Cys Glu Ala Cys Arg Val Cys Glu Ala Gly Ser Gly Leu Val Phe
            275                 280                 285

Ser Cys Gln Asp Lys Gln Asn Thr Val Cys Glu Cys Pro Asp Gly
            290                 295                 300

Thr Tyr Ser Asp Glu Ala Asn His Val Asp Pro Cys Leu Pro Cys Thr
305                 310                 315                 320

Val Cys Glu Asp Thr Glu Arg Gln Leu Arg Glu Cys Thr Arg Trp Ala
                325                 330                 335

Asp Ala Glu Cys Glu Glu Ile Pro Gly Arg Trp Ile Thr Arg Ser Thr
            340                 345                 350

Pro Pro Glu Gly Ser Asp Ser Thr Ala Pro Ser Thr Gln Glu Pro Glu
            355                 360                 365

Ala Pro Pro Glu Gln Asp Leu Ile Ala Ser Thr Val Ala Gly Val Val
            370                 375                 380

Thr Thr Val Met Gly Ser Ser Gln Pro Val Val Thr Arg Gly Thr Thr
385                 390                 395                 400

Asp Asn Leu Ile Pro Val Tyr Cys Ser Ile Leu Ala Ala Val Val Val
                405                 410                 415

Gly Leu Val Ala Tyr Ile Ala Phe Lys Arg Trp Asn Arg Arg His Lys
            420                 425                 430

Gln Lys Ile Val Ala Pro Val Lys Gln Thr Leu Asn Phe Asp Leu Leu
            435                 440                 445

Lys Leu Ala Gly Asp Val Glu Ser Asn Pro Gly Pro Gly Asp Thr Ser
            450                 455                 460

Ile
465

<210> SEQ ID NO 6
<211> LENGTH: 90
<212> TYPE: PRT
<213> ORGANISM: Artificial Sequence
<220> FEATURE:
<223> OTHER INFORMATION: Synthetic Polypeptide

<400> SEQUENCE: 6

Phe Pro Asn Pro Leu Ser Asp Leu Ser Gly Gln Pro Thr Pro Pro Ser
1               5                   10                  15

Asn Pro Thr Pro Ser Leu Pro Pro Gln Val Val Tyr Gly Asp Val Asn
            20                  25                  30

Gly Asp Gly Asn Val Asn Ser Thr Asp Leu Thr Met Leu Lys Arg Tyr
        35                  40                  45

Leu Leu Lys Ser Val Thr Asn Ile Asn Arg Glu Ala Ala Asp Val Asn
    50                  55                  60

Arg Asp Gly Ala Ile Asn Ser Ser Asp Met Thr Ile Leu Lys Arg Tyr
```

```
                65                  70                  75                  80
Leu Ile Lys Ser Ile Pro His Leu Pro Tyr
                    85                  90

<210> SEQ ID NO 7
<211> LENGTH: 270
<212> TYPE: DNA
<213> ORGANISM: Artificial Sequence
<220> FEATURE:
<223> OTHER INFORMATION: Synthetic Polynucleotide

<400> SEQUENCE: 7
ttcccgaatc ctttgagtga cctttccggc caaccgacac caccgtcgaa tccgacacct      60
tcattgcctc ctcaggttgt ttacggtgat gtaaatggcg acggtaatgt taactccact     120
gatttgacta tgttaaaaag atatctgctg aagagtgtta ccaatataaa cagagaggct     180
gcagacgtta atcgtgacgg tgcgattaac tcctctgaca tgactatatt aaagagatat     240
ctgataaaga gcatacccca cctaccttat                                      270

<210> SEQ ID NO 8
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 8

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 9
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 9

Trp Ser His Pro Gln Phe Glu Lys
1               5

<210> SEQ ID NO 10
<211> LENGTH: 664
<212> TYPE: DNA
<213> ORGANISM: Artificial Sequence
<220> FEATURE:
<223> OTHER INFORMATION: Synthetic Polynucleotide

<400> SEQUENCE: 10
ctagatctga attcggtacc ctagttatta atagtaatca attacggggt cattagttca      60
tagcccatat atggagttcc gcgttacata acttacggta aatggcccgc ctggctgacc     120
gcccaacgac ccccgcccat tgacgtcaat aatgacgtat gttcccatag taacgccaat     180
agggactttc cattgacgtc aatgggtgga ctatttacgg taaactgccc acttggcagt     240
acatcaagtg tatcatatgc caagtacgcc ccctattgac gtcaatgacg gtaaatggcc     300
cgcctggcat tatgcccagt acatgacctt atgggacttt cctacttggc agtacatcta     360
cgtattagtc atcgctatta ccatggtcga ggtgagcccc acgttctgct tcactctccc     420
catctccccc ccctccccac cccaatttt gtatttattt attttttaat tatttttgtgc     480
```

```
agcgatgggg gcggggggggg ggggggggcg cgcgccaggc ggggcggggc ggggcgaggg    540
gcggggcggg gcgaggcgga gaggtgcggc ggcagccaat cagagcggcg cgctccgaaa    600
gtttcctttt atggcgaggc ggcggcggcg gcggccctat aaaaagcgaa gcgcgcggcg    660
ggcg                                                                 664
```

<210> SEQ ID NO 11
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 11

```
atggatccca ctcgagccgc agtaaggatt aagg                                 34
```

<210> SEQ ID NO 12
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 12

```
atggatcctt gggaattcct actcgagttc c                                    31
```

<210> SEQ ID NO 13
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 13

```
tagcggccgc caccatgatg gatcaagcta gat                                  33
```

<210> SEQ ID NO 14
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 14

```
tagtcgactc aagttccaac atttactcca ccgt                                 34
```

<210> SEQ ID NO 15
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 15

```
gatcctccat gggggcaggt gccaccggcc gcgccatgga cgggccgcgc ctgctgctgt     60
tgctgcttct gggggtgtcc cttggaggtg ccac                                 94
```

<210> SEQ ID NO 16
<211> LENGTH: 94
<212> TYPE: DNA
<213> ORGANISM: Artificial Sequence
<220> FEATURE:
<223> OTHER INFORMATION: Synthetic Polynucleotide

<400> SEQUENCE: 16
tcgagtggca cctccaaggg acaccccag aagcagcaac agcagcaggc gcggcccgtc     60
catggcgcgg ccggtggcac ctgcccccat ggag                                94

<210> SEQ ID NO 17
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 17
ccttggaatt cccaaggagg catgccccac aggc                                34

<210> SEQ ID NO 18
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 18
gcaggggcgg ccgctagatc gatgtgtcgc cgggccc                             37

<210> SEQ ID NO 19
<211> LENGTH: 31
<212> TYPE: DNA
<213> ORGANISM: Artificial Sequence
<220> FEATURE:
<223> OTHER INFORMATION: Synthetic Polynucleotide

<400> SEQUENCE: 19
gaaagaattg agatctcgag ccgcagtaag g                                   31

<210> SEQ ID NO 20
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 20
ccacttctat tactcgagtt ccaacattta ctcc                                34

<210> SEQ ID NO 21
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 21
gcagtgaatt cccgaatcct ttgagtgacc tttcc                               35

<210> SEQ ID NO 22
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 22
ggtgctcgag tcaataaggt agg                                            23

```
<210> SEQ ID NO 23
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 23
gaccatatga agggcgagga gctgttcacc                                       30

<210> SEQ ID NO 24
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 24
actgcgaatt ccttatacag ctcgtccatg ccgag                                 35
```

ENGINEERED RECEPTOR/LIGAND SYSTEM FOR DELIVERY OF THERAPEUTIC AGENTS

RELATED APPLICATIONS

This application is a national stage filing under 35 U.S.C. § 371 of PCT International Application PCT/US2016/014398, filed Jan. 21, 2016, entitled "ENGINEERED RECEPTOR/LIGAND SYSTEM FOR DELIVERY OF THERAPEUTIC AGENTS," which claims priority under 35 U.S.C. § 119(e) to U.S. provisional application No. 62/105,951, filed Jan. 21, 2015, the contents of each of which are incorporated herein by reference in their entireties.

BACKGROUND OF INVENTION

Targeted delivery of therapeutic and diagnostic agents has largely relied on associating the agent with a targeting molecule that binds to an endogenously expressed molecule, such as an endogenous receptor. This targeted delivery scheme has been used most frequently for delivery of agents to the blood-brain barrier or other hard-to-target tissues.

SUMMARY OF THE INVENTION

As described herein, previously-developed targeted delivery systems for delivering therapeutic and diagnostic agents to a tissue of interest have drawbacks that have not been addressed to date. For example, with respect to the blood-brain barrier (BBB) and the blood-cerebrospinal fluid barrier (BCSFB), both of which hamper delivery of agents to the brain, others have relied on the use of endogenously expressed receptors, like the transferrin receptor, to assist the agent across the barriers. Unfortunately, these endogenous receptors are expressed in other tissues, resulting in a reduction of specificity and delivery of the agent to other tissues where delivery is not desired. As detailed herein, to overcome this problem, an engineered receptor-ligand system has been developed. In particular, in some embodiments the system utilizes an engineered receptor that is not normally expressed in a subject, such as a receptor having a ligand-binding domain or extracellular domain of a non-mammalian receptor or protein (e.g., if the system is being implemented in a mammalian subject) or a mammalian receptor or protein (e.g., from a different species) having a ligand that does not bind to an endogenous receptor. This engineered receptor is introduced into a subject such that it is expressed in a tissue of interest, such as in the BBB or the BCSFB (e.g, in the ependymal cells of the BCSFB). A ligand for the engineered receptor can then be associated with a therapeutic or diagnostic agent of interest and administered to the subject, resulting in specific, targeted delivery of the agent to the tissue expressing the engineered receptor.

For example, an engineered receptor was developed for targeting the BCSFB (e.g., targeting the ependymal cells of the BCSFB) by combining the human transferrin receptor or human nerve growth factor receptor (NGFR) with the cohesin domain from *Clostridium thermocellum*, which binds to the protein dockerin, which was utilized as the ligand. By expressing the receptor in choroidal ependymocytes, which are part of the BCSFB, it was found that systemically administrated dockerin ligand was able to bind to the receptor and accumulate in ependymocytes, where some of the ligand was transported from the blood side to the brain side.

Accordingly, aspects of the disclosure relate to compositions and methods of targeted delivery of therapeutic or diagnostic agents to a cell or tissue of interest in a subject.

In some aspects, the disclosure relates to a method of targeted delivery of a therapeutic or diagnostic agent to a subject, comprising administering a ligand associated with a therapeutic or diagnostic agent to a mammalian subject expressing a receptor for the ligand, wherein the receptor is not naturally expressed in the subject.

In some embodiments, the receptor comprises a ligand-binding domain of a non-mammalian protein. In some embodiments, the receptor comprises an extracellular domain of a non-mammalian protein that contains the ligand-binding domain. In some embodiments, the non-mammalian protein is a bacterial protein.

In some embodiments, the ligand-binding domain is a cohesin ligand-binding domain. In some embodiments, the ligand comprises a dockerin domain.

In some embodiments, the receptor comprises an intracellular, transmembrane and/or extracellular domain of a mammalian receptor. In some embodiments, the intracellular, transmembrane and/or extracellular domain is a transferrin receptor or nerve growth factor receptor intracellular, transmembrane and/or extracellular domain.

In some embodiments, the therapeutic or diagnostic agent is a therapeutic agent selected from the group consisting of a protein, a peptide, an adeno-associated virus and a small molecule. In some embodiments, the therapeutic or diagnostic agent is a diagnostic agent selected from the group consisting of an enzyme, a fluorescent compound, a radioactive compound, an ultrasound contrast agent, an optical dye, and a paramagnetic metal atom.

In some embodiments, the therapeutic or diagnostic agent is conjugated or fused to the ligand, optionally via a linker. In some embodiments, the therapeutic or diagnostic agent is contained within a nanoparticle. In some embodiments, the ligand is administered to the subject by intravenous injection.

In some embodiments, the receptor is expressed in the choroid plexus of the subject. In some embodiments, subject has a neurodegenerative disease, a lysosomal storage disease, or a brain or central nervous system cancer.

In some embodiments, the subject is a human subject.

Other aspects of the disclosure relate to a method of producing a mammalian subject that expresses a receptor, the method comprising introducing into a mammalian subject a nucleic acid containing a promoter sequence and a sequence that encodes a receptor having a ligand-binding domain, wherein the ligand-binding domain is not naturally expressed in the subject. In some embodiments, the receptor further contains an intracellular, transmembrane and/or extracellular domain of a mammalian receptor. In some embodiments, the promoter sequence is a tissue-specific promoter sequence. In some embodiments, the ligand-binding domain is a ligand-binding domain of a non-mammalian protein. In some embodiments, the non-mammalian protein is a bacterial protein. In some embodiments, the ligand-binding domain is a cohesin ligand-binding domain. In some embodiments, the intracellular, transmembrane and/or extracellular domain is a transferrin receptor or nerve growth factor receptor intracellular, transmembrane and/or extracellular domain. In some embodiments, the nucleic acid is introduced into the subject via a recombinant adeno-associated virus (rAAV) particle containing the nucleic acid.

Yet other aspects of the disclosure relate to a recombinant adeno-associated virus (rAAV) particle comprising a nucleic acid containing a promoter sequence and a sequence that encodes a receptor having a ligand-binding domain of a non-mammalian protein. In some embodiments, the receptor further contains an intracellular, transmembrane and/or extracellular domain of a mammalian receptor. In some embodiments, the intracellular, transmembrane and/or extracellular domain is a transferrin receptor or nerve growth factor receptor intracellular, transmembrane and/or extracellular domain. In some embodiments, the non-mammalian protein is a bacterial protein. In some embodiments, the ligand-binding domain of the bacterial protein is a cohesin ligand-binding domain. In some embodiments, the promoter sequence is a tissue-specific promoter sequence.

BRIEF DESCRIPTION OF THE DRAWINGS

The following drawings form part of the present specification and are included to further demonstrate certain aspects of the present disclosure.

FIGS. 1A-D are a diagram and a series of photographs showing expression of the TfR-cohesin receptor following injection of the receptor into a single brain ventricle. (FIG. 1A) Schematic representation of the exemplary receptor/ligand system. The exemplary receptor is a fusion protein of the human transferrin receptor (TfR) and the bacterial cohesin domain. The construct was cloned into an rAAV9 vector to make AAV9-TfR-cohesin virus. The exemplary ligand is a fusion protein of GFP and the bacterial dockerin domain to make GFP-dockerin. GFP-dockerin is produced in bacterial culture and purified before injection. (FIG. 1B) AAV9-TfR-cohesin vectors were injected in the right lateral ventricle of mouse brains. Two weeks later, brain slices were incubated with GFP-dockerin protein and GFP-dockerin binding with TfR-cohesin was analyzed by fluorescent microscopy to determine the cells that were expressing the receptor. Brain parenchyma near the right ventricle expressed higher levels of the receptor than the contralateral side, presumably because of the higher starting concentration of virus in CSF on the right side. (FIGS. 1C and D) However, the virus concentration in CSF on both sides of the brain was sufficiently high to generate approximately the same level of receptor expression in choroid plexus cells on both sides of the brain. The hole marks the left side of the mouse brain. Scale bars: (B) 0.72 mm, (C, D) 100 µm.

FIGS. 2A-D are a diagram and a series of photographs showing that GFP-dockerin binds cells from the choroid plexus in all ventricles of the brain in vivo. (FIG. 2A) Schematic representation of the ventricular system in the mouse brain showing the approximate positions of the lateral (LV), third (3V), and fourth (4V) ventricles. The b, c, and d vertical lines indicate the approximate location of the brain images shown in FIGS. 2B, C and D. AAV9-TfR-cohesin vector was injected in the right lateral ventricle of mouse brains. Two weeks post vector injection, GFP-dockerin was injected intravenously into mice and GFP-dockerin binding with TfR-cohesin was analyzed by fluorescent microscopy in brain slices from regions b, c, and d of FIG. 2A. The images showed green signal from GFP-dockerin in the choroid plexus of lateral ventricles (FIG. 2B, C arrows), the third ventricle (FIG. 2C arrowhead) and the fourth ventricle (FIG. 2D). The hole marks the left side of the mouse brain. Scale bars: (B) 265 µm, (C) 600 µm, (D) 295 µm.

FIGS. 3A-I are a series of photographs showing the type of cells binding GFP-dockerin in the choroid plexus. Confocal fluorescent images of mouse brain sections showing GFP-dockerin bound to cells of the choroid plexus (FIG. 3A, D, G). The sections were also stained with CD31 antibody, α-tubulin antibody, or cytokeratin 8/18 antibody, illustrated by the staining patterns depicted in FIGS. 3B, E, and H, respectively. CD31 antibody labels endothelial cells of capillaries, while α-tubulin and cytokeratin 8/18 antibodies label the perinuclear cytoplasm of choroidal ependymocytes. FIG. 3C is merged from FIGS. 3A and B, showing that no cells positive for CD31 were binding GFP-dockerin. However, FIG. 3F (merged from FIGS. 3D and E), and FIG. 3I (merged from FIGS. 3G and H) show partial colocalization of GFP-dockerin signal with α-tubulin and cytokeratin 8/18, respectively (arrows). Nuclei were also stained with DAPI blue, illustrated by the staining patterns in FIGS. 3C, F and I. Scale bars: (A-C) 33 µm, (D-F) 22 µm, (G-I) 30 µm.

FIGS. 4A-H are a series of photographs showing membrane location of GFP-dockerin by confocal microscopy. (FIG. 4A, E) Confocal fluorescent images of mouse brain sections showing green fluorescent signal of GFP-dockerin that was bound to or had entered the cytoplasm of choroidal ependymocytes. GFP-dockerin located only on the cell membrane was visualized by staining with anti-GFP antibody (α-GFP, only membrane), illustrated by the staining patterns in FIGS. 4B and F. The apical membrane of choroidal ependymocytes was stained using fluorescent Phalloidin or aquaporin 1 antibody, illustrated by the staining patterns in FIGS. 4C and G, respectively. FIG. 4D is merged from FIG. 4A-C; FIG. 4H is merged from FIG. 4E-G. FIGS. 4D and H show GFP-dockerin receptor is present on the basolateral membrane (arrowheads) and also, at a lower level, on the apical membrane (arrows). Nuclei were stained with DAPI blue, illustrated by the staining patterns in FIGS. 4D and H. Scale bars: (A-D) 6.6 µm, (E-H) 4.4 µm.

FIGS. 5A-C are a series of photographs showing the membrane location of GFP-dockerin by electron microscopy. (FIG. 5A) Light microscopy image showing GFP-dockerin located only on the cell membrane using an anti-GFP antibody and Peroxidase/DAB reaction. (FIG. 5B) Electron microscopy image showing the peroxidase/DAB reaction product in the cell membrane of a choroidal ependymocyte. Arrowheads show peroxidase/DAB reaction product on the basolateral membrane (bl). (FIG. 5C) Electron microscopy image of two ependymocytes, one unlabeled (ep1) and one labeled (ep2), showing both cellular sides, the flat and folded basolateral membrane (bl) and the apical membrane covered with cilia and microvilli (ap). The DAB reaction product, indicating GFP-dockerin, is present on both the basolateral membrane (arrowhead) as well as the apical membrane (arrow) of the choroidal ependymocyte. n=nucleus; ap=apical membrane (brain side); bl=basolateral membrane (blood side); V=cerebral ventricle; ep1=unlabeled ependymocyte; ep2=labeled ependymocyte; tj=tight junction. Scale bars: (A) 50 µm, (B) 1.12 µm, (C) 0.5 µm.

FIGS. 6A-D are a series of photographs showing that GFP-dockerin ligand binds to the cohesin receptor complex regardless of the virus serotype used for transduction or the mammalian receptor used in the cohesin fusion complex. AAV9-TfR-cohesin (FIG. 6A, B) vector or AAV1-NGFR-cohesin (FIG. 6C, D) vector were injected in the right striatum of mouse brains. Two weeks later, brain slices were incubated with GFP-dockerin. Fluorescent microscopy images show the GFP signal of brain slices with (FIG. 6B, D) and without (FIG. 6A, C) GFP-dockerin incubation. The hole marks the left side of the mouse brain Scale bar: 1.4 mm.

FIGS. 7A-E are a diagram and a series of photographs showing the distribution of TfR-cohesin receptor after injection of the receptor into a single brain ventricle. (FIG. 7A) Schematic representation of a mouse brain, sagital view. b-e lines indicate the approximate location of the brain images shown in b-e pictures. AAV9-TfR-cohesin vectors were injected in the right lateral ventricle of mouse brains. Two weeks later, coronal brain slices (FIG. 7B-E) were incubated with GFP-dockerin. Fluorescent microscopy images of rostral-to-caudal coronal sections show the extent of GFP signal from olfactory bulb/anterior olfactory nucleus (FIG. 7B) to hippocampus (FIG. 7E). The hole marks the left side of the mouse brain. Scale bar: 1.3 mm.

DETAILED DESCRIPTION OF THE INVENTION

Aspects of the disclosure relate to methods and compositions for targeting therapeutic or diagnostic agents to specific tissues or organs of a subject by localizing a heterologous receptor in the target tissue or organ of interest in the subject and administering the therapeutic or diagnostic agent to the subject in association with a ligand that is specific for the heterologous receptor. According to the disclosure, the therapeutic or diagnostic agent binds specifically to the heterologous receptor via the ligand and is thereby targeted to the tissue or organ of interest. This prevents non-specific targeting of the therapeutic or diagnostic agent to other tissues or organs in the subject.

As described herein, an engineered receptor/ligand system incorporating the cohesin-dockerin binding pair was developed for targeted delivery to the brain through the blood-cerebrospinal fluid barrier (BCSFB), which generally prevents transport of agents between the blood and the CSF/brain. When the engineered receptor containing cohesin was expressed in cells in the BCSFB, the dockerin ligand for the receptor, which was fused to GFP, was able to bind selectively to the engineered receptor both in vitro and in vivo, resulting in targeted delivery to and transport across the BCSFB. Thus, the engineered receptor/ligand system was able to facilitate both selective binding to a tissue of interest and transport across a restrictive barrier to the CSF/brain.

It is understood in the art that the BCSFB comprises ependymal cells (or ependymocytes) and tight junctions. In some embodiments, upon injection of an adeno-associated virus vector carrying an engineered receptor, the virus would infect the ependymal cells of the choroid plexus. The ependymal cells of the BCSFB would express the receptor on the blood side of the barrier. Subsequently, a ligand that optionally comprises a nanoparticle would be injected intravenously. The carrier would bind to the receptor via the ligand, and the receptor would transport the nanoparticle to the brain side of the ependymal cells. During the transcytosis, the nanoparticle would release the cargo (e.g., a therapeutic or diagnostic agent) so when the vesicle fuses with the cellular membrane, the cargo would be released in the cerebrospinal fluid of the brain ventricles.

Accordingly, aspects of the disclosure relate to compositions and methods of targeted delivery of a therapeutic or diagnostic agent to a mammalian subject, utilizing a receptor that is not naturally expressed in the subject, such as an engineered receptor described herein. Such methods and compositions are useful, e.g., for delivering therapies and diagnostic agents in a targeted manner to potentially reduce off-target effects and toxicity and to lower dosages required for effectiveness of a particular therapeutic or diagnostic.

Methods

Aspects of the disclosure relate to a method of targeted delivery of a therapeutic or diagnostic agent to a subject. In some embodiments, the method comprises administering a ligand associated with a therapeutic or diagnostic agent to a mammalian subject expressing a receptor for the ligand, wherein the receptor is not naturally expressed in the subject. Receptors and ligands are described herein. Diagnostic agents and therapeutic agents are also described herein.

The ligand associated with the therapeutic or diagnostic agent (e.g., in a composition) may be administered by any administration route known in the art or described herein. The route of administration of the ligand may be oral, parenteral, intravitreal, subretinal, by inhalation or topical. The term parenteral as used herein includes intravenous, intraarterial, intraperitoneal, intramuscular, intradermal, intrathoracic, intrathecal, and subcutaneous administration. In some embodiments, the ligand associated with the therapeutic or diagnostic agent (e.g., in a composition) is administered via intravenous injection, intrapleural injection or intravitreal injection.

In some embodiments, the ligand associated with the therapeutic or diagnostic agent is contained within a composition, optionally comprising a pharmaceutically-acceptable carrier as described herein.

The ligand associated with the therapeutic or diagnostic agent or composition is typically administered to a subject in an effective amount, that is, an amount capable of producing a desirable result, such as targeted delivery of the associated therapeutic or diagnostic agent in the subject. The desirable result will depend upon the active agent being administered, the tissue being targeted, the subject and the disease being treated. For example, an effective amount of ligand may be an amount of the ligand required to cross the blood-brain barrier or blood-CSF barrier in order to deliver an agent. As is known in the art, dosage for any one subject depends on many factors, including the subject's size, body surface area, age, the particular ligand and/or agent to be administered, the time and route of administration, general health, and other drugs being administered concurrently. In some embodiments, the amount of ligand associated with therapeutic or diagnostic agent that is administered is calibrated to the amount of receptor expressed in the tissue or organ in the subject, the clearance rate of the ligand associated with therapeutic or diagnostic agent and the affinity of the ligand for the receptor. In some embodiments, the ligand is administered at a dose of between 1 microgram per gram of subject and 100 micrograms per gram of subject, such as between 1 microgram per gram of subject and 15 micrograms per gram of subject. In some embodiments, the ligand is administered, e.g., at a dose of 30 μg to 300 μg or at a dose of 1 milligram to 100 milligrams.

In some embodiments, the method further comprises administering a nucleic acid encoding the engineered (or heterologous) receptor for the ligand to the subject prior to administering the ligand associated with the therapeutic or diagnostic agent. The terms engineered and heterologous are used interchangeably herein. In some embodiments, the nucleic acid is contained within an adeno-associated virus (e.g., a recombinant AAV), a retrovirus, a lentivirus, an adenovirus, an SV40 virus, a herpes virus, a vesicular stomatitis virus, or a poxvirus or the nucleic acid is contained within or conjugated to a nanoparticle. For example, the nucleic acid can be conjugated (e.g., covalently or non-covalently) to a nanoparticle using any method known in the art or described herein. In some embodiments, the nucleic acid is contained within a recombinant adeno-associated virus (rAAV) particle. In some embodiments, the nucleic acid contained within a recombinant AAV particle comprises inverted terminal repeat (ITR) sequences flanking a gene of interest that is operatively linked to an expression control sequence (e.g., a promoter sequence). In some embodiments, the nucleic acid comprises ITR sequences flanking an expression cassette that contains a gene of interest under the control of a promoter (e.g., a heterologous promoter, for example, a promoter sequence non-native to the gene of interest). In some embodiments, the nucleic acid is delivered to the choroid plexus of the subject. In some embodiments, the nucleic acid or particle is delivered via intraventricular injection.

In some embodiments, the nucleic acid or particle is delivered via intrathecal injection, intraventricular injection, intraparenchymal injection or transnasal delivery. In some embodiments, the nucleic acid or particle is delivered by disruption of the BBB and/or BCSFB followed by any administration route known in the art or described herein, such as intravenous or intraarterial injection.

Other aspects of the disclosure relate to a method of producing a mammalian subject that expresses a receptor, the method comprising introducing into a mammalian subject a nucleic acid containing a promoter sequence and a sequence that encodes a receptor having a ligand-binding domain that is not naturally expressed in the subject, such as a ligand-binding domain of a bacterial protein (e.g., a cohesin ligand-binding domain). In some embodiments, the receptor contains an extracellular domain of a non-mammalian protein, which contains the ligand-binding domain. In some embodiments, the receptor further contains an intracellular, transmembrane and/or extracellular domain of a mammalian receptor, e.g., a transferrin receptor or nerve growth factor receptor. Other receptors and receptor domains are further described herein.

The promoter sequence may be any promoter sequence known in the art or described herein. In some embodiments, the promoter is a CMV and chicken beta-actin hybrid promoter. In some embodiments, the promoter sequence is a tissue-specific promoter sequence. Exemplary tissue-specific promoters are described herein.

In some embodiments, the nucleic acid is contained within an adeno-associated virus (e.g., a recombinant AAV), a retrovirus, a lentivirus, an adenovirus, an SV40 virus, a herpes virus, a vesicular stomatitis virus, or a poxvirus or the nucleic acid is contained within or conjugated to a nanoparticle, and the virus or nanoparticle containing the nucleic acid is administered to the subject. In some embodiments, the nucleic acid is introduced into the subject via an rAAV particle containing the nucleic acid. In some embodiments, the rAAV is of a serotype rAAV1, rAAV4, or rAAV9. In some embodiments, the rAAV is of a serotype rAAV1 or rAAV9. In some embodiments, the nucleic acid further comprises ITR sequences, such as AAV2 ITR sequences, flanking the promoter sequence and the sequence that encodes the receptor. In some aspects, the disclosure relates to therapeutic applications for treating patients using a recombinant AAV particle (e.g., administering the rAAV particle described herein to a subject). In some embodiments, the rAAV particle being administered to a subject contains a gene of interest whose expression is under control of a promoter sequence, wherein said gene and promoter sequence are flanked by inverted terminal repeat (ITR) sequences. In some embodiments, the rAAV particle being administered to a subject contains an expression cassette comprising a gene of interest operatively linked to a promoter (e.g., a heterologous promoter, for example, a promoter sequence non-native to the gene of interest) and flanked by ITRs.

The nucleic acid may be administered by any administration route known in the art or described herein. The route of administration of the ligand may be oral, parenteral, intravitreal, subretinal, by direct injection into a target tissue (e.g., by intraventricular injection or direct injection into the brain, pancreas, liver, heart, skeletal muscle, lung, prostate, cervix, or kidney), by inhalation or topical. The term parenteral as used herein includes intravenous, intraarterial, intraperitoneal, intramuscular, intradermal, intrathoracic, intrathecal, and subcutaneous administration. In some embodiments, the nucleic acid is administered via intraventricular injection. Other exemplary administration routes include intracardiac via an intravenous catheter to target the heart or by portal vein to target the liver.

In some embodiments, the nucleic acid (optionally contained within or attached to a virus or nanoparticle) is contained within a composition, optionally comprising a pharmaceutically-acceptable carrier as described herein.

The nucleic acid or composition is typically administered to a subject in an effective amount, that is, an amount capable of producing a desirable result, such as expression of the receptor in the target tissue. The desirable result will depend upon the nucleic acid or composition being administered, the tissue being targeted, the subject and the disease being treated. For example, an effective amount of nucleic acid or composition may be an amount of the nucleic acid or composition required to express the receptor in the blood-brain barrier or blood-CSF barrier. As is known in the art, dosage for any one subject depends on many factors, including the subject's size, body surface area, age, the particular nucleic acid or composition to be administered, the time and route of administration, general health, and other drugs being administered concurrently.

Receptor

Aspects of the disclosure relate to a receptor that is not naturally expressed in a subject (also referred to herein as a heterologous or engineered receptor) and uses thereof in compositions and methods described herein.

In some embodiments, a receptor is not naturally expressed in the subject if a nucleic acid encoding the receptor (in whole or in part) is not endogenous to the subject (e.g., not present in the subject until the nucleic acid is introduced into the subject artificially, such as by gene therapy or another means described herein). A receptor may be determined to be not naturally present in the subject using any method known in the art, e.g., by PCR detection (such as quantitative PCR, PCR followed by sequencing, and the like) of the nucleic acid encoding the receptor in a biological sample from the subject or by immunological assays (such as Western blot, immunohistochemistry, and the like) for detection of the receptor protein in a biological sample from the subject. In some embodiments, if the assay used does not produce a readout significantly above the noise typical for the particular assay, then the receptor is not naturally present in the subject. It is to be understood that the receptor may comprise naturally-occurring sequences, such as an intracellular, transmembrane and/or extracellular domains of an endogenous receptor, as long as the receptor as a whole is not naturally expressed in the subject.

In some embodiments, the receptor comprises a domain of a protein not naturally expressed in endogenous receptors of the subject, such as a non-mammalian protein or a mammalian protein that has a ligand that does not bind to endogenous receptors of the subject. In some embodiments, the domain has an amino acid sequence that is no more than 10%, no more than 20%, no more than 30%, no more than 40%, no more than 50%, no more than 60%, no more than 70%, no more than 80%, no more than 90%, no more than 95%, no more than 98%, or no more than 99% identical to an amino acid sequence in an endogenous receptor of the subject. For example, the heterologous receptor may be a chimeric receptor (e.g., containing a membrane anchoring domain from one protein and a ligand-binding domain from a different protein) or a modified endogenous receptor that binds to a ligand that does not bind to the natural receptor or any other endogenous receptor of the host.

In some embodiments, the receptor at a minimum comprises a membrane anchoring domain, such as a protein domain or a lipid, and ligand-binding domain. In some embodiments, the ligand-binding domain can be a protein-binding domain, a peptide-binding domain, a nucleic acid (e.g., DNA or RNA) binding domain, or a small molecule binding domain.

Exemplary non-mammalian proteins include bacterial proteins, fungal proteins, arthropod proteins, avian proteins, reptile proteins, amphibian proteins, fish proteins, plant proteins and viral proteins. The non-mammalian protein may be, e.g., a scaffold protein, a receptor protein, a secreted protein, an enzyme, a structural protein, a signaling protein, a regulatory protein, a transport protein, a motor protein, a defense protein, or a transcription factor.

Exemplary mammalian proteins include mouse proteins, feline proteins, canine proteins, equine proteins, bovine proteins, porcine proteins, and human proteins. The mammalian protein may be, e.g., a nuclear transcription factor, a cytoplasmic protein, and nuclear or cytoplasmic enzyme.

In some embodiments, the receptor comprises a ligand-binding domain of a non-mammalian protein (e.g., a ligand-binding domain of a receptor, a transcription factor protein or a scaffold protein, a secreted protein, an enzyme, a structural protein, a signaling protein, a regulatory protein, a transport protein, a motor protein, or a defense protein), such as a ligand-binding domain of a bacterial protein, fungal protein, arthropod protein, avian protein, reptile protein, amphibian protein, fish protein, plant protein or viral protein. A ligand-binding domain is a domain that binds to a ligand of interest, such as a natural ligand of a receptor or a natural binding-partner of a protein, such as a binding partner of a transcription factor, a secreted protein, an enzyme, a structural protein, a signaling protein, a regulatory protein, a transport protein, a motor protein, a defense protein, or a scaffold protein including the cohesin-dockerin binding partners. The ligand-binding domain may bind specifically (i.e., bind preferentially or exclusively) to a ligand described herein. Specific binding of a ligand-binding domain to a ligand can be determined using methods known in the art, such as surface-plasmon resonance, enzyme-linked immunosorbant assay (ELISA), yeast two-hybrid analysis, co-immunoprecipitation, neutral acrylamide gel analysis, affinity chromatography, quantitative Western blot, and the like. Nonspecific binding may be detected, e.g., by measuring labeled ligand binding in a sample in the presence of a saturating concentration of an unlabeled ligand that binds to the ligand-binding domain.

One exemplary engineered receptor described herein comprises a ligand binding domain of cohesin and the extracellular, transmembrane, and intracellular domain of transferrin receptor or nerve growth factor receptor. An exemplary ligand for this engineered receptor is a ligand comprising a dockerin domain, which is then associate with a therapeutic or diagnostic agent as described herein.

Another exemplary engineered receptor may utilize the tight binding between the DNA replication protein PCNA (proliferating cell nuclear antigen) and polymerase delta, which is normally found only in the nucleus of mammalian cells that are dividing. The engineered receptor comprises a polymerase delta protein as part of the extracellular domain and a transmembrane domain and/or intracellular domain from a mammalian receptor such as epidermal growth factor receptor (EGFR). In this case, an exemplary ligand is PCNA, which is then associated with a therapeutic or diagnostic agent as described herein.

In some embodiments, the receptor comprises an extracellular domain of a non-mammalian protein, such as an extracellular domain of a non-mammalian receptor. An extracellular domain is a domain that is present on the outside of a cell, such as a domain of a receptor that protrudes from the membrane or cell wall of a cell.

Extracellular and ligand-binding domains of proteins may be identified using any method known in the art or described herein. Exemplary databases for identifying such domains include the Pubmed Protein database at www.ncbi.nlm.nih.gov/protein, the RCSB database at www.rcsb.org/pdb/home/home.do, the Genecards database at www.genecards.org, the Interpro database at www.ebi.ac.uk/interpro, IUPHAR/BSP database at www.guidetopharmacology.org, and the Uniprot database at www.uniprot.org.

In some embodiments, the receptor comprises a cohesin ligand-binding domain, such as a cohesin domain that binds dockerin. In some embodiments, the cohesin domain comprises cohesin 7 of the CipA scaffoldin gene[13]. In some embodiments, the receptor comprises the sequence shown below or a fragment thereof that binds dockerin. In some embodiments, the receptor comprises a sequence that is at least 80%, at least 85%, at least 90%, at least 95%, at least 96%, at least 97%, at least 98%, or at least 99% identical to the sequence shown below.

Exemplary Cohesin Amino Acid Sequence:

```
                                    (SEQ ID NO: 1)
AVRIKVDTVNAKPGDTVRIPVRFSGIPSKGIANCDFVYSYDPNVLEIIEI

EPGELIVDPNPTKSFDTAVYPDRKMIVFLFAEDSGTGAYAITEDGVFATI

VAKVKSGAPNGLSVIKFVEVGGFANNDLVEQKTQFFDGGVNVG
```

In some embodiments, the receptor comprises an extracellular, transmembrane and/or intracellular domain of a mammalian receptor. In some embodiments, the mammalian receptor chosen depends upon the tissue to be targeted, although the choice is not limited in this manner. For example, if targeting the brain, the mammalian receptor may be a transferrin receptor, a nerve growth factor receptor, an insulin receptor, an insulin-like growth factor receptor, a leptin receptor, a neonatal Fc receptor, a scavenger receptor type B, or a low-density lipoprotein receptor. In another example, if targeting the liver, the mammalian receptor may be a hepatocyte growth factor receptor (HGFR). In another example, if targeting the monocyte cells, the mammalian receptor may be a CD14 receptor. In another example, if targeting macrophages, the mammalian receptor may be a CD68 receptor. In another example, if targeting endothelial cells, the mammalian receptor may be a FLT1 receptor. In another example, if targeting the kidney, the mammalian receptor may be a parathyroid hormone receptor (PTH1R).

In some embodiments, the extracellular, transmembrane and/or intracellular domain is a transferrin receptor or nerve growth factor receptor extracellular, transmembrane and/or intracellular domain. In some embodiments, the extracellular, transmembrane and/or intracellular domain comprises the amino acid sequence encoded by a nucleotide sequence shown below or a fragment thereof that, when included in a receptor, anchors the receptor to a cell membrane. In some embodiments, the receptor comprises an amino acid sequence that is at least 80%, at least 85%, at least 90%, at least 95%, at least 96%, at least 97%, at least 98%, or at least 99% identical to the amino acid sequence encoded by a nucleotide sequence shown below.

Exemplary Transferrin Receptor Nucleotide Sequence:

```
                                          (SEQ ID NO: 2)
ATGATGGATCAAGCTAGATCAGCATTCTCTAACTTGTTTGGTGGAGAACC
ATTGTCATATACCCGGTTCAGCCTGGCTCGGCAAGTAGATGGCGATAACA
GTCATGTGGAGATGAAACTTGCTGTAGATGAAGAAGAAATGCTGACAAT
AACACAAAGGCCAATGTCACAAAACCAAAAAGGTGTAGTGGAAGTATCTG
CTATGGGACTATTGCTGTGATCGTCTTTTTCTTGATTGGATTTATGATTG
GCTACTTGGGCTATTGTAAAGGGGTAGAACCAAAAACTGAGTGTGAGAGA
CTGGCAGGAACCGAGTCTCCAGTGAGGGAGGAGCCAGGAGAGGACTTCCC
TGCAGCACGTCGCTTATATTGGGATGACCTGAAGAGAAAGTTGTCGGAGA
AACTGGACAGCACAGACTTCACCAGCACCATCAAGCTGCTGAATGAAAAT
TCATATGTCCCTCGTGAGGCTGGATCTCAAAAAGATGAAAATCTTGCGTT
GTATGTTGAAAATCAATTTCGTGAATTTAAACTCAGCAAAGTCTGGCGTG
ATCAACATTTTGTTAAGATTCAGGTCAAAGACAGCGCTCAAAACTCGGTG
ATCATAGTTGATAAGAACGGTAGACTTGTTTACCTGGTGGAGAATCCTGG
GGGTTATGTGGCGTATAGTAAGGCTGCAACAGTTACTGGTAAACTGGTCC
ATGCTAATTTTGGTACTAAAAAAGATTTTGAGGATTTATACACTCCTGTG
AATGGATCTATAGTGATTGTCAGAGCAGGGAAAATCACCTTTGCAGAAAA
GGTTGCAAATGCTGAAAGCTTAAATGCAATTGGTGTGTTGATATACATGG
ACCAGACTAAATTTCCCATTGTTAACGCAGAACTTTCATTCTTTGGACAT
GCTCATCTGGGGACAGGTGACCCTTACACACCTGGATTCCCTTCCTTCAA
TCACACTCAGTTTCCACCATCTCGGTCATCAGGATTGCCTAATATACCTG
TCCAGACAATCTCCAGAGCTGCTGCAGAAAAGCTGTTTGGGAATATGGAA
GGAGACTGTCCCTCTGACTGGAAAACAGACTCTACATGTAGGATGGTAAC
CTCAGAAAGCAAGAATGTGAAGCTCACTGTGAGCAATGTGCTGAAAGAGA
TAAAAATTCTTAACATCTTTGGAGTTATTAAAGGCTTTGTAGAACCAGAT
CACTATGTTGTAGTTGGGGCCCAGAGAGATGCATGGGGCCCTGGAGCTGC
AAAATCCGGTGTAGGCACAGCTCTCCTATTGAAACTTGCCCAGATGTTCT
CAGATATGGTCTTAAAAGATGGGTTTCAGCCCAGCAGAAGCATTATCTTT
GCCAGTTGGAGTGCTGGAGACTTTGGATCGGTTGGTGCCACTGAATGGCT
AGAGGGATACCTTTCGTCCCTGCATTTAAAGGCTTTCACTTATATTAATC
TGGATAAAGCGGTTCTTGGTACCAGCAACTTCAAGGTTTCTGCCAGCCCA
CTGTTGTATACGCTTATTGAGAAAACAATGCAAAATGTGAAGCATCCGGT
TACTGGGCAATTTCTATATCAGGACAGCAACTGGGCCAGCAAAGTTGAGA
AACTCACTTTAGACAATGCTGCTTTCCCTTTCCTTGCATATTCTGGAATC
CCAGCAGTTTCTTTCTGTTTTTGCGAGGACACAGATTATCCTTATTTGGG
TACCACCATGGACACCTATAAGGAACTGATTGAGAGGATTCCTGAGTTGA
ACAAAGTGGCACGAGCAGCTGCAGAGGTCGCTGGTCAGTTCGTGATTAAA
CTAACCCATGATGTTGAATTGAACCTGGACTATGAGAGGTACAACAGCCA
ACTGCTTTCATTTGTGAGGGATCTGAACCAATACAGAGCAGACATAAAGG
AAATGGGCCTGAGTTTACAGTGGCTGTATTCTGCTCGTGGAGACTTCTTC
CGTGCTACTTCCAGACTAACAACAGATTTCGGGAATGCTGAGAAAACAGA
CAGATTTGTCATGAAGAAACTCAATGATCGTGTCATGAGAGTGGAGTATC
ACTTCCTCTCTCCCTACGTATCTCCAAAAGAGTCTCCTTTCCGACATGTC
TTCTGGGGCTCCGGCTCTCACACGCTGCCAGCTTTACTGGAGAACTTGAA
ACTGCGTAAACAAAATAACGGTGCTTTTAATGAAACGCTGTTCAGAAACC
AGTTGGCTCTAGCTACTTGGACTATTCAGGGAGCTGCAAATGCCCTCTCT
GGTGACGTTTGGGACATTGACAATGAGTTT
```

Italics = intracellular domain, underline = transmembrane domain, rest of sequence = extracellular domain Exemplary Nerve Growth Factor Nucleotide Sequence:

```
                                          (SEQ ID NO: 3)
ATGGGGGCAGGTGCCACCGGCCGCGCCATGGACGGGCCGCGCCTGCTGCT
GTTGCTGCTTCTGGGGGTGTCCCTTGGAGGTGCCACTCGAGTAGGAATTC
CCAAGGAGGCATGCCCCACAGGCCTGTACACACACAGCGGTGAGTGCTGC
AAAGCCTGCAACCTGGGCGAGGGTGTGGCCCAGCCTTGTGGAGCCAACCA
GACCGTGTGTGAGCCCTGCCTGGACAGCGTGACGTTCTCCGACGTGGTGA
GCGCGACCGAGCCGTGCAAGCCGTGCACCGAGTGCGTGGGGCTCCAGAGC
ATGTCGGCGCCGTGCGTGGAGGCCGACGACGCCGTGTGCCGCTGCGCCTA
CGGCTACTACCAGGATGAGACGACTGGGCGCTGCGAGGCGTGCCGCGTGT
GCGAGGCGGGCTCGGGCCTCGTGTTCTCCTGCCAGGACAAGCAGAACACC
GTGTGCGAGGAGTGCCCCGACGGCACGTATTCCGACGAGGCCAACCACGT
GGACCCGTGCCTGCCCTGCACCGTGTGCGAGGACACCGAGCGCCAGCTCC
GCGAGTGCACACGCTGGGCCGACGCCGAGTGCGAGGAGATCCCTGGCCGT
TGGATTACACGGTCCACACCCCCAGAGGGCTCGGACAGCACAGCCCCCAG
CACCCAGGAGCCTGAGGCACCTCCAGAACAAGACCTCATAGCCAGCACGG
TGGCAGGTGTGGTGACCACAGTGATGGGCAGCTCCCAGCCCGTGGTGACC
CGAGGCACCACCGACAACCTCATCCCTGTCTATTGCTCCATCCTGGCTGC
TGTGGTTGTGGGCCTTGTGGCCTACATAGCCTTCAAGAGGTGGAACAGGA
GACACAAACAGAAAATTGTGGCACCGGTGAAACAGACTTTGAATTTTGAC
CTTCTCAAGTTGGCGGGAGACGTCGAGTCCAACCCTGGGCCCGGCGACAC
ATCGATC
```

Bold = Reticulum Signal Peptide, Italics and underlined = Extracellular Domain, Underlined = Transmembrane Domain, Italics = Intracellular Domain.

In some embodiments, the receptor comprises a cohesin domain and a human transferrin or human nerve growth factor receptor domain. In some embodiments, the receptor comprises a cohesin 7 fused to a C-terminus of the human transferrin receptor. In some embodiments, the receptor comprises a cohesin domain inserted in frame between a reticulum signal peptide of nerve growth factor receptor (NGFR) and a NGFR amino acid sequence. In some embodiments, the receptor comprises a sequence as shown below or the receptor comprises a sequence that is at least 80%, at least 85%, at least 90%, at least 95%, at least 96%, at least 97%, at least 98%, or at least 99% identical to the sequence shown below.

Amino Acid Sequence of an Exemplary Engineered Cohesin-Transferrin Receptor:

(SEQ ID NO: 4)
MMDQARSAFSNLFGGEPLSYTRFSLARQVDGDNSHVEMKLAVDEEENADN

NTKANVTKPKRCSGSICYGTIAVIVFFLIGFMIGYLGYCKGVEPKTECER

LAGTESPVREEPGEDFPAARRLYWDDLKRKLSEKLDSTDFTSTIKLLNEN

SYVPREAGSQKDENLALYVENQFREFKLSKVWRDQHFVKIQVKDSAQNSV

IIVDKNGRLVYLVENPGGYVAYSKAATVTGKLVHANFGTKKDFEDLYTPV

NGSIVIVRAGKITFAEKVANAESLNAIGVLIYMDQTKFPIVNAELSFFGH

AHLGTGDPYTPGFPSFNHTQFPPSRSSGLPNIPVQTISRAAAEKLFGNME

GDCPSDWKTDSTCRMVTSESKNVKLTVSNVLKEIKILNIFGVIKGFVEPD

HYVVVGAQRDAWGPGAAKSGVGTALLLKLAQMFSDMVLKDGFQPSRSIIF

ASWSAGDFGSVGATEWLEGYLSSLHLKAFTYINLDKAVLGTSNFKVSASP

LLYTLIEKTMQNVKHPVTGQFLYQDSNWASKVEKLTLDNAAFPFLAYSGI

PAVSFCFCEDTDYPYLGTTMDTYKELIERIPELNKVARAAAEVAGQFVIK

LTHDVELNLDYERYNSQLLSFVRDLNQYRADIKEMGLSLQWLYSARGDFF

RATSRLTTDFGNAEKTDRFVMKKLNDRVMRVEYHFLSPYVSPKESPFRHV

FWGSGSHTLPALLENLKLRKQNNGAFNETLFRNQLALATWTIQGAANALS

GDVWDIDNEFSEFGSTGSTGSTGADPTRAAVRIKVDTVNAKPGDTVRIPV

RFSGIPSKGIANCDFVYSYDPNVLEIIEIEPGELIVDPNPTKSFDTAVYP

DRKMIVFLFAEDSGTGAYAITEDGVFATIVAKVKSGAPNGLSVIKFVEVG

GFANNDLVEQKTQFFDGGVNVGT

Amino Acid Sequence of an Exemplary Engineered Cohesin-NGFR Receptor:

(SEQ ID NO: 5)
MGAGATGRAMDGPRLLLLLLLGVSLGGATRAAVRIKVDTVNAKPGDTVRI

PVRFSGIPSKGIANCDFVYSYDPNVLEIIEIEPGELIVDPNPTKSFDTAV

YPDRKMIVFLFAEDSGTGAYAITEDGVFATIVAKVKSGAPNGLSVIKFVE

VGGFANNDLVEQKTQFFDGGVNVGTRVGIPKEACPTGLYTHSGECCKACN

LGEGVAQPCGANQTVCEPCLDSVTFSDVVSATEPCKPCTECVGLQSMSAP

CVEADDAVCRCAYGYYQDETTGRCEACRVCEAGSGLVFSCQDKQNTVCEE

CPDGTYSDEANHVDPCLPCTVCEDTERQLRECTRWADAECEEIPGRWITR

STPPEGSDSTAPSTQEPEAPPEQDLIASTVAGVVTTVMGSSQPVVTRGTT

-continued
DNLIPVYCSILAAVVVGLVAYIAFKRWNRRHKOKIVAPVKQTLNFDLLKL

AGDVESNPGPGDTSI

In some embodiments, the receptor is localized to an organ or tissue of interest in the subject. The receptor may be localized to an organ or tissue using any method known in the art or described herein. The localization of the receptor may be controlled or adjusted, e.g., by delivering the receptor directly to the organ or tissue (such as by direct injection into the organ or tissue), by utilizing tissue-specific promoters in the receptor expression construct, and/or by utilizing delivery vehicles having tissue-specific properties (such as a specific serotype of rAAV, which may transduce tissues or organs selectively).

The receptor may be made using any method known in the art or described herein. For example, DNA encoding domains from a non-mammalian protein may be combined in frame with DNA encoding an extracellular, transmembrane and/or intracellular domain of a mammalian receptor using standard cloning techniques or by de novo synthesis of the combined coding sequence to produce a construct encoding the receptor. The construct encoding the receptor can be introduced into a nucleic acid vector, such as a plasmid (e.g., comprising an origin of replication (such as an E. coli ORI) and optionally a selectable marker (such as an Ampicillin or Kanamycin selectable marker)). The nucleic acid vector or the construct contained therein can then be formulated for delivery to a tissue or cell of interest using any method known in the art or described herein, e.g., by packaging the nucleic acid vector or the construct into an adeno-associated virus (AAV including recombinant AAV), a retrovirus, a lentivirus (e.g., HIV), an adenovirus, a papovavirus (e.g., an SV40 virus), a herpes virus, a vesicular stomatitis virus, or a poxvirus or by incorporating the nucleic acid vector into or conjugating nucleic acid vector to a nanoparticle, such as a liposome, micelle or polymeric nanoparticle (e.g., poly (lactic-co-glycolic acid) (PLGA)). In some embodiments, for long term or permanent expression of the receptor, the nucleic acid vector is packaged into an AAV, a lentivirus (e.g., HIV), a herpes virus or a papovavirus (e.g., SV40) for delivery to the subject. In some embodiments, for short term expression of receptor (e.g., for one week to three months), the nucleic acid vector is packaged into an adenovirus, a vesicular stomatitis virus (VSV), or any other short term infectious virus (which could be engineered for this purpose using standard molecular biology techniques), or is conjugated to a nanoparticle for delivery to the subject.

Ligand

Other aspects of the disclosure relate to a ligand for a receptor as described herein, wherein the ligand is associated with a therapeutic or diagnostic agent as described herein. In some embodiments, the ligand specifically binds to the receptor (e.g., specifically binds to the ligand-binding domain of the receptor, such as a cohesin domain). In some embodiments, the ligand is a protein or peptide, e.g., comprising a dockerin domain. Although it should be understood that other ligands (e.g., small molecule or a nucleic acid) could be used, provided they have appropriate binding properties, such as those described herein.

In some embodiments, the ligand is one that does not bind to any naturally occurring receptors in a subject or binds to naturally occurring receptors with a dissociation constant ($K_D$) of greater than $10^{-5}$ M or a binding affinity of less than $10^5 M^{-1}$. As used herein, binding affinity ($K_A$) is the reciprocal of the dissociation constant ($K_D$), where $K_D$=[R][L]/

[C], where [R], [L] and [C] represent molar concentrations of the receptor, ligand and complex, respectively. Higher affinity binding of a ligand to a first target relative (e.g., a heterologous receptor) to a second target (e.g., a naturally occurring receptor) can be indicated by a higher $K_A$ (or inversely a smaller $K_D$) for binding the first target than the $K_A$ (or $K_D$) for binding the second target. Conversely, lower affinity binding of a ligand to a first target relative (e.g., a heterologous receptor) to a second target (e.g., a naturally occurring receptor) can be indicated by a lower $K_A$ (or inversely a larger $K_D$) for binding the first target than the $K_A$ (or $K_D$) for binding the second target. Differences in binding affinity between the heterologous receptor and naturally occurring receptors can be at least 2, 3, 4, 5, 10, 15, 20, 37.5, 50, 70, 80, 91, 100, 500, 1000, 10,000 or $10^5$ fold.

In some embodiments, the ligand binds to the heterologous receptor as described herein with a $K_D$ of less than $10^{-8}$, $10^{-9}$, $10^{-10}$, $10^{-11}$, or $10^{-12}$ M or a binding affinity of at least $10^8$, $10^9$, $10^{10}$, $10^{11}$, or $10^{12}$ M$^{-1}$. In some embodiments, the ligand binds to the heterologous receptor as described herein with a $K_D$ of between $10^{-8}$ and $10^{-15}$ M (such as between $10^{-8}$ and $10^{-14}$ M, $10^{-8}$ and $10^{-13}$ M, or $10^{-8}$ and $10^{-12}$ M), or a binding affinity of between $10^8$ and $10^{15}$ M$^{-1}$ (such as between $10^8$ and $10^{14}$ M$^{-1}$, $10^8$ and $10^{13}$ M$^{-1}$, or $10^8$ and $10^{12}$ M$^{-1}$). Ligand and ligand-binding domain pairs for use in the engineered receptor-ligand system described herein can be identified using any method known in the art or described herein. For example, several databases of protein-protein interactions are available, which one of ordinary skill in the art may use to identify protein-protein interactions that guide design of a particular engineered receptor-ligand pair for use in the compositions and methods described herein. Exemplary databases include BioGRID (thebiogrid.org, Version 3.2.119), Database of Interacting Proteins (dip.doe-mbi.ucla.edu/dip/Main.cgi and The Database of Interacting Proteins: 2004 update. Salwinski L, Miller C S, Smith A J, Pettit F K, Bowie J U, Eisenberg D. NAR 32 (Database issue):D449-51 (2004)), Human Protein Reference Database (www.hprd.org and Prasad, T. S. K. et al. (2009) Human Protein Reference Database—2009 Update. Nucleic Acids Research. 37, D767-72), IntAct (www.ebi.ac.uk/intact/and The MIntAct project-IntAct as a common curation platform for 11 molecular interaction databases. Orchard S et al. Nucl. Acids Res. (2013) doi: 10.1093/nar/gkt1115), Molecular INTeraction database (MINT: mint.bio.uniroma2.it/mint/Welcome.do and MINT, the molecular interaction database: 2012 update. Licata L, Briganti L, Peluso D, Perfetto L, Iannuccelli M, Galeota E, Sacco F, Palma A, Nardozza A P, Santonico E, Castagnoli L, Cesareni G. Nucleic Acids Res. 2012 January; 40 (Database issue):D857-61. doi: 10.1093/nar/gkr930), MIPS (mips.helmholtz-muenchen.de/proj/ppi/ and Pagel P, Kovac S, Oesterheld M, Brauner B, Dunger-Kaltenbach I, Frishman G, Montrone C, Mark P, Stümpflen V, Mewes H W, Ruepp A, Frishman D. The MIPS mammalian protein-protein interaction database. Bioinformatics 2005; 21(6):832-834), STRING (string-db.org, version 9.1 and Franceschini A et al. STRING v9.1: protein-protein interaction networks, with increased coverage and integration. Nucleic Acids Res. 2013 January; 41 (Database issue): D808-15. doi: 10.1093/nar/gks1094), DroID (www.droid-b.org/and Murali T, Pacifico S, Yu J, Guest S, Roberts G G 3rd, Finley R L Jr. DroID 2011: a comprehensive, integrated resource for protein, transcription factor, RNA and gene interactions for Drosophila. Nucleic Acids Res. 2010 Oct. 29. doi: 10.1093/nar/gkq109), Mouse protein-protein interactions (genome.gsc.riken.go.jp/ppi/and Suzuki H. et al. (2001) Protein-Protein Interaction Panel using Mouse Full-Length cDNAs. Genome Res.), and other protein databases described in the Center for Molecular Medicine and Genetics Protein Interaction Database page (proteome.wayne.edu/PIDBL.html).

As described herein, one such exemplary binding pair is dockerin and cohesin. Dockerin is a protein domain found in the cellulosome cellular structure. The binding partner of dockerin is the cohesin domain, located on the scaffoldin protein. Binding of the dockerin domains of the cellulosome and the cohesin domains of the scaffoldin protein results in the formation of the cellulosome complex. There are three types of Dockerin domains: I, II and III which bind to Cohesin Type I, Cohesin Type II and Cohesin Type III, respectively.

In some embodiments, the dockerin and cohesin domains are type I, e.g., type I dockerin from the gene CelA and the type I cohesin 7 from the CipA scaffoldin gene from the bacteria *Clostridium thermocellum*. Dockerin type I from *C. thermocellum* shows high affinity ($K_D$ between $10^{-8}$-$10^{-11}$M) for cohesin type I from *C. thermocellum* and does not recognize the closely related cohesin type I from *C. cellulolyticum*. (see, e.g., Pages et al. Species-specificity of the cohesin-dockerin interaction between *Clostridium thermocellum* and *Clostridium cellulolyticum*: prediction of specificity determinants of the dockerin domain. Proteins. 1997 December; 29(4):517-27; and Mechaly et al. Cohesin-dockerin interaction in cellulosome assembly: a single hydroxyl group of a dockerin domain distinguishes between nonrecognition and high affinity recognition. J Biol Chem. 2001 Mar. 30; 276(13):9883-8.)

Other exemplary species having dockerin and cohesin domains for use with the disclosure include *Clostridium thermocellum*, *Clostridium acetobutylicum* and *Clostridium cellulolyticum*. Other exemplary species include *Acetivibrio cellulolyticus*, *Bacteroides cellulosolvens*, *Clostridium cellulovorans*, *Clostridium clariflavum*, *Clostridium josui*, *Clostridium papyrosolvens*, *Ruminococcus albus*, and *Ruminococcus flavefaciens*.

In some embodiments, the ligand is a peptide or protein comprising a dockerin domain. In some embodiments, the dockerin domain comprises the amino acid sequence shown below or a fragment thereof that binds to cohesin. In some embodiments, the dockerin domain comprises a sequence that is at least 80%, at least 85%, at least 90%, at least 95%, at least 96%, at least 97%, at least 98%, or at least 99% identical to the amino acid sequence shown below.

Exemplary Dockerin Amino Acid Sequence:

(SEQ ID NO: 6)
FPNPLSDLSGQPTPPSNPTPSLPPQVVYGDVNGDGNVNSTDLTMLKRYLL

KSVTNINREAADVNRDGAINSSDMTILKRYLIKSIPHLPY

Exemplary Dockerin Nucleotide Sequence:

(SEQ ID NO: 7)
TTCCCGAATCCTTTGAGTGACCTTTCCGGCCAACCGACACCACCGTCGAA

TCCGACACCTTCATTGCCTCCTCAGGTTGTTTACGGTGATGTAAATGGCG

ACGGTAATGTTAACTCCACTGATTTGACTATGTTAAAAAGATATCTGCTG

AAGAGTGTTACCAATATAAACAGAGAGGCTGCAGACGTTAATCGTGACGG

```
TGCGATTAACTCCTCTGACATGACTATATTAAAGAGATATCTGATAAAGA

GCATACCCCACCTACCTTAT
```

Other exemplary interacting proteins or peptides that could be used to design a ligand and receptor pair as described herein include Proliferating cell nuclear antigen (PNCA) and polymerase delta, Barnase and barstar, RNase SA and barstar, Colicin E9 and Im9 (immunity protein specific for ColE9), Colicin E9 and Im2 (immunity protein specific for ColE2), Chymotrypsin and BPTI (bovine pancreatic trypsin inhibitor), Trypsin and BPTI, Flu hemagglutinin and Fab HC19, Fab D44.1 and lysozyme, HIV-1 Nef and Fyn SH3 domain (R96I), TCR-Vβ and SEC3-1A4 variant, Cole9 and Lm9, Calmodulin and the peptide having the sequence KRRWKKNFIAVSAANRFKKISSSGAL (SEQ ID NO: 8), and Streptavidin and Strep-tag II (WSHPQFEK, SEQ ID NO: 9) (see, e.g., Panagiotis L Kastritis et al. A structure-based benchmark for protein— protein binding affinity. Protein Sci. March 2011; 20(3): 482-491; and Garinot-Schneider et al. Identification of residues in the putative TolA box which are essential for the toxicity of the endonuclease toxin colicin E9. Microbiology September 1997 vol. 143 no. 9: 2931-2938; and Hartley. Barnase and barstar: two small proteins to fold and fit together. Trends Biochem Sci. 1989 November; 14(11):450-4).

In some embodiments, a first ligand and a second ligand are contemplated herein for use with a first receptor and a second receptor, e.g., to deliver two diagnostic or therapeutic agents to a subject. For example, the first ligand may comprise a dockerin from a first species and the first receptor may comprise a first cohesin from the first species, whereas the second ligand may comprise a dockerin from a second species and the second receptor may comprise a second cohesin from the second species. For example, dockerin/cohesin from *Clostridium thermocellum* can be used to deliver a first diagnostic or therapeutic agent while a dockerin/cohesin pair from *Clostridium cellulolyticum* can be used to deliver the second diagnostic or therapeutic agent. In some embodiments, the first species is selected from the group consisting of *Clostridium thermocellum, Clostridium acetobutylicum, Clostridium cellulolyticum, Acetivibrio cellulolyticus, Bacteroides cellulosolvens, Clostridium cellulovorans, Clostridium clariflavum, Clostridium josui, Clostridium papyrosolvens, Ruminococcus albus,* and *Ruminococcus flavefaciens,* and the second species is a different species selected from the group consisting of *Clostridium thermocellum, Clostridium acetobutylicum, Clostridium cellulolyticum, Acetivibrio cellulolyticus, Bacteroides cellulosolvens, Clostridium cellulovorans, Clostridium clariflavum, Clostridium josui, Clostridium papyrosolvens, Ruminococcus albus,* and *Ruminococcus flavefaciens.*

A ligand as described herein can be produced using any method known in the art or described herein, such as by recombinant expression of the ligand in a host cell or by synthesis of the ligand. The host cell can be, e.g., a bacterial cell, an insect cell or a mammalian cell. Recombinant methods for producing protein and peptide ligands are known in the art (see, e.g., Wingfield, P. T. 2010. Production of Recombinant Proteins. Current Protocols in Protein Science. 61:5.0:5.0.1-5.0.4; Murphy, C. I., Piwnica-Worms, H., Grünwald, S., Romanow, W. G., Francis, N. and Fan, H.-Y. 2004. Expression and Purification of Recombinant Proteins Using the Baculovirus System. Current Protocols in Molecular Biology. 65:II:16.11:16.11.1-16.11.14; and LaVallie, E. R. 2001. Production of Recombinant Proteins in *Escherichia coli.* Current Protocols in Protein Science. 00:5.1:5.1.1-5.1.8). Methods of synthesizing ligands, such as peptides, include liquid-phase synthesis and solid-phase synthesis, which are known in the art and commercially available (see, e.g., Albericio, F. (2000). Solid-Phase Synthesis: A Practical Guide (1 ed.). Boca Raton: CRC Press; Stawikowski, M. and Fields, G. B. 2012. Introduction to Peptide Synthesis. Current Protocols in Protein Science. 69:18.1:18.1.1-18.1.13; and commercial synthesis services available from Pierce Biotechnology, Inc., Genscript, Sigma-Aldrich, and Life Technologies).

Therapeutic and Diagnostic Agents

Other aspects of the disclosure relate to a ligand as described herein (e.g., a ligand comprising a dockerin domain) associated with a therapeutic or diagnostic agent.

Any therapeutic agent known in the art or described herein is completed for use with a ligand as described herein. In some embodiments, the therapeutic agent is selected from the group consisting of a protein, a peptide, a DNA molecule (or fragment thereof), an RNA molecule (or fragment thereof), a virus (such as an adeno-associated virus) or a small molecule or other drug compound.

Exemplary, non-limiting therapeutic proteins include enzymes, transcription factors, structural proteins, receptors, transport proteins, and antibodies (including antigen-binding fragments thereof). Non-limiting examples of therapeutic proteins and peptides include Erythropoietin, Granulocyte colony-stimulating factor, Human growth hormone, human insulin, Follicle-stimulating hormone, Factor VIII, alpha-galactosidase A, alpha-L-iduronidase, N-acetylgalactosamine-4-sulfatase, Dornase alfa, Tissue plasminogen activator, Glucocerebrosidase, Interferon-beta-1a, Insulin-like growth factor 1, somatotropin, Factor IX, Antithrombin III, Protein C, Iduronate-2-sulphatase, Galsulphase, α-1-Proteinase inhibitor, Lactase, lipase, amylase, protease, Adenosine deaminase, Pooled immunoglobulins, Human albumin, Darbepoetin-α, interleukin11, Human follicle-stimulating hormone, Human chorionic gonadotropin, Lutropin-α, Type I alpha-interferon, Interferon-α2a, Interferon-α2b, Interferon-αn3, Interferon-β1a, Interferon-β1b, Interferon-γ1b, interleukin 2, Reteplase, Tenecteplase, Urokinase, Factor VIIa, Drotrecogin-α, Salmon calcitonin, Teriparatide, Exenatide, Octreotide, Dibotermin-α, Recombinant human bone morphogenic protein 7, Histrelin acetate, keratinocyte growth factor, Becaplermin, Trypsin, Nesiritide, Botulinum toxin type A, Botulinum toxin type B, Collagenase, Human deoxyribonuclease I, Hyaluronidase, Papain, 1-Asparaginase, Rasburicase, Lepirudin, Bivalirudin, Streptokinase, Anistreplase, Bevacizumab, Cetuximab, Panitumumab, Alemtuzumab, Rituximab, Trastuzumab, Abatacept, Anakinra, Adalimumab, Etanercept, Infliximab, Alefacept, Efalizumab, Natalizumab, Eculizumab, Antithymocyte globulin (rabbit), Basiliximab, Daclizumab, MuromonabCD3, Omalizumab, Palivizumab, Enfuvirtide, Abciximab, Pegvisomant, Crotalidae polyvalent immune Fab (ovine), Digoxin immune serum Fab (ovine), Ranibizumab, Denileukin diftitox, Ibritumomab tiuxetan, Gemtuzumab ozogamicin, Tositumomab, Hepatitis B surface antigen, Anti-Rhesus (Rh) immunoglobulin G (see, e.g., Leader et al. Protein therapeutics: a summary and pharmacological classification. 2008. Nature Reviews: Drug Discovery. Vol 7, 21-39). Other examples of therapeutic proteins and peptides are provided in Table 2.

Exemplary therapeutic proteins and peptides for delivery across the BBB or the BCSFB include, but are not limited to nerve growth factor (NGF), brain derived neurotrophic factor (BDNF), ciliary neurotrophic factor (CNTF), glial cell-line neurotrophic factor (GDNF) and insulin-like growth factor (IGF), Substance P, neuropeptide Y, and vasoactive intestinal peptide (VIP).

Exemplary, non-limiting therapeutic adeno-associated viruses include rAAVs carrying a nucleic acid construct encoding a protein or peptide of interest. Exemplary proteins and peptides that can be encapsidated in a rAAV is provided in Table 2 below. The rAAV may be of any serotype known in the art or described herein. The nucleic acid construct may further comprise a promoter or enhancer sequence known in the art or described herein.

TABLE 2

Exemplary proteins and peptides

| Protein or Peptide | Non-limiting exemplary diseases, disorders, or phenotypes | Non-limiting NCBI Protein IDs or Patent SEQ ID NOs |
|---|---|---|
| beta-catenin (CTNNB1) | hepatocellular carcinoma | NP_001091679.1, NP_001091680.1, NP_001895.1 |
| pyruvate dehydrogenase (PDH) | hepatocellular carcinoma | NP_000275.1, NP_001166925.1, NP_001166926.1, NP_001166927.1, NP_000916.2, NP_001166939.1 |
| parvovirus B19 non-structural protein (B19 NS1) | hepatocellular carcinoma | YP_004928144.1 |
| Trichosanthin (TCS) | hepatocellular carcinoma | XP_008243881.1 |
| beta-globin (HBB) | hemoglobinopathies | NP_000509.1 |
| acid alpha-glucosidase (GAA) | Pompe disease | NP_000143.2, NP_001073271.1, NP_001073272.1 |
| Methyl CpG binding protein 2 (MECP2) | Rett syndrome | NP_001104262.1, NP_004983.1 |
| Aromatic L-amino acid decarboxylase (AADC) | Parkinson's disease | NP_000781.1, NP_001076440.1, NP_001229815.1, NP_001229816.1, NP_001229817.1, NP_001229818.1, NP_001229819.1 |
| Glial cell-derived neurotrophic factor (GDNF) | Parkinson's disease | NP_000505.1, NP_001177397.1, NP_001177398.1, NP_001265027.1, NP_954701.1 |
| Cystic fibrosis transmembrane conductance regulator (CFTR) | Cystic fibrosis | NP_000483.3 |
| Tumor necrosis factor receptor fused to an antibody Fc (TNFR:Fc) | Arthritis, Rheumatoid arthritis | SEQ ID NO. 1 of WO2013025079 |
| HIV-1 gag-proΔrt (tgAAC09) | HIV infection | SEQ ID NOs. 1-5 of WO2006073496 |
| Sarcoglycan alpha, beta, gamma, delta, epsilon, or zeta (SGCA, SGCB, SGCG, SGCD, SGCE, or SGCZ) | Muscular dystrophy | SGCA NP_000014.1, NP_001129169.1 SGCB NP_000223.1 SGCG NP_000222.1 SGCD NP_000328.2, NP_001121681.1, NP_758447.1 SGCE NP_001092870.1, NP_001092871.1, NP_003910.1 SGCZ NP_631906.2 |
| Alpha-1-antitrypsin (AAT) | Hereditary emphysema or Alpha-1-antitrypsin deficiency | NP_000286.3, NP_001002235.1, NP_001002236.1, NP_001121172.1, NP_001121173.1, NP_001121174.1, NP_001121175.1, NP_001121176.1, NP_001121177.1, NP_001121178.1, NP_001121179.1 |

TABLE 2-continued

Exemplary proteins and peptides

| Protein or Peptide | Non-limiting exemplary diseases, disorders, or phenotypes | Non-limiting NCBI Protein IDs or Patent SEQ ID NOs |
|---|---|---|
| Glutamate decarboxylase 1(GAD1) | Parkinson's disease | NP_000808.2, NP_038473.2 |
| Glutamate decarboxylase 2 (GAD2) | Parkinson's disease | NP_000809.1, NP_001127838.1 |
| Aspartoacylase (ASPA) | Canavan's disease | NP_000040.1, NP_001121557.1 |
| Nerve growth factor (NGF) | Alzheimer's disease | NP_002497.2 |
| Granulocyte-macrophage colony stimulating factory (GM-CSF) | Prostate cancer | NP_000749.2 |
| Cluster of Differentiation 86 (CD86 or B7-2) | Malignant melanoma | NP_001193853.1, NP_001193854.1, NP_008820.3, NP_787058.4, NP_795711.1 |
| Interleukin 12 (IL-12) | Malignant melanoma | NP_000873.2, NP_002178.2 |
| neuropeptide Y (NPY) | Parkinson's disease, epilepsy | NP_000896.1 |
| ATPase, Ca++ transporting, cardiac muscle, slow twitch 2 (SERCA2) | Chronic heart failure | NP_001672.1, NP_733765.1 |
| Dystrophin or Minidystrophin | Muscular dystrophy | NP_000100.2, NP_003997.1, NP_004000.1, NP_004001.1, NP_004002.2, NP_004003.1, NP_004004.1, NP_004005.1, NP_004006.1, NP_004007.1, NP_004008.1, NP_004009.1, NP_004010.1, NP_004011.2, NP_004012.1, NP_004013.1, NP_004014.1 |
| Ceroid lipofuscinosis neuronal 2 (CLN2) | Late infantile neuronal ceroidlipofuscinosis or Batten's disease | NP_000382.3 |
| Neurturin (NRTN) | Parkinson's disease | NP_004549.1 |
| N-acetylglucosaminidase, alpha (NAGLU) | Sanfilippo syndrome (MPSIIIB) | NP_000254.2 |
| Iduronidase, alpha-1 (IDUA) | MPSI-Hurler | NP_000194.2 |
| Iduronate 2-sulfatase (IDS) | MPSII-Hunter | NP_000193.1, NP_001160022.1, NP_006114.1 |
| Glucuronidase, beta (GUSB) | MPSVII-Sly | NP_000172.2, NP_001271219.1 |
| Hexosaminidase A, α polypeptide, also called beta-Hexosaminidase alpha (HEXA) | Tay-Sachs | NP_000511.2 |
| Hexosaminidase B, β polypeptide, also called beta-Hexosaminidase beta (HEXB) | Tay-Sachs | NP_000512.1, NP_001278933.1 |
| Retinal pigment epithelium-specific protein 65 kDa (RPE65) | Leber congenital amaurosis | NP_000320.1 |
| Factor IX (FIX) | Hemophilia B | NP_000124.1 |
| Adenine nucleotide translocator (ANT-1) | progressive external ophthalmoplegia | NP_001142.2 |
| ApaLI | mitochondrial heteroplasmy, myoclonic epilepsy with ragged red fibers (MERRF) or mitochondrial encephalomyopathy, lactic acidosis, and stroke-like episodes (MELAS) | YP_007161330.1 |

TABLE 2-continued

Exemplary proteins and peptides

| Protein or Peptide | Non-limiting exemplary diseases, disorders, or phenotypes | Non-limiting NCBI Protein IDs or Patent SEQ ID NOs |
|---|---|---|
| NADH ubiquinone oxidoreductase subunit 4 (ND4) | Leber hereditary optic | YP_003024035.1 |
| very long-acyl-CoA dehydrogenase (VLCAD) | very long-chain acyl-CoA dehydrogenase (VLCAD) deficiency | NP_000009.1, NP_001029031.1, NP_001257376.1, NP_001257377.1 |
| short-chain acyl-CoA dehydrogenase (SCAD) | short-chain acyl-CoA dehydrogenase (SCAD) deficiency | NP_000008.1 |
| medium-chain acyl-CoA dehydrogenase (MCAD) | medium-chain acyl-CoA dehydrogenase (MCAD) deficiency | NP_000007.1, NP_001120800.1, NP_001272971.1, NP_001272972.1, NP_001272973.1 |
| Myotubularin 1 (MTM1) | X-linked myotubular myopathy | NP_000243.1 |
| Myophosphorylase (PYGM) | McArdle disease (glycogen storage disease type V, myophosphorylase deficiency) | NP_001158188.1, NP_005600.1 |
| Lipoprotein lipase (LPL) | LPL deficiency | NP_000228.1 |
| sFLT01 (VEGF/PlGF (placental growth factor) binding domain of human VEGFR1/Flt-1 (hVEGFR1) fused to the Fc portion of human IgG(1) through a polyglycine linker) | Age-related macular degeneration | SEQ ID NO: 2, 8, 21, 23, or 25 of WO2009105669 |
| Glucocerebrosidase (GC) | Gaucher disease | NP_000148.2, NP_001005741.1, NP_001005742.1, NP_001165282.1, NP_001165283.1 |
| UDP glucuronosyltransferase 1 family, polypeptide A1 (UGT1A1) | Crigler-Najjar syndrome | NP_000454.1 |
| Glucose 6-phosphatase (G6Pase) | GSD-Ia | NP_000142.2, NP_001257326.1 |
| Ornithine carbamoyltransferase (OTC) | OTC deficiency | NP_000522.3 |
| Cystathionine-beta-synthase (CBS) | Homocystinuria | NP_000062.1, NP_001171479.1, NP_001171480.1 |
| Factor VIII (F8) | Haemophilia A | NP_000123.1, NP_063916.1 |
| Hemochromatosis (HFE) | Hemochromatosis | NP_000401.1, NP_620572.1, NP_620573.1, NP_620575.1, NP_620576.1, NP_620577.1, NP_620578.1, NP_620579.1, NP_620580.1 |
| Low density lipoprotein receptor (LDLR) | Phenylketonuria (PKU) | NP_000518.1, NP_001182727.1, NP_001182728.1, NP_001182729.1, NP_001182732.1 |
| Galactosidase, alpha (AGA) | Fabry disease | NP_000160.1 |
| Phenylalanine hydroxylase (PAH) | Hypercholesterolaemia or Phenylketonuria (PKU) | NP_000268.1 |
| Propionyl CoA carboxylase, alpha polypeptide (PCCA) | Propionic acidaemias | NP_000273.2, NP_001121164.1, NP_001171475.1 |
| myosin 7A (MYO7A) | Usher syndrome 1B | NP_000251.3, NP_001120651.2, NP_001120652.1 |

Therapeutic small molecules are also known in the art and commercially available (see, e.g., Approved Drug Products with therapeutic equivalence evaluations, 34$^{th}$ edition. U.S. DEPARTMENT OF HEALTH AND HUMAN SERVICES. FOOD AND DRUG ADMINISTRATION. 2014). Specific examples of non-limiting therapeutic small molecules include the lists as follows, which are classified by type of small molecule, but are understood not to be limited by the type.

Adrenergic: Adrenalone; Amidephrine Mesylate; Apraclonidine Hydrochloride; Brimonidine Tartrate; Dapiprazole Hydrochloride; Deterenol Hydrochloride; Dipivefrin; Dopamine Hydrochloride; Ephedrine Sulfate; Epinephrine; Epinephrine Bitartrate; Epinephryl Borate; Esproquin Hydrochloride; Etafedrine Hydrochloride; Hydroxyamphetamine Hydrobromide; Levonordefrin; Mephentermine Sulfate; Metaraminol Bitartrate; Metizoline Hydrochloride; Naphazoline Hydrochloride; Norepinephrine Bitartrate; Oxidopamine; Oxymetazoline Hydrochloride; Phenylephrine Hydrochloride; Phenylpropanolamine Hydrochloride; Phenylpropanolamine Polistirex; Prenalterol Hydrochloride; Propylhexedrine; Pseudoephedrine Hydrochloride; Tetrahydrozoline Hydrochloride; Tramazoline Hydrochloride; and Xylometazoline Hydrochloride.

Adrenocortical steroid: Ciprocinonide; Desoxycorticosterone Acetate; Desoxycorticosterone Pivalate; Dexamethasone Acetate; Fludrocortisone Acetate; Flumoxonide; Hydrocortisone Hemisuccinate; Methylprednisolone Hemisuccinate; Naflocort; Procinonide; Timobesone Acetate; and Tipredane.

Adrenocortical suppressant: Aminoglutethimide; and Trilostane.

Alcohol deterrent: Disulfiram.

Aldosterone antagonist: Canrenoate Potassium; Canrenone; Dicirenone; Mexrenoate Potassium; Prorenoate Potassium; and Spironolactone.

Amino acid: Alanine; Arginine; Aspartic Acid; Carnitine; Cysteine Hydrochloride; Cystine; Glycine; Histidine; Isoleucine; Leucine; Lysine; Lysine Acetate; Lysine Hydrochloride; Methionine; Phenylalanine; Proline; Serine; Threonine; Tryptophan; Tyrosine; and Valine.

Ammonia detoxicant: Arginine Glutamate; and Arginine Hydrochloride.

Amyotrophic lateral sclerosis agents: Riluzole

Anabolic: Bolandiol Dipropionate; Bolasterone; Boldenone Undecylenate; Bolenol; Bolmantalate; Ethylestrenol; Methenolone Acetate; Methenolone Enanthate; Mibolerone; Nandrolone Cyclotate; Norbolethone; Pizotyline; Quinbolone; Stenbolone Acetate; Tibolone; and Zeranol.

Analeptic: Modafinil.

Analgesic: Acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lornoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zomepirac Sodium; and Zucapsaicin.

Androgen: Fluoxymesterone; Mesterolone; Methyltestosterone; Nandrolone Decanoate; Nandrolone Phenpropionate; Nisterime Acetate; Oxandrolone; Oxymetholone; Silandrone; Stanozolol; Testosterone; Testosterone Cypionate; Testosterone Enanthate; Testosterone Ketolaurate; Testosterone Phenylacetate; Testosterone Propionate; Trestolone Acetate.

Anesthesia (adjunct to): Sodium Oxybate.

Anesthetic: Aliflurane; Benoxinate Hydrochloride; Benzocaine; Biphenamine Hydrochloride; Bupivacaine Hydrochloride; Butamben; Butamben Picrate; Chloroprocaine Hydrochloride; Cocaine; Cocaine Hydrochloride; Cyclopropane; Desflurane; Dexivacaine; Diamocaine Cyclamate; Dibucaine; Dibucaine Hydrochloride; Dyclonine Hydrochloride; Enflurane; Ether; Ethyl Chloride; Etidocaine; Etoxadrol Hydrochloride; Euprocin Hydrochloride; Fluroxene; Halothane; Isobutamben; Isoflurane; Ketamine Hydrochloride; Levoxadrol Hydrochloride; Lidocaine; Lidocaine Hydrochloride; Mepivacaine Hydrochloride; Methohexital Sodium; Methoxyflurane; Midazolam Hydrochloride; Midazolam Maleate; Minaxolone; Norflurane; Octodrine; Oxethazaine; Phencyclidine Hydrochloride; Pramoxine Hydrochloride; Prilocaine Hydrochloride; Procaine Hydrochloride; Propanidid; Proparacaine Hydrochloride; Propofol; Propoxycaine Hydrochloride; Pyrrocaine; Risocaine; Rodocaine; Roflurane; Salicyl Alcohol; Sevoflurane; Teflurane; Tetracaine; Tetracaine Hydrochloride; Thiamylal; Thiamylal Sodium; Thiopental Sodium; Tiletamine Hydrochloride; and Zolamine Hydrochloride.

Anorectic compound: Dexfenfluramine.

Anorexic agents: Aminorex; Ampheloral; Chlorphentermine Hydrochloride; Clominorex; Clortermine Hydrochloride; Diethylpropion Hydrochloride; Fenfluramine Hydrochloride; Fenisorex; Fludorex; Fluminorex; Levamfetamine Succinate; Mazindol; Mefenorex Hydrochloride; Phemnetrazine Hydrochloride; Phentermine; and Sibutramine Hydrochloride.

Antagonist: Atipamezole; Atosiban; Bosentan; Cimetidine; Cimetidine Hydrochloride; Clentiazem Maleate;

Detirelix Acetate; Devazepide; Donetidine; Etintidine Hydrochloride; Famotidine; Fenmetozole Hydrochloride; Flumazenil; Icatibant Acetate; Icotidine; Isradipine; Metiamide; Nadide; Nalmefene; Naloxone Hydrochloride; Naltrexone; Nilvadipine; Oxilorphan; Oxmetidine Hydrochloride; Oxmetidine Mesylate; Quadazocine Mesylate; Ranitidine; Ranitidine Bismuth Citrate; Ranitidine Hydrochloride; Sufotidine; Teludipine Hydrochloride; Tiapamil Hydrochloride; Tiotidine; Vapiprost Hydrochloride; and Zaltidine Hydrochloride.

Anterior pituitary activator: Epimestrol.

Anterior pituitary suppressant: Danazol.

Anthelmintic: Albendazole; Anthelmycin; Bromoxanide; Bunamidine Hydrochloride; Butonate; Cambendazole; Carbantel Lauryl Sulfate; Clioxanide; Closantel; Cyclobendazole; Dichlorvos; Diethylcarbamazine Citrate; Dribendazole; Dymanthine Hydrochloride; Etibendazole; Fenbendazole; Furodazole; Hexylresorcinol; Mebendazole; Morantel Tartrate; Niclosamide; Nitramisole Hydrochloride; Nitrodan; Oxantel Pamoate; Oxfendazole; Oxibendazole; Parbendazole; Piperamide Maleate; Piperazine; Piperazine Citrate; Piperazine Edetate Calcium; Proclonol; Pyrantel Pamoate; Pyrantel Tartrate; Pyrvinium Pamoate; Rafoxanide; Stilbazium Iodide; Tetramisole Hydrochloride; Thiabendazole; Ticarbodine; Tioxidazole; Triclofenol Piperazine; Vincofos; and Zilantel.

Anti-acne: Adapalene; Erythromycin, Salnacedin; and Inocoterone Acetate.

Anti-adrenergic: Acebutolol; Alprenolol Hydrochloride; Atenolol; Bretylium Tosylate; Bunolol Hydrochloride; Carteolol Hydrochloride; Celiprolol Hydrochloride; Cetamolol Hydrochloride; Cicloprolol Hydrochloride; Dexpropranolol Hydrochloride; Diacetolol Hydrochloride; Dihydroergotamine Mesylate; Dilevalol Hydrochloride; Esmolol Hydrochloride; Exaprolol Hydrochloride; Fenspiride Hydrochloride; Flestolol Sulfate; Labetalol Hydrochloride; Levobetaxolol Hydrochloride; Levobunolol Hydrochloride; Metalol Hydrochloride; Metoprolol; Metoprolol Tartrate; Nadolol; Pamatolol Sulfate; Penbutolol Sulfate; Phentolamine Mesylate; Practolol; Propranolol Hydrochloride; Proroxan Hydrochloride; Solypertine Tartrate; Sotalol Hydrochloride; Timolol; Timolol Maleate; Tiprenolol Hydrochloride; Tolamolol; and Zolertine Hydrochloride.

Anti-allergic: Amlexanox; Astemizole; Azelastine Hydrochloride; Eclazolast; Minocromil Nedocromil Nedocromil Calcium; Nedocromil Sodium; Nivimedone Sodium; Pemirolast Potassium Pentigetide; Pirquinozol; Poisonoak Extract; Probicromil Calcium; Proxicromil; Repirinast; Tetrazolast Meglumine; Thiazinamium Chloride; Tiacrilast; Tiacrilast Sodium; Tiprinast Meglumine; and Tixanox.

Anti-amebic: Berythromycin; Bialamicol Hydrochloride; Chloroquine; Chloroquine Hydrochloride; Chloroquine Phosphate; Clamoxyquin Hydrochloride; Clioquinol; Emetine Hydrochloride; Iodoquinol; Paromomycin Sulfate; Quinfamide; Symetine Hydrochloride; Teclozan; Tetracycline; and Tetracycline Hydrochloride.

Anti-androgen: Benorterone; Cioteronel; Cyproterone Acetate; Delmadinone Acetate; Oxendolone; Topterone; and Zanoterone.

Anti-anemic: Epoetin Alfa; Epoetin Beta; Ferrous Sulfate, Dried; and Leucovorin Calcium.

Anti-anginal: Amlodipine Besylate; Amlodipine Maleate; Betaxolol Hydrochloride; Bevantolol Hydrochloride; Butoprozine Hydrochloride; Carvedilol; Cinepazet Maleate; Metoprolol Succinate; Molsidomine; Monatepil Maleate; Primidolol; Ranolazine Hydrochloride; Tosifen; and Verapamil Hydrochloride.

Anti-anxiety agent: Adatanserin Hydrochloride; Alpidem; Binospirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; and Zalospirone Hydrochloride.

Anti-arthritic: Lodelaben.

Anti-asthmatic: Ablukast; Ablukast Sodium; Bunaprolast; Cinalukast; Cromitrile Sodium; Cromolyn Sodium; Enofelast; Isamoxole; Ketotifen Fumarate; Levcromakalim; Lodoxamide Ethyl; Lodoxamide Tromethamine; Montelukast Sodium; Ontazolast; Oxarbazole; Oxatomide; Piriprost; Piriprost Potassium; Pirolate; Pobilukast Edamine; Quazolast; Ritolukast; Sulukast; Tiaramide Hydrochloride; Tibenelast Sodium; Tomelukast; Tranilast; Verlukast; and Verofylline Zarirlukast.

Anti-atherosclerotic: Mifobate; and Timefurone.

Antibacterial: Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylate sodium; Aminosalicylic acid; Amoxicillin; Amphomycin; Ampicillin; Ampicillin Sodium; Apalcillin Sodium; Apramycin; Aspartocin; Astromicin Sulfate; A vilamycin; A voparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Betamicin Sulfate; Biapenem; Biniramycin; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftiroxime Pivoxetil; Ceftizoxime Sodium; Ceftriaxone Sodium; Cefuroxime; Cefuroxime Axetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isepamicin; Isoconazole; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifarthiazole; Nifuradene; Nifuraldezone; Nifuratel; Nifuratrone; Nifurdazil; Nifurimide; Nifurpirinol; Nifurquinazol; Nitrocycline; Nitrofurantoin; Nitromide; Norfloxacin; Novobiocin Sodium; Ofloxacin; Onnetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; To sufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; and Zorbamycin.

Anti-cancer supplementary potentiating agents: Amitryptyline; Amoxapine; Amphotericin B; Antiarrhythmic drugs (e.g., Quinidine); Antihypertensive drugs (e.g., Reserpine); Ca++ antagonists (e.g., Verapamil; Calmodulin inhibitors (e.g., Prenylamine; Caroverine); Citalopram); Clomipramine; Clomipramine); Desipramine; Doxepin; Maprotiline); Nifedipine; Nitrendipine; Non-tricyclic anti-depressant drugs (e.g., Sertraline; Nortriptyline; Protriptyline; Sulfoximine) and Multiple Drug Resistance reducing agents such as Cremaphor EL; Thiol depleters (e.g., Buthionine; Trazodone; Tricyclic anti-depressant drugs (e.g., Imipramine; Trifluoroperazine; Trimipramine; and Triparanol analogues (e.g., Tamoxifen).

Anticholelithic: Monoctanoin.

Anticholelithogenic: Chenodiol; Ursodiol.

Anticholinergic: Alverinc Citrate; Anisotropine Methylbromide; Atropine; Atropine Oxide Hydrochloride; Atropine Sulfate; Belladonna; Benapryzine Hydrochloride; Benzetimide Hydrochloride; Benzilonium Bromide; Biperiden; Biperiden Hydrochloride; Biperiden Lactate; Clidinium Bromide; Cyclopentolate Hydrochloride; Dexetimide; Dicyclomine Hydrochloride; Dihexyverine Hydrochloride; Domazoline Fumarate; Elantrine; Elucaine; Ethybenztropine; Eucatropine Hydrochloride; Glycopyrrolate; Heteronium Bromide; Homatropine Hydrobromide; Homatropine Methylbromide; Hyoscyamine; Hyoscyamine Hydrobromide; Hyoscyamine Sulfate; Isopropamide Iodide; Mepenzolate Bromide; Methylatropine Nitrate; Metoquizine; Oxybutynin Chloride; Parapenzolate Bromide; Pentapiperium Methylsulfate; Phencarbamide; Poldine Methylsulfate; Proglumide; Propantheline Bromide; Propenzolate Hydrochloride; Scopolamine Hydrobromide; Tematropium Methylsulfate; Tiquinamide Hydrochloride; Tofenacin Hydrochloride; Toquizine; Triampyzine Sulfate; Trihexyphenidyl Hydrochloride; and Tropicamide. Anticoagulant: Ancrod; Ardeparin Sodium; Bivalirudin; Bromindione; Dalteparin Sodium Desirudin; Dicumarol; Lyapolate Sodium; Nafamostat Mesylate; Phenprocoumon; Tinzaparin Sodium; and Warfarin Sodium.

Anticoccidal: Maduramicin.

Anticonvulsant: Albutoin; Ameltolide; Atolide; Buramate; Cinromide; Citenamide; Clonazepam; Cyheptamide; Dezinamide; Dimethadione; Divalproex Sodium; Eterobarb; Ethosuximide; Ethotoin; Flurazepam Hydrochloride; Fluzinamide; Fosphenytoin Sodium; Gabapentin; Ilepcimide; Lamotrigine; Magnesium Sulfate; Mephenytoin; Mephobarbital; Methetoin; Methsuximide; Milacemide Hydrochloride; Nabazenil; Nafimidone Hydrochloride; Nitrazepam; Phenacemide; Phenobarbital; Phenobarbital Sodium; Phensuximide; Phenytoin; Phenytoin Sodium; Primidone; Progabide; Ralitoline; Remacemide Hydrochloride; Ropizine; Sabeluzole; Stiripentol; Sulthiame; Topiramate; Trimethadione; Valproate Sodium; Valproic Acid; Vigabatrin; Zoniclezole Hydrochloride; and Zonisamide.

Antidepressant: Adinazolam; Adinazolam Mesylate; Alaproclate; Aletamine Hydrochloride; Amedalin Hydrochloride; Amitriptyline Hydrochloride; Aptazapine Maleate; Azaloxan Fumarate; Azepindole; Azipramine Hydrochloride; Bipenamol Hydrochloride; Bupropion Hydrochloride; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide;

Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pride fine Hydrochloride; Prolintane Hydrochloride; Protriptyline Hydrochloride; Quipazine Maleate; Rolicyprine; Seproxetine Hydrochloride; Sertraline Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine Maleate; Venlafaxine Hydrochloride; Viloxazine Hydrochloride; Zimeldine Hydrochloride; and Zometapine.

Antidiabetic: Acetohexamide; Buformin; Butoxamine Hydrochloride; Camighbose; Chlorpropamide; Ciglitazone; Englitazone Sodium; Etoformin Hydrochloride; Gliamilide; Glibornuride; Glicetanile Sodium; Gliflumide; Glipizide; Glucagon; Glyburide; Glyhexamide; Glymidine Sodium; Glyoctamide; Glyparamide; Insulin; Insulin Human; Insulin Human Zinc; Insulin Human Zinc, Extended; Insulin Human, Isophane; Insulin Lispro; Insulin Zinc; Insulin Zinc, Extended; Insulin Zinc, Prompt; Insulin, Dalanated; Insulin, Isophane; Insulin, Neutral; Linogliride; Linogliride Fumarate; Metformin; Methyl Palmoxirate; Palmoxirate Sodium; Pioglitazone Hydrochloride; Pirogliride Tartrate; Proinsulin Human; Seglitide Acetate; Tolazamide; Tolbutamide; Tolpyrramide; Troglitazone; and Zopolrestat.

Antidiarrheal: Diphenoxylate Hydrochloride; Methylprednisolone; Metronidazole; and Rolgamidine.

Antidiuretic: Argipressin Tannate; Desmopres sin Acetate; and Lypressin.

Antidote: Dimercaprol; Edrophonium Chloride; Fomepizole; Levoleucovorin Calcium; Methylene Blue; and Protamine Sulfate.

Antidyskinetic: Selegiline Hydrochloride.

Anti-emetic: Alosetron Hydrochloride; Batanopride Hydrochloride; Bemesetron; Benzquinamide; Chlorpromazine; Chlorpromazine Hydrochloride; Clebopride; Cyclizine Hydrochloride; Dimenhydrinate; Diphenidol; Diphenidol Hydrochloride; Diphenidol Pamoate; Dolasetron Mesylate; Domperidone; Dronabinol; Flumeridone; Galdansetron Hydrochloride; Granisetron; Granisetron Hydrochloride; Lurosetron Mesylate; Meclizine Hydrochloride; Metoclopramide Hydrochloride; Metopimazine; Prochlorperazine; Prochlorperazine Edisylate; Prochlorperazine Maleate; Promethazine Hydrochloride; Thiethylperazine; Thiethylperazine Malate; Thiethylperazine Maleate; Trimethobenzamide Hydrochloride; and Zacopride Hydrochloride.

Anti-epileptic: Felbamate; lamotrigine; Loreclezole; and Tolgabide.

Anti-estrogen: Clometherone; Nafoxidine Hydrochloride; Nitromifene Citrate; Raloxifene Hydrochloride; Tamoxifen Citrate; Toremifene Citrate; and Trioxifene Mesylate.

Antifibrinolytic: Nafamostat Mesylate.

Antifungal: Acrisorcin; Ambruticin; Azaconazole; Azaserine; Basifungin; Bifonazole; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Itraconazole; Kalafungin; Ketoconazole; Lomoftmgin; Lydimycin; Mepartricin; Miconazole; Miconazole Nitrate; Monensin; Monensin Sodium; Naftifine Hydrochloride; Nifuratel Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Pyrrolnitrin; Rutamycin; Sanguinarium Chloride; Saperconazole; Selenium Sulfide; Sinefungin; Sulconazole Nitrate; Terbinafine; Terconazole; Thiram; Tioconazole; Tolciclate; Tolindate; Tolnaftate; Triacetin; Triafungin; Undecylenic Acid; Viridofulvin; Zinc Undecylenate; and Zinoconazole Hydrochloride.

Antiglaucoma agent: Alprenoxime Hydrochloride; Colforsin; Dipivefrin Hydrochloride; Naboctate Hydrochloride; Pilocarpine; and Pirnabine.

Antihemorrhagic: Poliglusam.

Antihemorrheologic: Phentoxifylline.

Antihistaminic: Acrivastine; Antazoline Phosphate; Azatadine Maleate; Barmastine; Bromodiphenhydramine Hydrochloride; Brompheniramine Maleate; Carbinoxamine Maleate; Cetirizine Hydrochloride; Chlorpheniramine Maleate; Chlorpheniramine Polistirex; Cirmarizine; Clemastine; Clemastine Fumarate; Closiramine Aceturate; Cycliramine Maleate; Cyclizine; Cyproheptadine Hydrochloride; Dexbrompheniramine Maleate; Dexchlorpheniramine Maleate; Dimethindene Maleate; Diphenhydramine Citrate; Diphenhydramine Hydrochloride; Dorastine Hydrochloride; Doxylamine Succinate; Ebastine; Fexofenadine HCl; Levocabastine Hydrochloride; Loratadine; Mianserin Hydrochloride; Noberastine; Orphenadrine Citrate; Pyrabrom; Pyrilamine Maleate; Pyroxamine Maleate; Rocastine Hydrochloride; Rotoxamine; Tazifylline Hydrochloride; Temelastine; Terfenadine; Tripelennamine Citrate; Tripelennamine Hydrochloride; and Triprolidine Hydrochloride.

Antihyperlipidemic: Cholestyramine Resin; Clofibrate; Colestipol Hydrochloride; Crilvastatin; Dalvastatin; Dextrothyroxine Sodium; Fluvastatin Sodium; Gemfibrozil; Lecimibide; Lovastatin; Niacin; Pravastatin Sodium; Probucol; Simvastatin; Tiqueside; and Xenbucin.

Antihyperlipoproteinemic: Acifran; Beloxamide; Bezafibrate; Boxidine; Cetaben Sodium; Ciprofibrate; Gemcadiol; Halofenate; Lifibrate; Meglutol; Nafenopin; Pimetine Hydrochloride; Theofibrate; Tibric Acid; and Treloxinate.

Antihypertensive: Alfuzosin Hydrochloride; Alipamide; Althiazide; Amiquinsin Hydrochloride; Anaritide Acetate; Atiprosin Maleate; Belfosdil; Bemitradine; Bendacalol Mesylate; Bendroflumethiazide; Benzthiazide; Bethanidine Sulfate; Biclodil Hydrochloride; Bisoprolol; Bisoprolol Fumarate; Bucindolol Hydrochloride; Bupicomide; Buthiazide; Candoxat rilat; Candoxatril; Captopril; Ceronapril; Chlorothiazide Sodium; Cicletanine; Cilazapril; Clonidine; Clonidine Hydrochloride; Clopamide; Cyclopenthiazide;

Cyclothiazide; Darodipine; Debrisoquin Sulfate; Delapril Hydrochloride; Diapamide; Diazoxide; Diltiazem Hydrochloride; Diltiazem Malate; Ditekiren; Doxazosin Mesylate; Ecadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancvdine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxvfen Sulfate; Hydralazine Hydrochloride; Hydralazine Polistirex; Hydroflumethiazide; Indacrinone Indapamide; Indolapril Hydrochloride; Indoramin; Indoramin Hydrochloride; Indorenate Hydrochloride; Lacidipine; Leniquinsin; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide Methyclothiazide Methyldopa; Methyldopate Hydrochloride; Metipranolol; Metolazone Metoprolol Fumarate; Metyrosine; Minoxidil; Muzolimine; Nebivolol; Nifidipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Temocapril Hydrochloride; Terazosin Hydrochloride; Terlakiren; Tiamenidine; Tiamenidine Hydrochloride; Ticrynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; and Zofenoprilat Arginine.

Antihypotensive: Ciclafrine Hydrochloride; and Midodrine Hydrochloride.

Anti-infective: Acyclovir; Difloxacin Hydrochloride; Integrase Inhibitors of HIV and other retroviruses; Lauryl Isoquinolinium Bromide; Moxalactam Disodium; Ornidazole; Pentisomicin; Protease inhibitors of HIV and other retroviruses; and Sarafloxacin Hydrochloride.

Anti-infective (topical): Alcohol; Aminacrine Hydrochloride; Benzethonium Chloride; Bithionolate Sodium; Bromchlorenone; Carbamide Peroxide; Cetalkonium Chloride; Cetylpyridinium Chloride; Chlorhexidine Hydrochloride; Domiphen Bromide; Fenticlor; Fludazonium Chloride; Fuchsin, Basic; Furazolidone; Gentian Violet; Halquinols; Hexachlorophene; Hydrogen Peroxide; Ichthammol; Imidecyl Iodine; Iodine; Isopropyl Alcohol; Mafenide Acetate; Meralein Sodium; Mercufenol Chloride; Mercury, Ammoniated; Methylbenzethonium Chloride; Nitrofarazone; Nitromersol; Octenidine Hydrochloride; Oxychlorosene; Oxychlorosene Sodium; Parachlorophenol, Camphorated; Potassium Permanganate; Povidone-Iodine; Sepazonium Chloride; Silver Nitrate; Sulfadiazine, Silver; Symclosene; Thimerfonate Sodium; Thimerosal; and Troclosene Potassium.

Anti-inflammatory: Alclofenac; Alclometasone Dipropionate; Algestone Acetonide; Alpha Amylase; Amcinafal; Amcinafide; Amfenac Sodium; Amiprilose Hydrochloride; Anakinra; Anitrazafen; Apazone; Balsalazide Disodium; Bendazac; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Difluprednate; Diftalone; Dimethyl Sulfoxide; Drocinonide; Endrysone; Enlimomab; Enolicam Sodium; Etodolac; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Fluocortin Butyl; Fluorometholone Acetate; Fluquazone; Fluretofen; Fluticasone Propionate; Furaprofen; Furobufen; Halcinonide; Halobetasol Propionate; Halopredone Acetate; Ibuprofen; Ibuprofen Aluminum; Ibuprofen Piconol; Ilonidap; Indomethacin Sodium; Indomethacin; Indoprofen Indoxole; Intrazole; Isoflupredone Acetate; Isoxepac; Isoxicam; Ketoprofen; Lomoxicam; Loteprednol Etabonate; Meclofenamate Sodium; Meclofenamic Acid; Meclorisonc Dibutyrate; Mesalamine; Meseclazone; Methylprednisolone Suleptanate; Morniflumate; Nabumetone; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Piroxicam; Piroxicam Cinnamate; Pirprofen; Prednazate; Prednisolone Sodium Phosphate; Prifelone; Prodolic Acid; Proquazone; Rimexolone; Romazarit; Salnacedin; Seclazone; Sermetacin; Sudoxicam; Sulindac; Suprofen; Talniflumate; Tenidap; Tenidap Sodium; Tenoxicam; Tesicam; Tesimide; Tixocortol Pivalate; Tolmetin; Tolmetin Sodium; Triclonide; Triflumidate; and Zidometacin.

Antikeratinizing agent: Doretinel; Linarotene; and Pelretin.

Antimalarial: Amodiaquine Hydrochloride; Amquinate; Artefiene; Chloroquine; Chloroquine Hydrochloride; Cycloguanil Pamoate; Enpiroline Phosphate; Halofantrine Hydrochloride; Hydroxychloroquine Sulfate; Mefloquine Hydrochloride; Menoctone; Primaquine Phosphate; Pyrimethamine; Quinine Sulfate; and Tebuquine.

Antimicrobial: Aztreonam; Chlorhexidine Gluconate; Imidurea; Lycetamine; Nibroxane; Pirazmonam Sodium; Propionic Acid; Pyrithione Sodium; and Tigemonam Dicholine.

Antimigraine: Naratriptan Hydrochloride; Sergolexole Maleate; Sumatriptan Succinate; and Zatosetron Maleate.

Antimitotic: Podofilox.

Antimycotic: Amorolfine.

Antinauseant: Buclizine Hydrochloride; and Cyclizine Lactate.

Antineoplastic: Acivicin; Aclarubicin; Acodazole Hydrochloride; Acronine; Adozelesin; Aldesleukin; Altretamine; Ambomycin; Ametantrone Acetate; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cisplatin; Cladribine; Crisnatol Mesylate; Cyclophosphamide; Cytarabine; Dacarbazine; Dactinomycin; Daunorubicin Hydrochloride; Decitabine; Dexorinaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Ethiodized Oil I 131;

Etoposide; Etoposide Phosphate; Etoprine; Fadrozole Hydrochloride; Fazarabine; Fenretinide; Floxuridine; Fludarabine Phosphate; Fluorouracil; Flurocitabine; Fosquidone; Fostriecin Sodium; Gemcitabine; Gemcitabine Hydrochloride; Gold Au 198; Hydroxyurea; Idarubicin, Hydrochloride; Ifosfamide; Ilmofosine; Interferon Alfa-2a; Interferon Alfa-2b; Interferon Alfan3; Interferon Alfa-nI; Interferon Beta-I a; Interferon Gamma-I b; Iproplatin; Irinotecan Hydrochloride; Isotretinoin; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamvcin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Prednimustine; Procarbazine Hydrochloride; Puromycin; Puromycin Hydrochloride; Pyrazofurin; Riboprine; Rogletimide; Safingol Safingol Hydrochloride; Semustine; Simtrazene; Sparfosate Sodium; Sparsomycin; Spiro germanium Hydrochloride; Spiromustine; Spiroplatin; Streptonigrin; Streptozocin; Strontium Chloride Sr 89; Sulofenur; Talisomycin; Taxane; Taxoid; Tecogalan Sodium; Tegafur; Teloxantrone Hydrochloride; Temoporfin; Teniposide; Teroxirone; Testolactone; Thiamiprine; Thioguanine; Thiotepa; Tiazofarin; Tirapazamine; Topotecan Hydrochloride; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; and Zorubicin Hydrochloride.

Anti-neoplastic compounds (additional): 20-epi-1,25 Dihydroxyvitamin D3; 5-Ethynyluracil; Abiraterone; Acylfulvene; Adecypenol; ALL-TK Antagonists; Ambamustine; Amidox; Amifostine; Aminolevulinic Acid; Amrubicin; Anagrelide; Andrographolide; Angiogenesis Inhibitors; Antagonist D; Antagonist G; Antarelix; Antiandrogen, Prostatic Carcinoma; Anti-Dorsalizing Morphogenetic Protein-I; Antiestrogen; Antineoplaston; Antisense Oligonucleotides; Aphidicolin Glycinate; Apoptosis Gene Modulators; Apoptosis Regulators; Apurinic Acid; Ara-CDP-DL-PTBA; Arginine Deaminase; Asulacrine; Atamestane; Atrimustine; Axinastatin 1; Axinastatin 2; Axinastatin 3; Azasetron; Azatoxin; Azatyrosine; Baccatin III Derivatives; Balanol; BCR/ABL Antagonists; Benzochlorins; Benzoylstaurosporine; Beta Lactam Derivatives; Beta-Alethine; Betaclamycin B; Betulinic Acid; bFGF Inhibitor; Bisantrene; Bisaziridinylspermine; Bisnafide; Bistratene A; Breflate; Budotitane; Buthionine Sulfoximine; Calcipotriol; Calphostin C; Camptothecin Derivatives; Canarypox IL-2; Capecitabine; Carboxamide-Amino-Triazole; Carboxyamidotriazole; CaRest MI; CARN 700, Cartilage Derived Inhibitor; Casein Kinase Inhibitors (1COS); Castanospermine; Cecropin B; Cetrorelix; Chlorins; Chloroquinoxaline Sulfonamide; Cicaprost; Cis-Porphyrin; Clomifene analogues; Collismycin A; Collismycin B; Combretastatin A4; Combretastatin Analogue; Conagenin; Crambescidin 816; Crisnatol; Cryptophycin 8; Cryptophycin A Derivatives; Curacin A; Cyclopentanthraquinones; Cycloplatam; Cypemycin; Cytarabine Ocfosfate; Cytolytic Factor; Cytostatin; Dacliximab; Dehydrodidenmin B; Dexifosfamide; Dexverapamil; Didemnin B; Didox; Diethylnorspennine; Dihydro Azacytidine; Dihydrotaxol, 9-; Dioxamycin; Diphenyl Spiromustine; Docosanol; Dolasetron; Doxifluridine; Duocarmycin SA; Ebselen; Ecomustine; Edelfosine; Edrecolomab; Eflomithine; Elemene; Emitefur; Epirubicin; Estramustine Analogue; Estrogen Agonists; Estrogen Antagonists; Exemestane; Fadrozole; Fiezelastine; Flavopiridol; Fluasterone; Fludarabine; Fluorodaunorunicin Hydrochloride; Forfenimex; Formestane; Fostriecin; Fotemustine; Gadolinium Texaphyrin; Gallium Nitrate; Galocitabine; Ganirelix; Gelatinase Inhibitors; Glutathione Inhibitors; Hepsulfam; Heregulin; Hexamethylene Bisacetamide; Hypericin; Ibandronic acid; Idarubicin; Idoxifene; Idramantone; Ilomastat; Imidazoacridones; Immunostimulant Peptides; Insulin-Like Growth Factor-I Receptor Inhibitor; Interferon Agonists; Interferons; Interleukins; Iobenguane; Iododoxorubicin; Ipomeanol, 4-; Irinotecan; Iroplact; Irsogladine; Isobengazole; Isohomohalicondrin B; Itasetron; Jasplakinolide; Kahalalide F; Lamellarin-N Triacetate; Lanreotide; Leinamycin; Lentinan Sulfate; Leptolstatin; Leukemia Inhibiting Factor; Leukocyte Alpha Interferon; Leuprolide+Estrogen+Progesterone; Leuprorelin; Levamisole; Liarozole; Linear Polyamine Analogue; Lipophilic Disaccharide Peptide; Lipophilic Platinum Compounds; Lissoclinamide 7; Lobaplatin; Lombricine; Lometrexol; Lonidamine; Losoxantrone; Lurtotecan; Lutetium Texaphyrin; Lysofylline; Lytic Peptides; Maitansine; Mannostatin A; Marimastat; Maspin; Matrilysin Inhibitors; Matrix Metalloproteinase Inhibitors; Merbarone; Meterelin; Methioninase; Metoclopramide; MIF Inhibitor; Mifepristone; Miltefosine; Mirimostim; Mismatched Double Stranded RNA; Mitoguazone; Mitolactol; Mitomycin analogues; Mitonafide; Mitotoxin Fibroblast Growth Factor-Saporin; Mitoxantrone; Mofarotene; Monoclonal Antibody, Human Chorionic Gonadotrophin; Monophosphoryl Lipid A+Myobacterium Cell Wall Sk; Mopidamol; Multiple Drug Resistance Gene Inhibitor; Multiple Tumor Suppressor I-Based Therapy; Mustard Anticancer Agent; Mycaperoxide B; Mycobacterial Cell Wall Extract; Myriaporone; N-Acetyldinaline; Nafarelin; Nagrestip; Naloxone+Pentazocine; Napavin; Naphterpin; Nartograstim; Nedaplatin; Nemorubicin; Neridronic Acid; Neutral Endopeptidase; Nilutamide; Nisamycin; Nitric Oxide Modulators; Nitroxide Antioxidant; Nitrullyn; N-Substituted Benzamides; 06-Benzylguanine; Okicenone; Oligonucleotides; Onapristone; Ondansetron; Oracin; Oral Cytokine Inducer; Osaterone; Oxaliplatin; Oxaunomycin; Paclitaxel Analogues; Paclitaxel Derivatives; Palauamine; Palmitoylrhizoxin; Pamidronic Acid; Panaxytriol; Panomifene; Parabactin; Pazelliptine; Peldesine; Pentostatin; Pentrozole; Perflubron; Perillyl Alcohol; Phenazinomycin; Phenylacetate; Phosphatase Inhibitors; Picibanil; Pilocarpine Hydrochloride; Pirarubicin; Piritrexim; Placetin A; Placetin B; Plasminogen Activator Inhibitor; Platinum Complex; Platinum Compounds; Platinum-Triamine Complex; Propyl Bis-Acridone; Prostaglandin J2; Proteasome Inhibitors; Protein A-Based Immune Modulator; Protein Kinase C Inhibitor; Protein Kinase C Inhibitors, Microalgal; Protein Tyrosine Phosphatase Inhibitors; Purine Nucleoside Phosphorylase Inhibitors; Purpurins; Pyrazoloacridine; Pyridoxylated Hemoglobin Polyoxyethylene Conjugate; Raf Antagonists; Raltitrexed; Ramosetron; Ras Famesyl Protein Transferase Inhibitors; Ras Inhibitors; Ras-GAP Inhibitor; Retelliptine Demethylated; Rhenium, Re 186 Etidronate; Rhizoxin; Ribozymes; RH Retinamide; Rohitukine; Romurtide; Roquinimex; Rubiginone B 1; Ruboxyl; Safingol; Saintopin; SarCNU;

Sarcophytol A; Sdi 1 Mimetics; Senescence Derived Inhibitor 1; Sense Oligonucleotides; Signal Transduction Inhibitors; Signal Transduction Modulators; Single Chain Antigen Binding Protein; Sizofiran; Sobuzoxane; Sodium Borocaptate; Sodium Phenylacetate; Solverol; Somatomedin Binding Protein; Sonermin; Sparfosic Acid; Spicamycin D; Splenopentin; Spongistatin 1; Squalamine; Stem Cell Inhibitor; Stem-Cell Division Inhibitors; Stipiamide; Stromelysin Inhibitors; Sulfinosine; Superactive Vasoactive Intestinal Peptide Antagonist; Suradista; Suramin; Swainsonine; Synthetic Glycosaminoglycans; Tallimustine; Tamoxifen Methiodide; Tauromustine; Tellurapyrylium; Telomerase Inhibitors; Temozolomide; Tetrachlorodecaoxide; Tetrazomine; Thaliblastine; Thalidomide; Thiocoraline; Thrombopoietin; Thrombopoietin Mimetic; Thymalfasin; Thymopoietin Receptor Agonist; Thymotrinan; Thyroid Stimulating Hormone; Tin Ethyl Etiopurpurin; Titanocene Dichloride; Topotecan; Topsentin; Toremifene; Totipotent Stem Cell Factor; Translation Inhibitors; Triacetyluridine; Triciribine; Tropisetron; Turosteride; Tyrosine Kinase Inhibitors; Tyrphostins; UBC Inhibitors; Ubenimex; Urogenital Sinus-Derived Growth Inhibitory Factor; Urokinase Receptor Antagonists; Variolin B; Vector system, Erythrocyte Gene Therapy; Velaresol; Veramine; Verdins; Vinorelbine; Vinxaltine; Vitaxin; Zilascorb; and Zinostatin Stimalamer.

Antineutropenic: Filgrastim; Lenograstim; Molgramostim; Regramostim; and Sargramostim.

Antiobsessional agent: Fluvoxamine Maleate.

Antiparasitic: Abamectin; Clorsulon; and Ivermectin.

Antiparkinsonian: Benztropine Mesylate; Biperiden; Biperiden Hydrochloride; Biperiden Lactate; Carbidopa-Levodopa; Carmantadine; Ciladopa Hydrochloride; Dopamantine; Ethopropazine Hydrochloride; Lazabemide; Levodopa; Lometraline Hydrochloride; Mofegiline Hydrochloride; Naxagolide Hydrochloride; Pareptide Sulfate; Procyclidine Hydrochloride; Ropinirole Hydrochloride; and Tolcapone.

Antiperistaltic: Difenoximide Hydrochloride; Difenoxin; Fluperamide; Lidamidine Hydrochloride; Loperamide Hydrochloride; Malethamer; Nufenoxole; Paregoric.

Antipneumocystic: Atovaquone.

Antiproliferative agent: Piritrexim Isethionate.

Antiprostatic hypertrophy: Sitogluside.

Antiprotozoal: Amodiaquine; Azanidazole; Banmidazole; Camidazole; Chlortetracycline Bisulfate Chlortetracycline Hydrochloride; Flubendazole; Flunidazole; Halofuginone Hydrobromide; Imidocarb Hydrochloride; Ipronidazole; Misonidazole; Moxnidazole; Nitarsone; Ronidazole; Sulnidazole; and Tinidazole.

Antipruritic: Methdilazine; Methdilazine Hydrochloride; and Trimeprazine Tartrate.

Antipsoriatic: Acitretin; Anthralin; Azaribine; Calcipotriene; Cycloheximide; Enazadrem Phosphate; Etretinate; Liarozole Fumarate; Lonapalene; and Tepoxalin.

Antipsychotic: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; and Ziprasidone Hydrochloride.

Antirheumatic: Auranofin; Aurothioglucose; Bindarit; Lobenzarit Sodium; Phenylbutazone; Pirazolac; Prinomide Tromethamine; and Seprilose.

Antischistosomal: Becanthone Hydrochloride; Hycanthone; Lucanthone Hydrochloride; Niridazole; Oxamniquine; Pararosaniline Pamoate; and Teroxalene Hydrochloride.

Antiseborrheic: Chloroxine; Piroctone; Piroctone Olamine; and Resorcinol Monoacetate.

Antisecretory: Arbaprostil; Deprostil; Fenoctimine Sulfate; Octreotide; Octreotide Acetate; Omeprazole Sodium; Rioprostil; Trimoprostil.

Antispasmodic: Stilonium Iodide; Tizanidine Hydrochloride.

Antithrombotic: Anagrelide Hydrochloride; Dalteparin Sodium; Danaparoid Sodium; Dazoxiben Hydrochloride; Efegatran Sulfate; Enoxaparin Sodium; Ifetroban; Ifetroban Sodium; and Trifenagrel.

Antitussive: Benzonatate; Butamirate Citrate; Chlophedianol Hydrochloride; Codeine Polistirex; Codoxime; Dextromethorphan; Dextromethorphan Hydrobromide; Dextromethorphan Polistirex; Ethyl Dibunate; Guaiapate; Hydrocodone Bitartrate; Hydrocodone Polistirex; Levopropoxyphene Napsylate; Noscapine; Pemerid Nitrate; Pipazethate; and Suxemerid Sulfate.

Anti-ulcerative: Aceglutamide Aluminum; Cadexomer Iodine; Cetraxate Hydrochloride; Enisoprost; Isotiquimide; Lansoprazole; Lavoltidine Succinate; Misoprostol; Nizatidine; Nolinium Bromide; Pantoprazole; Pifarnine; Pirenzepine Hydrochloride; Rabeprazole Sodium; Remiprostol; Roxatidine Acetate Hydrochloride; Sucralfate; Sucrosofate Potassium; and Tolimidone.

Anti-urolithic: Cysteamine; Cysteamine Hydrochloride; and Tricitrates.

Antiviral: Acemannan; Acvclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Appetite suppressant: Dexfenfluramine Hydrochloride; Phendimetrazine Tartrate; and Phentermine Hydrochloride.

Benign prostatic hyperplasia therapy agent: Tamsulosin Hydrochloride.

Blood glucose regulators: Acetohexamide and Glipizide; Chloropropamide; and Human insulin.

Bone resorption inhibitor: Alendronate Sodium; Etidronate Disodium; and Pamidronate Disodium.

Bronchodilator: Albuterol; Albuterol Sulfate; Azanator Maleate; Bamifylline Hydrochloride; Bitolterol Mesylate; Butaprost; Carbuterol Hydrochloride; Clorprenaline Hydrochloride; Colterol Mesylate; Doxaprost; Doxofylline; Dyphylline; Enprofylline; Ephedrine; Ephedrine Hydrochloride; Fenoterol; Fenprinast Hydrochloride; Guaithylline; Hexoprenaline Sulfate; Hoquizil Hydrochloride; Ipratropium Bromide; Isoetharine; Isoetharine Hydrochloride; Isoetharine Mesylate; Isoproterenol Hydrochloride; Isoproterenol Sulfate; Metaproterenol Polistirex; Metaproterenol Sulfate; Nisbuterol Mesylate; Oxtriphylline; Picumeterol Fumarate; Piquizil Hydrochloride; Pirbuterol Acetate; Pirbuterol Hydrochloride; Procaterol Hydrochloride; Pseudoephedrine Sulfate; Quazodine; Quinterenol Sulfate; Racepinephrine; Racepinephrine Hydrochloride; Reproterol Hydrochloride; Rimiterol Hydrobromide; Salmeterol; Salmeterol Xinafoate; Soterenol Hydrochloride; Sulfonterol Hydrochloride; Suloxifen Oxalate; Terbutaline Sulfate; Theophylline; Xanoxate Sodium; Zindotrine; and Zinterol Hydrochloride.

Carbonic anhydrase inhibitor: Acetazolamide; Acetazolamide Sodium; Dichlorophenamide; Dorzolamide Hydrochloride; Methazolamide; and Sezolamide Hydrochloride.

Cardiac depressant: Acecainide Hydrochloride; Acetylcholine Chloride; Actisomide; Adenosine; Amiodarone; Aprindine; Aprindine Hydrochloride; Artilide Fumarate; Azimilide Dihydrochloride; Bidisomide; Bucainide Maleate; Bucromarone; Capobenate Sodium; Capobenic Acid; Cifenline; Cifenline Succinate; Clofilium Phosphate; Disobutamide; Disopyramide; Disopyramide Phosphate; Dofetilide; Drobuline; Edifolone Acetate; Emilium Tosylate; Encainide Hydrochloride; Flecainide Acetate; Ibutilide Fumarate; Indecainide Hydrochloride; Ipazilide Fumarate; Lorajmine Hydrochloride; Lorcainide Hydrochloride; Meobentine Sulfate; Mexiletine Hydrochloride; Modecainide; Moricizine; Oxiramide; Pirmenol Hydrochloride; Pirolazamide; Pranolium Chloride; Procainamide Hydrochloride; Propafenone Hydrochloride; Pyrinoline; Quindonium Bromide; Quinidine Gluconate; Quinidine Sulfate; Recainam Hydrochloride; Recainam Tosylate; Risotilide Hydrochloride; Ropitoin Hydrochloride; Sematilide Hydrochloride; Suricainide Maleate; Tocainide; Tocainide Hydrochloride; and Transcainide.

Cardioprotectant: Dexrazoxane; and Draflazine.

Cardiotonic agent: Actodigin; Amrinone; Bemoradan; Butopamine; Carbazeran; Carsatrin Succinate; Deslanoside; Digitalis; Digitoxin; Digoxin; Dobutamine; Dobutamine Hydrochloride; Dobutamine Lactobionate; Dobutamine Tartrate; Enoximone; Imazodan Hydrochloride; Indolidan; Isomazole Hydrochloride; Levdobutamine Lactobionate; Lixazinone Sulfate; Medorinone; Milrinone; Pelrinone Hydrochloride; Pimobendan; Piroximone; Prinoxodan; Proscillaridin; Quazinone; Tazolol Hydrochloride; and Vesnarinone.

Cardiovascular agent: Dopexamine; and Dopexamine Hydrochloride.

Cerebral ischemia agent: Dextrorphan Hydrochloride.

Choleretic: Dehydrocholic Acid; Fencibutirol; Hymecromone; Piprozolin; Sincalide; Tocamphyl.

Cholinergic: Aceclidine; Bethanechol Chloride; Carbachol; Demecarium Bromide; Dexpanthenol; Echothiophate Iodide; Isoflurophate; Methacholine Chloride; Neostiamine Methylsulfate; Neostigmine Bromide; Physostigmine; Physostigmine Salicylate; Physostigmine Sulfate; Pilocarpine Nitrate; and Pyridostigmine Bromide.

Cholinergic agonist: Xanomeline; and Xanomeline Tartrate.

Cholinesterase Deactivator: Obidoxime Chloride; Pralidoxime Chloride; Pralidoxime Iodide; and Pralidoxime Mesylate.

Coccidiostat: Arprinocid; Narasin; Semduramicin; and Semduramicin Sodium.

Cognition adjuvant: Ergoloid Mesylates; Piracetam; Pramiracetam Hydrochloride; Pramiracetam Sulfate; and Tacrine Hydrochloride.

Cognition enhancer: Besipirdine Hydrochloride; Linopirdine; and Sibopirdine.

Contrast Media: Barium Sulfate; Diatrizoate Sodium; Erythrosine Sodium; Iopanoic Acid; Ipodate Calcium; Metyrapone; and Tyropanoate Sodium.

Diagnostic aid: Aminohippurate Sodium; Anazolene Sodium; Arclofenin; Bentiromide; Benzylpenicilloyl Polylysine; Butedronate Tetrasodium; Butilfenin; Coccidioidin; Corticorelin Ovine Triflutate; Corticotropin Zinc Hydroxide; Corticotropin, Repository; Diatrizoate Meglumine; Diatrizoic Acid; Diphtheria Toxin for Schick Test; Disofenin; Ethiodized Oil; Etifenin; Exametazime; Ferristenc; Ferumoxides; Ferumoxsil; Fluorescein; Fluorescein Sodium; Gadobenate Dimeglumine; Gadodiamide; Gadopentetate Dimegiumine; Gadoteridol; Gadoversetamide; Histoplasmin; Impromidine Hydrochloride; Indigotindisulfonate Sodium; Indocyanine Green; Iobenguane Sulfate I 123; Iobenzamic Acid; Iocarmate Meglumine; Iocarmic Acid; Iocetamic Acid; Iodamide; Iodamide Megiumine; Iodipamide Meglumine; Iodixanol; Iodoxamate Meglumine; Iodoxamic Acid; Ioglicic Acid; Ioglucol; Ioglucomide; Ioglycamic Acid; Iogulamide; Iohexol; Iomeprol; Iopamidol; Iopentol; Iophendylate; Ioprocemic Acid; Iopronic Acid; Iopydol; Iopydone; Iosefamic Acid; Ioseric Acid; Iosulamide Meglumine; Iosumetic Acid; Iotasul; Iotetric Acid; Iothalamate Meglumine; Iothalamate Sodium; Iothalamic Acid; Iotrolan; Iotroxic Acid; Ioversol; Ioxagiate Sodium; Ioxaglate Meglumine; Ioxaglic Acid; Ioxilan; Ioxotrizoic Acid; Ipodate Sodium; Iprofenin; Isosulfan Blue; Leukocyte Typing Serum; Lidofenin; Mebrofenin; Meglumine; Metrizamide; Metrizoate Sodium; Metyrapone Tartrate; Mumps Skin Test Antigen; Pentetic Acid; Propyliodone; Quinaldine Blue; Schick Test Control; Sermorelin Acetate; Sodium Iodide I 123; Sprodiamide; Stannous Pyrophosphate; Stannous Sulfur Colloid; Succimer; Teriparatide Acetate; Tetrofosmin; Tolbutamide Sodium; Tuberculin; and Xylose.

Diuretic: Ambuphylline; Ambuside; Amiloride Hydrochloride; Azolimine; Azosemide; Brocrinat; Bumetanide; Chlorothiazide; Chlorthalidone; Clazolimine; Clorexolone; Ethacrynate Sodium; Ethacrynic Acid; Etozolin; Fenquizone; Furosemide; Hydrochlorothiazide; Isosorbide; Mannitol Mefru side; Ozolinone; Piretanide; Spiroxasone; Torsemide; Triamterene; Triflocin; and Urea.

Dopaminergic agent: Ibopamine.

Ectoparasiticide: Nifluridide; Permethrin.

Emetic: Apomorphine Hydrochloride.

Enzyme inhibitor: 30 Polignate Sodium; Acetohydroxamic Acid; Alrestatin Sodium; Aprotinin; Benazepril Hydrochloride; Benazeprilat; Benurestat; Bromocriptine; Bromocriptine Mesylate; Cilastatin Sodium; Flurofamide;

Lergotrile; Lergotrile Mesylate; Levcycloserine; Libenzapril; Pentopril; Pepstatin; Perindopril; Sodium Amylosulfate; Sorbinil; Spirapril Hydrochloride; Spiraprilat; Taleranol; Teprotide; Tolfamide; and Zofenopril Calcium.

Estrogen: Chlorotrianisene; Dienestrol; Diethylstilbestrol; Diethylstilbestrol Diphosphate; Equilin; Estradiol; Estradiol Cypionate; Estradiol Enanthate; Estradiol Undecylate; Estradiol Valerate; Estrazinol Hydrobromide; Estriol; Estrofurate; Estrogens, Conjugated; Estrogens, Esterified; Estrone; Estropipate; Ethinyl Estradiol; Fenestrel; Mestranol; Nylestriol; and Quinestrol.

Fibrinolytic: Anistreplase; Bisobrin Lactate; and Brinolase.

Free oxygen radical scavenger: Pegorgotein.

Gastric Acid Suppressant: Lansoprazole, Pantoprazole and Omeprazole.

Gastrointestinal Motility agents: Cisapride.

Glucocorticoid: Amcinonide; Beclomethasone Dipropionate; Betamethasone; Betamethasone Acetate; Betamethasone Benzoate; Betamethasone Dipropionate; Betamethasone Sodium Phosphate; Betamethasone Valerate; Carbenoxolone Sodium; Clocortolone Acetate; Clocortolone Pivalate; Cloprednol; Corticotropin; Cortisone Acetate; Cortivazol; Descinolone Acetonide; Dexamethasone; Dexamethasone Sodium Phosphate; Diflucortolone; Diflucortolone Pivalate; Flucloronide; Flumethasone; Flumethasone Pivalate; Flunisolide; Fluocinolone Acetonide; Fluocinonide; Fluocortolone; Fluocortolone Caprocate; Fluorometholone; Fluperolone Acetate; Fluprednisolone; Fluprednisolone Valerate; Flurandrenolide; Formocortal; Hydrocortisone; Hydrocortisone Acetate; Hydrocortisone Buteprate; Hydrocortisone Butyrate; Hydrocortisone Sodium Phosphate; Hydrocortisone Sodium Succinate; Hydrocortisone Valerate; Medrysone; Methylprednisolone Acetate; Methylprednisolone Sodium Phosphate; Methylprednisolone Sodium Succinate; Nivazol; Paramethasone Acetate; Predincarbate; Prednisolone; Prednisolone Acetate; Prednisolone Hemisuccinate; Prednisolone Sodium Succinate; Prednisolone Tebutate; Prednisone; Prednival; Ticabesone Propionate; Tralonide; Triamcinolone; Triamcinolone Acetonide; Triamcinolone Acetonide Sodium; Triamcinolone Diacetate; and Triamcinolone Hexacetonide.

Gonad-stimulating principle: Buserelin Acetate; Clomiphene Citrate; Ganirelix Acetate; Gonadorelin Acetate; Gonadorelin Hydrochloride; Gonadotropin, Chorionic; and Menotropins.

Hormone: 17 Alpha Dihydroequilenin; 17 Alpha Dihydroequilin; 17 Alpha Estradiol; 17 Beta Estradiol; 17 Hydroxy Progesterone; Androstenedione; Clomiphene; Cosyntropin; Dehydroepiandrosterone; Dihydroestosterone; Equilenin; Ethyndiol; Follicle Regulatory Protein; Follicle Stimulating Hormone; Folliculostatin; Gonadoctrinins; Gonadorelin; Gonadotropins; Han Memopausal Gonadotropins; Human Chorionic Gonadotropin; Insulin Growth Factor; Leuprolide; Levonorgestrel; Luteinizing hormone; Luteinizing Hormone Releasing Hormone and Analogs; Medroxyprogesterone; Megestrol; Metogest; Norethindrone; Norethynodrel; Norgestrel; Oocyte Maturation Inhibitor; Oxytocin; Pituitary, Posterior; Progesterone; Relaxin; Seractide Acetate; Somalapor; Somatrem; Somatropin; Somenopor; Somidobove; Tamoxifen; Urofollitropin; and Vasopressin.

Hypocholesterolemic: Lifibrol.

Hypoglycemic: Darglitazone Sodium; and Glimepiride.

Hypolipidemic: Azalanstat Dihydrochloride; Colestolone; Surfomer; and Xenalipin.

Hypotensive: Viprostol.

Immunizing agent: Antirabies Serum; Antivenin; Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; Rho(D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Vaccinia Immune Globulin; VaricellaZoster Immune Globulin; and Yellow Fever vaccine.

Immunomodulator: Dimepranol Acedoben; Imiquimod; Interferon Beta-Ib; Lisofylline; Mycophenolate Mofetil; and Prezatide Copper Acetate.

Immunoregulator: Azarole; Fanetizole Mesylate; Frentizole; Oxamisole Hydrochloride; Ristianol Phosphate; Thymopentin; and Tilomisole.

Immunostimulant: Loxoribine; and Teceleukin.

Immunosuppressant: Azathioprine; Azathioprine Sodium; Cyclosporine; Daltroban; Gusperimus Trihydrochloride; Sirolimus; Tacrolimus.

Impotence therapy adjunct: Delequamine Hydrochloride.

Inhibitor: Acarbose; Atorvastatin Calcium; Benserazide; Brocresine; Carbidopa; Clavulanate Potassium; Dazmegrel; Docebenone; Epoprostenol; Epoprostenol Sodium; Epristeride; Finasteride; Flurbiprofen Sodium; Furegrelate Sodium; Lufironil; Miglitol; Orlistat; Pimagedine Hydrochloride; Pirmagrel; Ponalrestat; Ridogrel; Sulbactam Benzathine; Sulbactam Pivoxil; Sulbactam Sodium; Suronacrine Maleate; Tazobactam; Tazobactam Sodium; Ticlopidine Hydrochloride; Tirilazad Mesylate; Tolrestat; Velnacrine Maleate; Zifrosilone; and Zileuton.

Keratolytic: Alcloxa; Aldioxa; Dibenzothiophene; Etarotene; Motretinide-I Picotrin Diolamine; Salicylic Acid; Sumarotene; Tazarotene; Tetroquinone; and Tretinoin.

LHRH agonist: Deslorelin; Goserelin; Histrelin; Lutrelin Acetate; and Nafarelin Acetate.

Liver disorder treatment: Malotilate.

Luteolysin: Fenprostalene.

Memory adjuvant: Dimoxamine Hydrochloride; and Ribaminol.

Mental performance enhancer: Aniracetam.

Mood regulator: Fengabine.

Mucolytic: Acetylcysteine; Carbocysteine; and Domiodol.

Mucosal Protective agents: Misoprostol (Cytotec).

Mydriatic: Berefrine.

Nasal decongestant: Nemazoline Hydrochloride; Pseudoephedrine Polistirex.

Neuroleptic: Duoperone Fumarate; and Risperidone.

Neuromuscular blocking agent: Atracurium Besylate; Cisatracurium Besylate; Doxacurium Chloride; Gallamine Triethiodide; Metocurine Iodide; Mivacurium Chloride; Pancuronium Bromide; Pipecuronium Bromide; Rocuronium Bromide; Succinylcholine Chloride; Tubocurarine Chloride; and Vecuronium Bromide.

Neuroprotective: Dizocilpine Maleate.

NMDA antagonist: Selfotel.

Non-hormonal sterol derivative: Pregnenolone Succinate.

Oxytocic: Carboprost; Carboprost Methyl; Carboprost Tromethamine; Dinoprost; Dinoprost Tromethamine; Dinoprostone; Ergonovine Maleate; Meteneprost; Methylergonovine Maleate; and Sparteine Sulfate.

Paget's disease agents: Tiludronate Disodium.

Progestin: Algestone Acetophenide; Amadinone Acetate; Anagestone Acetate; Chlormadinone Acetate; Cingestol; Clogestone Acetate; Clomegestone Acetate; Desogestrel; Dimethisterone; Dydrogesterone; Ethynerone; Ethynodiol Diacetate; Etonogestrel; Flurogestone Acetate; Gestaclone; Gestodene; Gestonorone Caproate; Gestrinone; Haloprogesterone; Hydroxyprogesterone Caproate; Lynestrenol; Medrogestone; Med roxyprogesterone Acetate; Methynodiol Diacetate; Norethindrone Acetate; Norgestimate; Norgestomet; Oxogestone Phenpropionate; Quingestanol Acetate; Quingestrone; and Tigestol.

Prostaglandin: Cloprostenol Sodium; Fluprostenol Sodium; Gemeprost; Prostalene; and Sulprostone.

Prostate growth inhibitor: Pentomone.

Prothyrotropin: Protirelin.

Psychotropic: Minaprine.

Radioactive agent: Fibrinogen I 125; Fludeoxyglucose F 18; Fluorodopa F 18; Insulin I 125; Insulin I 131; Iobenguane I 123; Iodipamide Sodium I 131; Iodoantipyrine I 131; Iodocholesterol I 131; Iodohippurate Sodium I 123; Iodohippurate Sodium I 125; Iodohippurate Sodium I 131; Iodopyracet I 125; Iodopyracet I 131; Iofetamine Hydrochloride I 123; Iomethin I 125; Iomethin I 131; Iothalamate Sodium I 125; Iothalamate Sodium I 131; Iotyrosine I 131; Liothyronine I 125; Liothyronine I 131; Merisoprol Acetate Hg 197; Merisoprol Acetate Hg 203; Merisoprol Hg 197; Selenomethionine Se 75; Technetium Tc 99m Antimony Trisulfide Colloid; Technetium Tc 99m Bicisate; Technetium Tc 99m Disofenin; Technetium Tc 99m Etidronate; Technetium Tc 99m Exametazime; Technetium Tc 99m Furifosmin; Technetium Tc 99m Gluceptate; Technetium Tc 99m Lidofenin; Technetium Tc 99m Mebrofenin; Technetium Tc 99m Medronate; Technetium Tc 99m Medronate Disodium; Technetium Tc 99m Mertiatide; Technetium Tc 99m Oxidronate; Technetium Tc 99m Pentetate; Technetium Tc 99m Pentetate Calcium Trisodium; Technetium Tc 99m Sestamibi; Technetium Tc 99m Siboroxime; Technetium Tc 99m Succimer; Technetium Tc 99m Sulfur Colloid; Technetium Tc 99m Teboroxime; Technetium Tc 99m Tetrofosmin; Technetium Tc 99m Tiatide; Thyroxine I 125; Thyroxine 1131; Tolpovidone 1131; Triolein 1125; and Triolein 1131.

Regulator: Calcifediol; Calcitonin; Calcitriol; Clodronic Acid; Dihydrotachysterol; Etidronic Acid; Oxidronic Acid; Piridronate Sodium; Risedronate Sodium; and Secalciferol.

Relaxant: Adiphenine Hydrochloride; Alcuronium Chloride; Aminophylline; Azumolene Sodium; Baclofen; Benzoctamine Hydrochloride; Carisoprodol; Chlorphenesin Carbamate; Chlorzoxazone; Cinflumide; Cinnamedrine; Clodanolene; Cyclobenzaprine Hydrochloride; Dantrolene; Dantrolene Sodium; Fenalamide; Fenyripol Hydrochloride; Fetoxylate Hydrochloride; Flavoxate Hydrochloride; Fletazepam; Flumetramide; Hexafluorenium Bromide; Isomylamine Hydrochloride; Lorbamate; Mebeverine Hydrochloride; Mesuprine Hydrochloride; Metaxalone; Methixene Hydrochloride; Methocarbamol; Nafomine Malate; Nelezaprine Maleate; Papaverine Hydrochloride; Pipoxolan Hydrochloride; Quinctolate; Ritodrine; Ritodrine Hydrochloride; Rolodine; Theophylline Sodium Glycinate; Thiphenamil Hydrochloride; and Xilobam.

Repartitioninq agent: Cimaterol.

Scabicide: Amitraz; Crotamiton.

Sclerosing agent: Ethanolamine Oleate; Morrhuate Sodium; Tribenoside.

Sedative: Propiomazine.

Sedative-hypnotic: Allobarbital; Alonimid; Alprazolam; Amobarbital Sodium; Bentazepam; Brotizolam; Butabarbital; Butabarbital Sodium; Butalbital; Capuride; Carbocloral; Chloral Betaine; Chloral Hydrate; Chlordiazepoxide Hydrochloride; Cloperidone Hydrochloride; Clorethate; Cyprazepam; Dexclamol Hydrochloride; Diazepam; Dichloralphenazone; Estazolam Ethchlorvynol; Etomidate; Fenobam; Flunitrazepam; Fosazepam; Glutethimide; Halazepam; Lonnetazepam; Mecloqualone; Meprobamate; Methaqualone; Midaflur; Paraldehyde; Pentobarbital; Pentobarbital Sodium; Perlapine; Prazepam; Quazepam; Reclazepam; Roletamide; Secobarbital; Secobarbital Sodium; Suproclone; Tracazolate; Trepipam Maleate; Triazolam; Tricetamide; Triclofos Sodium; Trimetozine; Uldazepam; Zaleplon; Zolazepam Hydrochloride; and Zolpidem Tartrate.

Selective adenosine A1 antagonist: Apaxifylline.

Serotonin antagonist: Altanserin Tartrate; Amesergide; Ketanserin; and Ritanserin.

Serotonin inhibitor: Cinanserin Hydrochloride; Fenclonine; Fonazine Mesylate; and Xylamidine Tosylate.

Serotonin receptor antagonist: Tropanserin Hydrochloride.

Steroid: Dexamethasone Acefurate; and Mometasone Furoate.

Stimulant: Amfonelic Acid; Amphetamine Sulfate; Ampyzine Sulfate; Arbutamine Hydrochloride; Azabon; Caffeine; Ceruletide; Ceruletide Diethylamine; Dazopride Fumarate; Dextroamphetamine; Dextroamphetamine Sulfate; Difluanine Hydrochloride; Dimefline Hydrochloride; Doxapram Hydrochloride; Ethamivan; Etryptamine Acetate; Fenethylline Hydrochloride; Flubanilate Hydrochloride; Flurothyl; Histamine Phosphate; Indriline Hydrochloride; Mefexamide; Methamphetamine Hydrochloride; Methylphenidate Hydrochloride; Pemoline; Pyrovalerone Hydrochloride; Xamoterol; and Xamoterol Fumarate.

Suppressant: Amflutizole; Colchicine; Tazofelone.

Symptomatic multiple sclerosis: Fampridine.

Synergist Proadifen Hydrochloride.

Thyroid hormone: Levothyroxine Sodium; Liothyronine Sodium; and Liotrix.

Thyroid inhibitor: Methimazole; and Propylthiouracil.

Thyromimetic: Thyromedan Hydrochloride.

Tranquilizer: Bromazepam; Buspirone Hydrochloride; Chlordiazepoxide; Clazolam; Clobazam; Clorazepate Dipotassium; Clorazepate Monopotassium; Demoxepam; Dexmedetomidine; Enciprazine Hydrochloride; Gepirone Hydrochloride; Hydroxyphenamate; Hydroxyzine Hydrochloride; Hydroxyzine Pamoate; Ketazolam; Lorazepam; Lorzafone; Loxapine; Loxapine Succinate; Medazepam Hydrochloride; Nabilone; Nisobamate; Oxazepam; Pentabamate; Pirenperone; Ripazepam; Rolipram; Sulazepam; Taciamine Hydrochloride; Temazepam; Triflubazam; Tybamate; and Valnoctamide.

Unstable angina agents: Tirofiban Hydrochloride.

Uricosuric: Benzbromarone; Irtemazole; Probenecid; Sulfinpyrazone.

Vasoconstrictor: Angiotensin Amide; Felypressin; Methysergide; and Methysergide Maleate.

Vasodilator: Alprostadil; Azaclorzine Hydrochloride; Bamethan Sulfate; Bepridil Hydrochloride; Buterizine; Cetiedil Citrate; Chromonar Hydrochloride; Clonitrate; Dipyridamole; Droprenilamine; Erythrityl Tetranitrate; Felodipine; Flunarizine Hydrochloride; Fostedil; Hexobendine; Inositol Niacinate; Iproxamine Hydrochloride; Isosorbide Dinitrate; Isosorbide Mononitrate; Isoxsuprine Hydrochloride; Lidoflazine; Mefenidil; Mefenidil Fumarate; Mibefradil Dihydrochloride; Mioflazine Hydrochloride;

Mixidine; Nafronyl Oxalate; Nicardipine Hydrochloride; Nicergoline; Nicorandil; Nicotinyl Alcohol; Nimodipine; Nisoldipine; Oxfenicine; Oxprenolol Hydrochloride; Pentaerythritol Tetranitrate; Pentoxifylline; Pentrinitrol; Perhexiline Maleate; Pindolol; Pirsidomine; Prenylamine; Propatyl Nitrate; Suloctidil; Terodiline Hydrochloride; Tipropidil Hydrochloride; Tolazoline Hydrochloride; and Xanthinol Niacinate.

Wound healing agent: Ersofermin.

Xanthine oxidase inhibitor: Allopurinol; and Oxypurinol.

Other exemplary small molecules include: 16-Alpha Fluoroestradiol; 16Alpha-Gitoxin; 16-Eplestriol; 17 Alpha Estradiol; 17Beta Estradiol; IAlpha-Hydroxyvitamin D2; 1-Decpyrrolidinone; 1-Dodecpyrrolidinone; 22-Oxacalcitriol; 2CVV; 2'-Nor-cGMP; 3-Isobutyl GABA; 6-FUDCA; 7-Methoxytacrine; Abacavir Sulfate; Abanoquil; Abecarnil; Acadesine; Acamprosate; Acebutolol Hydrochloride; Aceclofenac; Acetomepregenol; Acetrizoate Sodium; Acetylcysteine, N-; Acetyldigitoxin; Acetyl-L-carnitine; Acetylmethadol; Acipimox; Acitemate; Aclatonium; Aconiazide; Acrivastinet; Adafenoxate; Adatanserin; Adefovir Dipivoxil; Adelmidrol; Ademetionine; Adiposin; Adrafinil; Alacepril; Aladapcin; Alaptide; Alatrofloxacin Mesylate; Albolabrin; Albumin Chromated Cr-51 Serum; Albumin Human; Albumin Iodinated I-125 Serum; Albumin Iodinated 1-131 Serum; Aldecalmycin; Alendronic Acid; Alentemol; Alfacalcidol; Alfuzosin; Alglucerase; Alinastine; Alitretinoin; Alkavervir; Allopurinol Sodium; Almotriptan Malate; Alosetron; Alpha Idosone; Alpha-Tocopherol; Alpha-Tocopherol Acetate; Alseroxylon; Altromycin B; Amantadine-HCl; Ambenonium Chloride; Amelometasone; Amezinium Metilsulfate; Amfebutamone; Amifloxacin; Aminolevulinic Acid Hydrochloride; Aminosalicylic Acid Resin Complex; Amiodarone Hydrochloride; Amisulpride; Amlodipine; Ammonium Lactate; Amphetamine Adipate; Amphetamine Aspartate; Amphetamine Resin Complex; Ampiroxicam; Amprenavir; Amylin; Amythiamicin; Ananain; Anaritide; Anileridine Phosphate; Anisindione; Anordrin; Apadoline; Apafant; Apraclonidine; Aprepitant; Aprosulate Sodium; Aprotinin Bovine; Aptiganel; Aranidipine; Arbekacin; Arbidol; Arbutamine; Arecatannin B 1; Argatroban; Aripiprazol; Aripiprazole; Arotinolol; Articaine Hydrochloride; Ascorbic Acid; Asimadoline; Aspalatone; Asperfuran; Aspoxicillin; Atazanavir Sulfate; Atenolol, S-; Atevirdine; Atomoxetine Hydrochloride; Atpenin B; Atrinositol; Aureobasidin A; Avobenzone; Azadirachtine; Azelaic Acid; Azelastine; Azelnidipine; Azimilide; Azithromycin Dihydrate; Aztreonwn; Baccatin III; Bacoside A; Bacoside B; Bactobolamine; Balazipone; Balhimycin; Balofloxacin; Balsalazide; Bambuterol; Baohuoside 1; Barnidipine; Batebulast; Beauvericin; Becaplermin; Becliconazole; Beclomethasone Dipropionate Monohydrate; Befloxatone; Bellenamine; Benflumetol; Benidipine; Bentoquatam; Benzisoxazole; Benzoidazoxan; Benzoyl Peroxide; Benzphetamine Hydrochloride; Benzquinamide Hydrochloride; Benztropine; Benzyl Benzoate; Benzyl Penicilloyl-Polylysine; Bepridil; Beractant; Beraprost; Berlafenone; Bertosamil; Besipirdine; Beta-Carotene; Betaine, Anhydrous; Betamipron; Betaxolol; Betazole Hydrochloride; Bevantolol; Bexarotene; Bifemelane; Bimakalim; Bimatoprost; Bimithil; Binospirone; Biotin; Bioxalomycin Alpha2; Biriperone; Bisaramil; Bisaziridinylspermine; Bis-Benzimidazole A; Bis-Benzimidazole B; Bismuth Subsalicylate; Bistramide D; Bistramide K; Boldine; Bopindolol; Bortezomib; Brefeldin; Brimonidine; Brinzolamide; Bromfenac; Bucindolol; Budipine; Bunazosin; Butenafine; Butenafine Hydrochloride; Butixocort Propionate; Cabergoline; Caffeine Citrate; Calanolide A; Calcitonin Human; Calcitonin, Salmon; Calcium; Calcium Acetate; Calcium Gluceptate; Calcium Metrizoate; Calfactant; Camonagrel; Candesartan; Candesartan Cilexetil; Candoxatrilat; Capromab; Capsaicin; Carbarnazepine; Carbazomycin C; Carbetocin; Carbidopa/Levodopa; Carbovir; Carboxymethylated Beta-I,3-Glucan; Carperitide; Carteolol; Carumonam; Carvotroline; Caspofungin Acetate; Cebaracetam; CefadroxillCefadroxil Hemihydrate; Cefcapene Pivoxil; Cefdaloxime Pentexil Tosilate; Cefditoren Pivoxil; Cefepime Hydrochloride (Arginine Formulation); Cefetamet; Cefetamet Pivoxil; Cefffietazole; Cefluprenam; Cefminox; Cefodizime; Cefoselis; Cefotiam; Cefotiam Hexetil; Cefozopran; Cefpirome; Cefsulodin; Ceftazidime (Arginine Formulation); Ceftazidime Sodium; Cefteram; Ceftibuten Dihydrate; Ceftriaxone; Celastrol; Celecoxib; Celikalim; Celiprolol; Cellulose Sodium Phosphate; Cepacidine A; Cericlamine; Cerivastatin; Cerivastatin Sodium; Certoparin Sodium; Cetiedil; Cetirizine; Cetyl Alcohol; Cevimeline Hydrochloride; Chlormerodrin, Hg-197; Chlormezanone; Chloroorienticin A; Chloroorienticin B; Cholecalciferol; Cholestyramine; Choriogonadotropin Alfa; Chromic Phosphate, P-32; Chymopapain; Chymotrypsin; Cibenzoline; Ciclesonide; Cicloprolol; Cilansetron; Cilnidipine; Cilobradine; Cilostazol; Cimetropium Bromide; Cinitapride; Cinolazepam; Ciprostene; Cisapride Monohydrate; Cisatracurium, Besilate; Cistinexine; Citalopram; Citalopram Hydrobromide; Citicoline; Citreamicin Alpha; Clausenamide; Clidinium Bromide; Clinafloxacin; Clomethiazole; Clopidogrel; Clopidogrel Bisulfate; Cobalt Chloride, Co-57; Cobalt Chloride, Co-60; Colesevelam Hydrochloride; Colestimide; Colfosceril Palmitate; Complestatin; Contignasterol; Contortrostatin; CorticotropinZinc Hydroxide; Cosalane; Costatolide; Cotinine; Cournermycin AI; Cryptenamine Acetates; Cryptenamine Tannates; Cucumariosid; Curdlan Sulfate; Curiosin; Cyanocobalamin; Cyanocobalamin, Co-57; Cyanocobalamin, Co-58; Cyanocobalamin, Co-60; Cyclazosin; Cyclic HPMPC; Cyclobenzaprine; Cyclobut A; Cyclobut G; Cyclocapron; Cyclosin; Cyclothialidine; Cyclothiazomycin; Cycrimine Hydrochloride; Cyproterone; Cysteamine Bitartrate; Cytochalasin B; Dactimicin; Daidzein; Daidzin; Danaparoid; Daphnodorin A; Dapiprazole; Dapitant; Darifenacin; Darlucin A; Darsidomine; Daunorubicin Citrate; DdUTP; Decamethonium Bromide; Deferiprone; Deferoxamine Mesylate; Dehydrodidemnin B; Delapril; Delequarnine; Delfaprazine; Delmopinol; Delphinidin; Deoxypyridinoline; Deprodone; Depsidomycinderamciclane; Dermatan Sulfate; Deserpidine; Desirudin; Desloratadine; Desmopressin; Desoxoamiodarone; Desoxyribonuclease; Detajrnium Bitartrate; Dexketoprofen; Dexloxiglumide; Dexmethylphenidate Hydrochloride; Dexrazoxane Hydrochloride; Dexsotalol; Dextrin 2-Sulphate; Dextroamphetamine Adipate; Dextroamphetamine Resin Complex; Dextroamphetamine Saccharate; Dextrose; Diclofenac Digolil; Dicranin; Dienogest; Diethylhomospennine; Diethylnorspermine; Difenoxin Hydrochloride; Dihydrexidine; Diltiazeim; Dimethyl Prostaglandin Al; Dimethylhomospermine; Dimiracetam; Dimyristoyl Lecithin; Diphemanil Methylsulfate; Diphencyprone; Diphenylpyraline Hydrochloride; Diprafenone; Dipropylnorspermine; Discodermolide; Divalproex; Docarpamine; Docosanol, 1-; Dolasetron Mesylate Monohydrate; Domitroban; Donepezil Hydrochloride; Dorzolamide; Dosmalfate; Dotarizine; Doxazosin; Doxercalciferol; Draculin; Drosperidone; Drospirenone; Drotaverine Acephyllinate; Droxicam; Dutasteride; Ebiratide; Ebrotidine; Ecabapide; Ecabet; Ecdisteron; Echicetin; Echistatin; Ecteinascidin 722; Ecteinascidin 729; Ecteinascidin 743;

Edaravone; Edetate Calcium Disodium; Edetate Disodium; Edobacomab; Edrecolomab; Efavirenz; Efegatran; Efonidipine; Egualen; Elcatonin; Eletriptan; Eletriptan Hydrobromide; Elgodipine; Eliprodil; Eltenac; Emakalim; Emedastine; Emedastine Difumarate; Emiglitate; Emoctakin; Emtricitabine; Enalapril; Enazadrem; Enfuvirtide; Englitazone; Entacapone; Enterostatin; Eplerenone; Epoxymexrenone; Eptastigmine; Eptifibatide; Erdosteine; Ergocalciferol; Ersentilide; Ertapenem Sodium; Erythritol; Escitalopram Oxalate; Esomeprazole Magnesium; Estazolam; Estradiol Acetate; Esuprone; Etanterol; Ethacizin; Ethchlorvynol; Ethinamate; Ethinylestradiol; Ethoxzolamide; Etidocaine Hydrochloride; Etizolam; Etrabamine; Eveminomicin; Examorelin; Ezetimibe; Faerieftmgin; Fantofarone; Famciclovir; Faropenem; Fasidotril; Fasudil; Fedotozine; Felbarnate; Fenofibrate; Fenoldopam; Fenspiride; Fentanyl; Fenticonazole; Fepradinol; Ferpifosate Sodium; Ferristene; Ferrixan; Ferrous Citrate, Fe-59; Fexofenadine Hydrochloride; Fibrinogen, 1-125; Fibrinolysin; Flecainide; Flerobuterol; Flesinoxan; Flezelastine; Flobufen; Flomoxef; Florfenicol; Florifenine; Flornastat; Flosatidil; Fludeoxyglucose, F-18; Flumecinol; Flunarizine; Fluocalcitriol; Fluoxetine, R-; Fluoxetine, S-; Fluparoxan; Flupirtine; Flurbiprofen Axetil; Flurithromycin; Flutamide; Flutrimazole; Fluvastatin; Fluvoxamine; Folic Acid; Follitropin Alfa; Follitropin Alfa/Beta; Fomivirsen Sodium; Fondaparinux Sodium; Forasartan; Formoterol; Formoterol Fumarate; Formoterol, R,R; Fosinopril; Fosphenytoin; Frovatriptan Succinate; Fulvestrant; Furosemide; Gadobenic Acid; Gadobutrol; Gadodiamide-EOB-DTPA; Gadopentetate Dimeglumine; Gadoteric Acid; Galantamine; Galantamine Hydrobromide; Galdansetron; Gallopamil; Gamolenic Acid; Gatifloxacin; Gefitinib; Gemifloxacin Mesylate; Gemtuzumab Ozogamicin; Gepirone; Girisopam; Glaspimod; Glatiramer Acetate; Glaucocalyxin A; Glucagon Hydrochloride; Glucagon Hydrochloride Recombinant; Glucagon Recombinant; Gluconolactone; Glutapyrone; Glutathione Disulfide; Glycopine; Glycopril; Goserelin Acetate; Grepafloxacin; Grepafloxacin Hydrochloride; Guaifenesin; Guanidine Hydrochloride; Halichondrin B; Halofantrine; Halomon; Haloperidol Lactate; Halopredone; Hatomarubigin C; Hatornambigin D; Hatornamicin; Hatornarubigin A; Hatornarubigin B; Heparin Calcium; Heparin Sodium; Hexocyclium Methylsulfate; Hexylcaine Hydrochloride; Histrelin Acetate; Hyaluronidase; Hydrocortamate Hydrochloride; Hydrocortisone Cypionate; Hydrocortisone Probutate; Hydro quinone; Hydroxocobalamin; Hydroxypropyl Cellulose; Hydroxystilbamidine Isethionate; Ibandronate Sodium; Ibogaine; Ibudilast; Ibuprofen Potassium; Icodextrin; Illimaquinone; Iloprost; Imatinib Mesylate; Imidapril; Imidazenil; Imiglucerase; Imipramine Pamoate; Inamrinone Lactate; Indapamide; Indinavir; Indinavir Sulfate; Indium In-III Oxyquinoline; Indium In-III Pentetate Disodium; Indium In-III Pentetreotide Kit; Indometacin; Indometacin Farnesil; Indomethacin Sodium; Inocoterone; Inogatran; Inolimomab; Insulin Aspart; Insulin Aspart Protamine; Insulin Glargine; Insulin Lispro Protamine; Interferon Alfa; Interferon Alfa-NI; Interferon Beta; Interferon Beta-Ial; Interferon Gamma-I A; Interferon Gamma-I B; Interferon Omega; Interferon, Consensus; Interleukin-3; Interleukin-1; Interleukin-I Beta; Interleukin-10; Interleukin-II; Interleukin-12; Interleukin-15; Interleukin-2; Interleukin-4; Interleukin-5; Interleukin-7; Interleukin-8; InterleukinI Alpha; Intrinsic Factor; Inulin; Invert Sugar; Iobenguane Sulfate I 131; Iobitridol; Iodamide Meglumine; Iodipamide Sodium; Iodoamiloride; Iodohippurate Sodium, 1-123; Iodohippurate Sodium, 1-131; Iofetamine Hydrochloride 1-123; Iofratol; Iopromide; Iopyrol; Iorneprol; Iothalamate Sodium, 1-125; Iotriside; Ioxaglate Sodium; Ipazilide; Ipenoxazone; Ipidacrine; Ipomeanol, 4; Ipriflavone; Ipsapirone; Irbesartan; Irloxacin; Iron Dextran; Iron Sucrose; Irternazole; Isalsteine; Isbogrel; Iseparnicin; Isofloxythepin; Isopropyl Unoprostone; Itameline; Itopride; Ketoprofen, R-; Ketoprofen, S-; Ketorolac; Lactitol; Lactivicin; Lactulose; Laennec; Lafutidine; Lanoconazole; Lanperisone; Larnifiban; Larnotrigine; Latanoprost; Lateritin; Laurocaprarn; Leflunomide; Lemefloxacin; Leminoprazole; Lenercept; Lepirudin; Leptin; Lercanidipine; Lerisetron; Lernildipine; Lesopitron; Letrazuril; Leucomyzin; Levalbuterol Hydrochloride; Levallorphan Tartrate; Levamisole Hydrochloride; Levetiracetam; Levobetaxolol; Levobunolol; Levobupivacaine; Levobupivacaine Hydrochloride; Levocabastine; Levocarnitine; Levodropropizine; Levofloxacin; Levopropoxyphene Napsylate, Anhydrous; Levormeloxifene; Levornoprolol; Levosimendan; Levosulpiride; Lindane; Linezolid; Linotroban; Linsidornine; Lintitript; Lintopride; Lipase; Lirexapride; Lithium Carbonate; Lithium Citrate; Lodoxamide; Lomerizine; Lonazolac; Lopinavir; Lorglumide; Losartan; Losigamone; Loteprednol; Loviride; Loxapine Hydrochloride; LpdR; Lubeluzole; Lutetium; Luzindole; Lydicamycin; Lysostaphin; Magainin 2 Arnide; Magnesium Acetate; Magnesium Acetate Tetrahydrate; Magnolol; Malathion; Mallotochromene; Mallotojaponin; Mangafodipir; Mangafodipir Trisodium; Manidipine; Maniwamycin A; Mannitol; Manurnycin E; Manurnycin F; Mapinastine; Martek 8708; Martek 92211; Massetolide; Meglumine Metrizoate; Meloxicam; Melphalan Hydrochloride; Menadiol Sodium Diphosphate; Menadione; Meprednisone; Mequinol; Mersalyl Sodium; Mesna; Metformin Hydrochloride; Methantheline Bromide; Metharbital; Methoxamine Hydrochloride; Methoxatone; Methoxsalen; Methscopolamine Bromide; Methyclothiazide; Methyldopa; Methylhistamine, R-alpha; Methylinosine Monophosphate; Methylprednisolone Aceponate; Methyprylon; Metiparnide; Metipranolol Hydrochloride; Metolazone; Metoprolol Fumarate; Metoprolol, S-; Metoprotol Tartrate; Metrifonate; Metrizoate Magnesium; Metrizoic Acid; Mezlocillin Sodium Monohydrate; Michellarnine B; Microcolin A; Midodrine; Miglustat; Milacernide; Milarneline; Mildronate; Milnacipran; Milrinone Lactate; Miokarnycin; Mipragoside; Mirfentanil; Mivazerol; Mixanpril; Mizolastine; Mizoribine; Moexipril; Moexipril Hydrochloride; Mofezolac; Mometasone; Mometasone Furoate Monohydrate; Monobenzone; Montirelin; Moracizine; Moricizine Hydrochloride; Mosapramine; Mosapride; Motilide; Moxifloxacin Hydrochloride; Moxiraprine; Moxonidine; Mupirocin; Mupirocin Calcium; Mycophenolate Mofetil Hydrochloride; Nadifloxacin; Nadroparin Calcium; Nafadotride; Nafamostat; Naftopidil; Naglivan; Nalmefene Hydrochloride; Naltrexone Hydrochloride; Napadisilate; Napsagatran; Naratriptan; Nasaruplase; Nateglinide; Nateplasel; Nelfinavir Mesylate; Nesiritide; Niacinamide; Nicotine; Nicotine Polacrilex; Niperotidine; Niravoline; Nisin; Nitazoxanide; Nitecapone; Nitisinone; Nitrendipine, S-; Nitrofurantoin Monohydrate; Nitrofurantoin Sodium; Nitrofurantoin, Macrocrystalline; Nitrofurazone; Nitroglycerin; Nonoxynol-9; Norelgestromin; Octyl Methoxycinnamate; Olmesartan Medoxomil; Olopatadine; Olopatadine Hydrochloride; Olprinone; Olsalazine; Omeprazole Magnesium; Ondansetron, R-; Oral Hypogyceremics; Orphenadrine Hydrochloride; Oseltamivir Phosphate; Otenzepad; Oxamisole; Oxaprozin Potassium; Oxcarbazepine; Oxiconazole; Oxiracetam; Oxodipine; Oxybenzone; Oxybutynin; Oxyphencyclimine Hydrochloride; Oxyphenonium Bromide; Ozagrel; Palauarnine; Palinavir; Palonosetron Hydrochloride; Pamaparin Sodium; Panamesine; Pancrelipase; Panipenem; Panipenum; Pannorin; Panornifene; Pantethine; Pantoprazole Sodium; Pantothenic Acid; Paramethadione; Paricalcitol; Parnaqueside; Parnicogrel; Paroxetine Hydrochloride; Paroxetine Mesylate; Parthenolide; Pazufloxacin; Pegademase Bovine; Pegvisomant; Pemirolast; Pemirolast Potassium; Penciclovir Sodium; Penicillamine; Pentafuside; Pentagastrin; Pentamidine; Pentamidine Isethionate; Pentetate Calcium Trisodium Yb-169; Pentigetide; Pentolinium Tartrate; Pentosan; Perflexane; Perfluoropolymethylisopropyl Ether; Perflutren; Pergolide; Pergolide Mesylate; Perindoprilat; Pernedolac; Perospirone; Phenaridine; Phenindione; Pheniramine Maleate; Phenmetrazine Hydrochloride; Phenotoxifvline; Phenserine; Phensuccinal; Phentermine Resin Complex; Phentolamine Mesilate; Phenylalanyl Ketoconazole; Phenylephrine Bitartrate; Phenytoin Sodium, Extended; Phenytoin Sodium, Prompt; Phosphoric Acid; Phytonadione; Picenadol; Picroliv; Picumeterol; Pidotimod; Pilsicainide; Pimagedine; Pimecrolimus; Pimilprost; Pinocebrin; Pioglitazone; Piperonyl Butoxide; Pirlindole; Pirmenol; Pirodornast; Polyestradiol Phosphate; Polyethylene Glycol 3350; Polytetrafluoroethylene; Poractant Alfa; Potassium Chloride; Pramipexole Dihydrochloride; Praziquantel; Prazosin; Prilocaine; Procaine Merethoxylline; Proguanil Hydrochloride; Propagermanium; Propentofylline; Propiolactone; Propiomazine Hydrochloride; Propionylcamitine, L-; Propiram; Propiram+Paracetarnol; Propiverine; Prostratin; Protegrin; Protein Hydrolysate; Protokylol Hydrochloride; Protosufloxacin; Prulifloxacin; Pyrethrins; Pyridoxine; Pyridoxine Hydrochloride; Quazeparn; Quetiapine; Quetiapine Fumarate; Quiflapon; Quinagolide; Quinapril; Quinethazone; Quinidine Polygalacturonate; Raloxifene; Ramatroban; Ranelic Acid; Ranolazine; Rapacuronium Bromide; Recainarn; Regavirumab; Repaglinide; Rescinnamine; Resinferatoxin; Reticulon; Reviparin Sodium; Revizinone; Riboflavin; Riboflavin Phosphate Sodium; Ricasetron; Rilopirox; Rimantadine; Rimexolone; Rimoprogin; Riodipine; Ripisartan; Risedronic Acid; Rispenzepine; Ritipenem Acoxil; Ritipenern; Ritonavir; Rivastigmine Tartrate; Rizatriptan Benzoate; Rnibefradil; Rnivacurium Chloride; Rofecoxib; Rokitamycin; Ropinirole; Ropivacaine; Ropivacaine Hydrochloride Monohydrate; Roquinirnex; Rose Bengal Sodium, 1131; Rosiglitazone Maleate; Roxatidine; Roxindole; Rubidium Chloride Rb-82; Rufloxacin; Rupatidine; Ruzadolane; Sacrosidase; Safflower Oil; Safironil; Salbutamol, R-; Salnacedin, R-; Samarium Sm 153 Lexidronam Pentasodium; Sanfetrinem; Saprisartan; Sapropterin; Saquinavir; Sarcophytol A Sargramostim; Sarneridine; Sarnpatrilat; Sarpogrelate; Saruplase; Saterinone; Satigrel; Satumomab Pendetide; Scopolamine; Secretin; Selenomethionine, Se-75; Sematilide; Sermorelin; Sernotiadil; Sertaconazole; Sertraline; Sertraline-HCl; Setiptiline; Sevelamer Hydrochloride; Sevirurnab; Sezolamide; Sildenafil Citrate; Silipide; Silteplase; Silver Sulfadiazine; Simendan; Simethicone; Simethicone-Cellulose; Sinitrodil; Sinnabidol; Sipatrigine; Sirnvastatin; Somatomedin C; Somatropin Recombinant; Sorbitol; Somatomedin B; Somatrem; Somatropin; Sotalol; Staurosporine; Stepronin; Stobadine; Strontium Chloride, Sr-89; Succibun; Sulfanilamide; Sulfaphenazole; Sulfapyridine; Sulfoxamine; Sulfoxone Sodium; Sulfur; Sultamicillin; Sultopride; Sumatriptan; Sutilains; Symakalim; Talbutal; Tandospirone; Tannic Acid; Tapgen; Taprostene; Tartaric Acid; Tazanolast; Tegaserod Maleate; Telenzepine; Telmesteine; Telmisartan; Temocapril; Tenofovir Disoproxil Fumarate; Tenosal; Tepirindole; Terazosin; Terbinafine Hydrochloride; Terflavoxate; Terguride; Terlipressin; Terodiline; Tertatolol; Testosterone Buciclate; Thallous Chloride, TI-201; Thiamine; Thiamine Hydrochloride; Thiofedrine; Thiomarinol; Thioperamide; Thiosemicarbazone; Thonzonium Bromide; Thyroglobulin; Thyrotropin; Thyrotropin Alfa; Tiagabine; Tiagabine Hydrochloride; Tianeptine; Tiapafant; Ticlopidine; Tienoxolol; Tilisolol; Tilnoprofen Arbamel; Tiludronic Acid; Tiopronin; Tiotropium Bromide; Tirandalydigin; Tirilazad; Tirofiban; Tiropramide; Tocopherol Acetate; Tolterodine Tartrate; Torasemide; Trafennin; Trandolapril; Tranylcypromine Sulfate; Travoprost; Traxanox; Trazodone-HCl; Treprostinil Sodium; Tretinoin Tocoferil; Triarntevene; Tricaprilin; Trichohyalin; Trichosanthin, Alpha; Triclosan; Tridihexethyl Chloride; Trientine; Trientine Hydrochloride; Triflavin; Trimegestone; Trimethoprim Hydrochloride; Trioxsalen; Triptorelin Pamoate; Trolamine Polypeptide Oleate Condensate; Trombodipine; Trometarnol; Tromethamine; Tropine Ester; Trospectomycin; Trovafloxacin; Trovafloxacin Mesylate; Trovirdine; Tucaresol; Tulobuterol; Tylogenin; Tyloxapol; Undecoylium Chloride; Undecoylium Chloride Iodine Complex; Unoprostone Isopropyl; Urapidil; Urea, C-13; Urea, C-14; Uridine Triphosphate; Valaciclovir; Valdecoxib; Valganciclovir Hydrochloride; Valproate Magnesium; Valproate Semisodium; Valrubicin; Valsartan; Vamicamide; Vanadeine; Vaninolol; Vasopressin Tannate; Venlafaxine; Verapamil, (S); Veratrum Viride; Veroxan; Vexibinol; Vinburnine Citrate; Vinburnine Resinate; Vinconate; Vinpocetine; Vinpocetine Citrate; Vintoperol; Viomycin Sulfate; Vitamin A; Vitamin A Palmitate; Vitamin E; Vitamin K; Voriconazole; Voxergolide; Warfarin Potassium; Xemilofiban; Ximoprofen; Yangarnbin; Zabicipril; Zacopride; Zacopride, R-; Zafirlukast; Zalospirone; Zaltoprofen; Zanamivir; Zanarnivir; Zankiren; Zatebradine; Zatosetron; Zenarestat; Zinostatin Stimalarner; Ziprasidone; Ziprasidone Mesylate; Zoledronic Acid; Zolmitriptan; Zolpidem; Zopiclone; Zopiclone, S-; Zopolrestat; and Zotepine.

In some embodiments, the therapeutic agent is one for delivery across the BBB or the BCSFB, such as a chemotherapeutic agent (e.g., Mechlorethamine hydrochloride, Cyclophosphamide, Ifosfamide, Chlorambucil, Melphalan, Busulfan, Thiotepa (Triethylenethiophosphoramide), Carmustine, Lomustine, Streptozocin, Vincristine, Vinblastine, Paclitaxel, Methotrexate, Mercaptopurine, Thioguanine, Fluorouracil, Cytarabine, Azacitidine, Dactinomycin, Doxorubicin, Daunorubicin, Idarubicin, Bleomycin, Picamycin, Mitomycin, Hydroxyurea, Procarbazine, Dacarbazine, Cisplatin, Carboplatin, Asparaginase, Etoposide, Amsarcrine, Mitotane, or Mitoxantrone). Other therapeutic agents of interest for delivery across the BBB or BCSFB include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines (H1-antagonists, H2-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Myleran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. Other exemplary agents are described in US Patent Publication Number US20100183581, which is incorporated herein by reference with regard to active agents described therein.

Other exemplary therapeutic agents for delivery across the BBB or BCSFB include, but are not limited to, azidothymidine, nido-carborane, methotrexate, recombinant human soluble CD4, vasoactive intestinal peptide analog, nerve growth factor, β-amyloid peptide Aβ, brain-derived neurotrophic factor, human epidermal growth factor, basic fibroblast growth factor, daunomycin, expression plasmid encoding tyrosine hydroxylase, PNA antisense to rev gene of HIV-1, PNA antisense to huntingtin gene, expression plasmid encoding antisense mRNA to human EGFR, brain-derived neurotrophic factor, Adriamycin, dalargin, doxorubicin, loperamide, 5-fluorouracil, and loperamide.

The diagnostic agent may be any diagnostic agent known in the art or described herein. The diagnostic agent may be any agent suitable for diagnostic detection, e.g., Magnetic Resonance Imaging (MRI), Positron Emission Tomography (PET), ultrasound imaging, optical imaging, sonoluminescence imaging, photoacoustic imaging, or nuclear imaging. Non-limiting, exemplary diagnostic agents include an enzyme, a fluorescent compound, a radioactive compound, an ultrasound contrast agent, an optical dye, or a paramagnetic metal atom. Exemplary, non-limiting radioactive compounds comprise a radionuclide selected from the group consisting of: $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{51}$Cr, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{188}$Re, $^{203}$Pb, $^{211}$Bi, $^{212}$Bi, $^{213}$Bi, $^{214}$Bi, $^{105}$Rh, $^{109}$Pd, $^{117m}$Sn, $^{149}$Pm, $^{161}$Tb, $^{177}$Lu, $^{198}$Au and $^{199}$Au. Exemplary, non-limiting fluorescent compounds include fluorescein isothiocyanate (FITC), rhodamine (tetramethyl rhodamine isothiocyanate, TRITC), GFP, RFP, YFP, BFP, and quantum dots, and variants thereof. Exemplary, non-limiting enzymes include horseradish peroxidase. Exemplary non-limiting optical dyes include those described in WO 98/18497, WO 98/18496, WO 98/18495, WO 98/18498, WO 98/53857, WO 96/17628, WO 97/18841, WO 96/23524, and WO 98/47538. Exemplary, non-limiting paramagnetic metal atoms include $Mn^{2+}$, $Cu^{2+}$, $Fe^{2+}$, $Co^{2+}$, $Ni^{2+}$, $Gd^{3+}$, $Eu^{3+}$, $Dy^{3+}$, $Pr^{3+}$, $Cr^{3+}$, $Co^{3+}$, $Fe^{3+}$, $Ti^{3+}$, $Tb^{3+}$, $Nd^{3+}$, $Sm^{3+}$, $Ho^{3+}$, $Er^{3+}$, $Pa^{4+}$ and $Eu^{2+}$. Exemplary, non-limiting ultrasound contrast agents include those that comprise a fluorinated gas selected from the group of: $SF_6$ freons, $CF_4$, $C_2F_6$, $C_3F_8$, $C_4F_{10}$, $CBrF_3$, $CCl_2F_2$, $C_2ClF_5$, $CBrClF_2$ and perfluorocarbons.

In some embodiments, the therapeutic or diagnostic agent is conjugated or fused to the ligand, optionally via a linker. The therapeutic or diagnostic agent may be conjugated or fused to the ligand using any method known in the art or described herein. The therapeutic or diagnostic agent may be fused to the ligand, e.g., by obtaining a nucleic acid that encodes the ligand in frame with a nucleic acid that encodes the therapeutic or diagnostic agent, generating a fusion protein comprising the ligand and the therapeutic or diagnostic agent. The therapeutic or diagnostic agent may be fused to the N-terminus or the C-terminus of the ligand. The therapeutic or diagnostic agent may be conjugated to the ligand by covalent bonding, e.g., via a disulfide bond to a cysteine in the ligand.

In some embodiments, the therapeutic or diagnostic agent is contained within a nanoparticle, such as a liposome, which may be conjugated to the ligand. Any suitable nanoparticle (e.g., a liposome, micelle, polymeric nanoparticle, or other nanoparticle) can be used, for example, to deliver a therapeutic or diagnostic agent. In some embodiments, a nanoparticle (e.g., containing or cojungated to a therapeutic or diagnostic agent) can be conjugated to a ligand (e.g., in order to target the nanoparticle to a cell expressing a receptor for the ligand). A ligand can be conjugated (e.g., covalently or non-covalently) to a nanoparticle either directly or via a linker. In some embodiments, more than one ligand molecule (e.g., two or more different ligands, or a plurality of molecules of one or more ligands) can be conjugated to each nanoparticle. The ratio of ligand molecules to each nanoparticle can be adapted for targeting the nanoparticles to cells expressing the appropriate receptor(s). Non-limiting ratios of ligand to nanoparticle can range from 1:1 to 1,000:1 (e.g., 10:1, 50:1, 100:1, 500:1 or intervening or higher ratios).

The linker may be any linker known in the art, including a protein linker, a peptide linker, a polysaccharide linker, a nucleic acid linker, or a small molecule linker. The linker may be cleavable, e.g., by oxidation, reduction or pH lability.

Other aspects of the disclosure relate to a composition comprising a ligand, such as a ligand comprising a dockerin domain, associated with a therapeutic or diagnostic agent as described herein. In some embodiments, the composition comprises a pharmaceutically acceptable carrier. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), pH adjusting agents (such as inorganic and organic acids and bases), sweetening agents, and flavoring agents. Other non-limiting examples of pharmaceutically acceptable carriers include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. Methods for making such formulations are well known and can be found in, for example, Remington: The Science and Practice of Pharmacy, 22nd edition, Pharmaceutical Press, 2012.

Subjects

The subject may be any mammalian subject, including a human subject. In some embodiments, the subject expresses a heterologous receptor as described herein. In some embodiments, the receptor or a nucleic acid encoding the receptor is delivered to and expressed in a particular tissue or cell, e.g., the heterologous receptor is expressed in the choroid plexus of the subject. In some embodiments, the receptor is expressed in the brain, pancreas, liver, heart, skeletal muscle, lung, prostate, cervix, eye, stomach, intestine, esophagus, gallbladder, colon, hypothalamus, pituitary gland, thyroid, skin, spleen, bladder, bone, or kidney or any other organs, of the subject.

In some embodiments, the subject has a neurodegenerative disease, a lysosomal storage disease, or a brain or central nervous system cancer. Exemplary diseases include Parkinson's disease, Alzheimer's disease, Amyotrophic lateral sclerosis (ALS), Huntington's disease, muscular dystrophies, Pompe's disease, and Bataan's disease. In some embodiments, the subject has a disease described in Table 2. In some embodiments, the subject has a genetic disease that is unique to a particular organ or organ system (e.g., haemophilia for blood, polycystic kidney disease for kidney, Duchenne Muscular Dystrophy for muscle, and Angelman syndrome for brain). Other exemplary diseases that the subject may have include prostate cancer, cervical cancer, and metabolic diseases, e.g., high blood pressure or diabetes.

Nucleic Acid and Recombinant Adeno-Associated Virus (rAAV)

Other aspects of the disclosure relate to a nucleic acid containing a promoter sequence and a sequence that encodes a receptor having a ligand-binding domain (e.g., a cohesin ligand-binding domain) of a non-mammalian protein as described herein (e.g., a bacterial protein) or a ligand-binding domain of a mammalian protein having a ligand that does not bind to an endogenous receptor of a mammal, such as a human. Yet other aspects relate to a recombinant adeno-associated virus (rAAV) particle comprising a nucleic acid containing a promoter sequence and a sequence that encodes a receptor having a ligand-binding domain (e.g., a cohesin ligand-binding domain) of a non-mammalian protein (e.g., a bacterial protein) as described herein or a ligand-binding domain of a mammalian protein having a ligand that does not bind to an endogenous receptor of a mammal, such as a human.

In some embodiments, the receptor further contains an extracellular, transmembrane and/or intracellular domain of a mammalian receptor as described herein (e.g., a transferrin receptor).

In some embodiments, the sequence that encodes a receptor having a ligand-binding domain comprises a nucleotide sequence that encodes the amino acid sequence AVRIKVDTVNAKPGDTVRIPVRFSGIPSK-GIANCDFVYSYDPNVLEIIEIEPGELIVDPN PTKSFD-TAVYPDRKMIVFLFAEDSGTGAYAITEDGVFATI-VAKVKSGAPNGLSVIKFV EVGGFANNDLVEQKTQFFDGGVNVG (SEQ ID NO: 1), or an amino acid sequence that is that is at least 80%, at least 85%, at least 90%, at least 95%, at least 96%, at least 97%, at least 98%, or at least 99% identical to the amino acid sequence of SEQ ID NO:1.

In some embodiments, the sequence that encodes a receptor having a ligand-binding domain comprises a nucleotide sequence that encodes the amino acid sequence MMDQAR-SAFSNLFGGEPLSYTRFSLARQVDGDN-SHVEMKLAVDEEENADNNTKAN VTKPKRCSGSI-CYGTIAVIVFFLIGFMIGYLGYCKGVEPKTECERLA GTESPVREEPGE DFPAARRLYWDDLKRKLSEKLD-STDFTSTIKLLNENSYVPREAGSQKDENLALYVEN QFREFKLSKVWRDQHFVKIQVKDSAQNSVIIVDKN-GRLVYLVENPGGYVAYSKAAT VTGKLVHANFGTKKDFEDLYTPVNGSIVIVRAG-KITFAEKVANAESLNAIGVLIYMD QTKFPIVNAEL-SFFGHAHLGTGDPY-TPGFPSFNHTQFPPSRSSGLPNIPVQTISRAAAEK LFGNMEGDCPSDWKTDSTCRMVTS-ESKNVKLTVSNVLKEIKILNIFGVIKGFVEPDH YVVVGAQRDAWGP-GAAKSGVGTALLLKLAQMFSDMVLKDGFQPSRSII-FASWSAG DFGSVGATEWL-EGYLSSLHLKAFTYINLDKAVLGTSNFKVSASPLLY TLIEKTMQNV KHPVTGQFLYQDSNWASKVEKLTLD-NAAFPFLAYSGIPAVSFCFCEDTDYPYLGTTM DTYKELIERIPELNKVARAAAEVAGQFVIKLTHD-VELNLDYERYNSQLLSFVRDLNQ YRADIKEMGLSLQWLYSARGDFFRATSRLTTDFG-NAEKTDRFVMKKLNDRVMRVE YHFLSPYVSPKESP- FRHVFWGSGSHTLPALLENLKLRKQNNGAFNETL-FRNQLALAT WTIQGAANALSGDVWDIDNEFSEFGSTGSTGST-GADPTRAAVRIKVDTVNAKPGDT VRIPVRFSGIPSK-GIANCDFVYSYDPNVLEIIEIEPGELIVDPNPTKSFD-TAVYPDRKMI VFLFAEDSGTGAYAITEDGVFATIVAKVKSGAPNGLS-VIKFVEVGGFANNDLVEQKT QFFDGGVNVGT (SEQ ID NO: 4), or an amino acid sequence that is that is at least 80%, at least 85%, at least 90%, at least 95%, at least 96%, at least 97%, at least 98%, or at least 99% identical to the amino acid sequence of SEQ ID NO: 4.

In some embodiments, the sequence that encodes a receptor having a ligand-binding domain comprises a nucleotide sequence that encodes the amino acid sequence MGAGAT-GRAMDGPRLLLLLLLGVSLGGA-TRAAVRIKVDTVNAKPGDTVRIPVRFSG IPSK-GIANCDFVYSYDPNVLEIIEIEPGELIVDPNPTKSFDT AVYPDRKMIVFLFAEDSG TGAYAITEDGVFATI-VAKVKSGAPNGLS-VIKFVEVGGFANNDLVEQKTQFFDGGVN VGTRV-GIPKEACPTGLYTHSGECCKACNLGEGVAQPCGAN QTVCEPCLDSVTFSDV VSATEPCKPCTECVGLQSM-SAPCVEADDAVCRCAYGYYQDETT-GRCEACRVCEAGS GLVFSCQDKQNTVCEECPDG-TYSDEANHVDPCLPCTVCEDTERQLRECTRWADAEC EEIPGRWITRSTPPEGSDSTAPSTQEPEAPPEQDLI-ASTVAGVVTTVMGSSQPVVTRGT TDNLIPVYCSI-LAAVVVGLVAYIAFKRWNR-RHKQKIVAPVKQTLNFDLLKLAGDVES NPGPGDTSI (SEQ ID NO: 5), or an amino acid sequence that is that is at least 80%, at least 85%, at least 90%, at least 95%, at least 96%, at least 97%, at least 98%, or at least 99% identical to the amino acid sequence of SEQ ID NO: 5.

The promoter sequence may be any of a number of promoters suitable for use in a selected host cell or tissue. The promoter may be, for example, a constitutive promoter, a tissue-specific promoter, an inducible promoter, or a synthetic promoter. For example, constitutive promoters of different strengths can be used. A nucleic acid described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A and cytomegalovirus (CMV) promoters. Non-limiting examples of constitutive mammalian promoters include various housekeeping gene promoters, as exemplified by the β-actin promoter.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Tissue-specific promoters and/or regulatory elements are also contemplated herein. Non-limiting, exemplary tissue specific promoters include Glial fibrillary acidic protein promoter (GFAP, e.g., for astrocytes of the brain), Mb promoter (e.g., for Muscle), OG-2 promoter (e.g., for bone), SP-B promoter (e.g., for lung), and SYN1 promoter (e.g., for neurons). Other exemplary tissue specific promoters include, but are not limited to, CD14 promoter (e.g., for Monocytic cells), CD43 promoter (e.g., for Leukocytes & platelets), CD45 promoter (e.g., for Haematopoietic cells), CD68 promoter (e.g., for Macrophages), Desmin promoter (e.g., for Muscle), Elastase-1 promoter (e.g., for Pancreatic acinar cells), Endoglin promoter (e.g., for Endothelial cells), Fibronectin promoter (e.g., for Differentiating cells, healing tissues), Flt-1 promoter (e.g., for Endothelial cells), GPIIb promoter (e.g., for Megakaryocytes), ICAM-2 promoter (e.g., for Endothelial cells), Mouse INF-β promoter (e.g., for Hematopoietic cells), NphsI promoter (e.g., for Podocytes), SP-B promoter (e.g., for Lung), WASP promoter (e.g., for Hematopoietic cells), SV40/bAlb promoter (e.g., for Liver), SV40/hAlb promoter (e.g., for Liver), SV40/CD43 promoter (e.g., for Leukocytes & platelets), SV40/CD45 promoter (e.g., for Hematopoietic cells), and NSE/RU5' promoter (e.g., for Mature neurons) (see, e.g., products available from Invivogen).

Synthetic promoters are also contemplated herein. A synthetic promoter may comprise, for example, regions of known promoters, regulatory elements, transcription factor binding sites, enhancer elements, repressor elements, and the like. In some embodiments, the synthetic promoter is a CMV and chicken beta-actin (CBA) hybrid promoter (see exemplary sequence below). Other exemplary synthetic promoters include, but are not limited to, FerL/RU5' promoter, FerH/RU5' promoter, βAct/RU5' promoter, EF1/RU5' promoter, CMV/FerL/chEF1promoter and SV40/hFerH/mEF1 promoter (see, e.g., products available from Invivogen).

Exemplary Sequence of CMV/CBA Promoter:

```
                                              (SEQ ID NO: 10)
CTAGATCTGAATTCGGTACCCTAGTTATTAATAGTAATCAATTACGGGGT

CATTAGTTCATAGCCCATATATGGAGTTCCGCGTTACATAACTTACGGTA

AATGGCCCGCCTGGCTGACCGCCCAACGACCCCCGCCCATTGACGTCAAT

AATGACGTATGTTCCCATAGTAACGCCAATAGGGACTTTCCATTGACGTC

AATGGGTGGACTATTTACGGTAAACTGCCCACTTGGCAGTACATCAAGTG

TATCATATGCCAAGTACGCCCCCTATTGACGTCAATGACGGTAAATGGCC

CGCCTGGCATTATGCCCAGTACATGACCTTATGGGACTTTCCTACTTGGC

AGTACATCTACGTATTAGTCATCGCTATTACCATGGTCGAGGTGAGCCCC

ACGTTCTGCTTCACTCTCCCCATCTCCCCCCCCTCCCCACCCCCAATTTT

GTATTTATTTATTTTTAATTATTTTGTGCAGCGATGGGGGCGGGGGGG

GGGGGGGCGCGCGCCAGGCGGGGCGGGGCGGGGCGAGGGGCGGGGCGGG

GCGAGGCGGAGAGGTGCGGCGGCAGCCAATCAGAGCGGCGCGCTCCGAAA

GTTTCCTTTTATGGCGAGGCGGCGGCGGCGGCGGCCCTATAAAAAGCGAA

GCGCGCGGCGGGCG
```

In some embodiments, the nucleic acid comprises one or more additional regions comprising a sequence that facilitates expression of the receptor, e.g., expression control sequences operatively linked to the receptor sequence. Numerous such sequences are known in the art. Non-limiting examples of expression control sequences include promoters, insulators, silencers, response elements, introns, enhancers, initiation sites, termination signals, and poly(A) tails. Any combination of such control sequences as contemplated herein (e.g., a promoter and an enhancer).

In some embodiments, the nucleic acid contains a construct comprising (a) one or more nucleic acid regions comprising a sequence encoding a receptor as described herein (e.g., comprising a cohesin domain optionally combined with a transferrin or NGFR transmembrane and/or intracellular domain) and (b) one or more (ITR) sequences flanking the one or more heterologous nucleic acid regions. In some embodiments, the ITR sequences are modified or derived from AAV2 ITR sequences. ITR sequences and plasmids containing ITR sequences are known in the art and commercially available (see, e.g., products and services available from Vector Biolabs, Philadelphia, Pa.; Cellbiolabs, San Diego, Calif.; Agilent Technologies, Santa Clara, Ca; and Addgene, Cambridge, Mass.; and Gene delivery to skeletal muscle results in sustained expression and systemic delivery of a therapeutic protein. Kessler P D, Podsakoff G M, Chen X, McQuiston S A, Colosi P C, Matelis L A, Kurtzman G J, Byrne B J. Proc Natl Acad Sci USA. 1996 Nov. 26; 93(24):14082-7; and Curtis A. Machida. Methods in Molecular Medicine™. Viral Vectors for Gene Therapy Methods and Protocols. 10.1385/1-59259-304-6:201 © Humana Press Inc. 2003. Chapter 10. Targeted Integration by Adeno-Associated Virus. Matthew D. Weitzman, Samuel M. Young Jr., Toni Cathomen and Richard Jude Samulski; U.S. Pat. Nos. 5,139,941 and 5,962,313, all of which are incorporated herein by reference).

The rAAV particle may be of any AAV serotype, including any derivative or pseudotype (e.g., 1, 2, 3, 4, 5, 6, 7, 8, 9, 10, 11, 12, or 13, or pseudotypes/derivatives thereof). For example, any ITR sequence derived or modified from an AAV serotype (e.g., 1, 2, 3, 4, 5, 6, 7, 8, 9, 10, 11, 12, or 13) can be used with viral particles comprising capsid proteins of a different serotype (e.g., 1, 2, 3, 4, 5, 6, 7, 8, 9, 10, 11, 12, or 13, or derivatives thereof). Non-limiting examples of derivatives and pseudotypes include rAAV2/1, rAAV2/5, rAAV2/8, rAAV2/9, AAV2-AAV3 hybrid, AAVrh.10, AAVhu.14, AAV3a/3b, AAVrh32.33, AAV-HSC15, AAV-HSC17, AAVhu.37, AAVrh.8, CHt-P6, AAV2.5, AAV6.2, AAV2i8, AAV-HSC15/17, AAVM41, AAV9.45, AAV6 (Y445F/Y731F), AAV2.5T, AAV-HAE1/2, AAV clone 32/83, AAVShH10, AAV2 (Y→F), AAV8 (Y733F), AAV2.15, AAV2.4, AAVM41, and AAVr3.45. Such AAV serotypes and derivatives/pseudotypes, and methods of producing such derivatives/pseudotypes are known in the art (see, e.g., Mol Ther. 2012 April; 20(4):699-708. doi: 10.1038/mt.2011.287. Epub 2012 Jan. 24. The AAV vector toolkit: poised at the clinical crossroads. Asokan A1, Schaffer D V, Samulski R J.). In some embodiments, the rAAV particle is a pseudotyped rAAV particle. In some embodiments, the pseudotyped rAAV particle which comprises (a) a nucleic acid vector comprising AAV2 ITRs and (b) a capsid comprised of capsid proteins derived from AAVx (e.g., AAV1, AAV3, AAV4, AAV5, AAV6, AAV7, AAV8, AAV9, AAV10, AAV11, AAV12, or AAV13). Exemplary rAAV pseudotyped particles include, but are not limited to rAAV2/1, rAAV2/5, rAAV2/8, and rAAV2/9 particles. Methods for producing and using pseudotyped rAAV particles are known in the art (see, e.g., Duan et al., J. Virol., 75:7662-7671, 2001; Halbert et al., J. Virol., 74:1524-1532, 2000; Zolotukhin et al., Methods, 28:158-167, 2002; and Auricchio et al., Hum. Molec. Genet., 10:3075-3081, 2001). In some embodiments, the rAAV is an rAAV2/1 or rAAV2/9 particle.

In some embodiments the rAAV particle comprises an AAV1 or AAV9 serotype capsid and a nucleic acid encoding a receptor comprising a cohesin domain and a NGFR domain. In some embodiments the rAAV particle comprises an AAV1 or AAV9 serotype capsid and a nucleic acid encoding a receptor comprising a cohesin domain and a transferrin receptor domain.

Methods of producing rAAV particles and nucleic acids are also known in the art and commercially available (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, the nucleic acid vector may be combined with one or more helper plasmids, e.g., that contain a rep gene (e.g., encoding Rep78, Rep68, Rep52 and Rep40) and a cap gene (encoding VP1, VP2, and VP3), and transfected into a producer cell line such that the rAAV particle can be packaged and subsequently purified.

In some embodiments, the one or more helper plasmids is a first helper plasmid comprising a rep gene and a cap gene and a second helper plasmid comprising a E1a gene, a E1b gene, a E4 gene, a E2a gene, and a VA gene. In some embodiments, the rep gene is a rep gene derived from AAV2 and the cap gene is derived from AAV9. Helper plasmids, and methods of making such plasmids, are known in the art and commercially available (see, e.g., pDM, pDG, pDP1rs, pDP2rs, pDP3rs, pDP4rs, pDP5rs, pDP6rs, pDG(R484E/R585E), and pDP8.ape plasmids from PlasmidFactory, Bielefeld, Germany; other products and services available from Vector Biolabs, Philadelphia, Pa.; Cellbiolabs, San Diego, Calif.; Agilent Technologies, Santa Clara, Ca; and Addgene, Cambridge, Mass.; pxx6; Grimm et al. (1998), Novel Tools for Production and Purification of Recombinant Adenoassociated Virus Vectors, Human Gene Therapy, Vol. 9, 2745-2760; Kern, A. et al. (2003), Identification of a Heparin-Binding Motif on Adeno-Associated Virus Type 2 Capsids, Journal of Virology, Vol. 77, 11072-11081; Grimm et al. (2003), Helper Virus-Free, Optically Controllable, and Two-Plasmid-Based Production of Adeno-associated Virus Vectors of Serotypes 1 to 6, Molecular Therapy, Vol. 7, 839-850; Kronenberg et al. (2005), A Conformational Change in the Adeno-Associated Virus Type 2 Capsid Leads to the Exposure of Hidden VP1 N Termini, Journal of Virology, Vol. 79, 5296-5303; and Moullier, P. and Snyder, R. O. (2008), International efforts for recombinant adeno-associated viral vector reference standards, Molecular Therapy, Vol. 16, 1185-1188).

An exemplary, non-limiting, transfection method is described next. One or more helper plasmids are produced or obtained, which comprise rep and cap genes for an AAV serotype or pseudotype and the adenoviral VA, E2A (DBP), and E4 genes under the transcriptional control of their native promoters. HEK293 cells (available from ATCC®) are transfected via CaPO$_4$-mediated transfection, lipids or polymeric molecules such as Polyethylenimine (PEI) with the helper plasmid(s) and a nucleic acid vector comprising the receptor construct. The HEK293 cells are then incubated for at least 60 hours to allow for rAAV particle production. The rAAV particles can then be purified from the HEK293 using methods known in the art, e.g., by iodixanol step gradient, CsCl gradient, chromatography, or polyethylene glycol (PEG) precipitation.

In some embodiments, the nucleic acid or the rAAV particle is contained within a composition. In some embodiments, the composition comprises a pharmaceutically-acceptable carrier. In some embodiments, the nucleic acid or the rAAV particle is contained within a kit, which may include instructions for use, such as in a method described herein.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1. Crossing the Blood-Cerebrospinal Fluid Barrier in the Mouse Choroid Plexus with an Engineered Receptor/Ligand System Being one of the most delicate organs of the body, the brain is well protected against potentially toxic substances by the blood-brain barrier (BBB) and the blood-cerebrospinal fluid barrier (BCSFB). As a result the treatment of brain disorders is often limited by the inability of therapeutic drugs to cross either of these barriers from blood to brain. This remains a key obstacle despite decades of research and thus, there is much interest in devising methods to reach the brain more efficiently.

Several strategies have been explored to increase drug delivery into the brain throughout the blood[1]. One of these strategies is based on transiently disrupting the brain barriers. The most widely studied method involves intra-arterial injection of a hyperosmolar molecule such as mannitol or arabinose[2,3]. The osmotic shock causes the shrinkage of cerebrovascular endothelial cells and disruption of the tight junctions, which leads to an increase of permeability of the BBB[4]. This temporal disruption lets drugs and macromolecules diffuse from blood to brain, but the duration of the BBB opening is limited[5,6]. Furthermore, these methods also have the problem of unwanted blood components and other molecules entering the brain, leading to potential neural tissue damage.

Other strategies are based on physiological approaches. Large molecules, like transferrin or insulin, are transported from blood to brain by specific receptors. These receptors are highly expressed on the cells of the BBB and BCSFB, and they transport the ligands by a process called receptor-mediated transcytosis[7]. In this approach, the non-transportable molecule is covalently coupled with the ligand, which then uses the normal receptor-ligand interaction to carry the therapeutic molecule across the brain barriers[8]. However, the widespread expression of these receptors on peripheral organs limits their capability for specific brain delivery. For instance, transferrin receptors have high expression in liver and spleen so targeting this receptor leads to potential delivery not only in the brain, but also to liver and spleen[9-11]. Therefore, specificity in targeting only the brain and specificity in the class of molecules that are delivered are important goals for an ideal brain delivery system.

To address this issue, an engineered-receptor/ligand system was devised to target the brain barriers. The engineered-receptor is expressed in the cells of the brain barriers, providing specificity for brain targeting. The ligand, which recognizes only the engineered receptor, is delivered systemically by intravenous injection. The receptor-ligand combination chosen for this example comes from the anaerobic bacteria *Clostridium thermocellum*, which has a self-assembled multiprotein complex called a cellulosome for degradation of plant cell walls[12]. Cellulosome assembly is mediated by a complementary pair of modules called cohesin and dockerin that provide a specific high affinity interaction. It was hypothesized that by combining the bacterial cohesin-dockerin anchoring system with a mammalian receptor, it would be possible to create an artificial receptor/ligand system that could be used as a high-affinity and potentially specific mammalian delivery system for therapeutic molecules in the brain.

In this study, the binding and transport properties of the cohesin-dockerin system were examined in the mouse brain. The engineered receptor was expressed in cells of the choroid plexus, using a recombinant Adeno-associated virus (rAAV). Subsequently, the ligand was injected systemically and brains were analyzed for receptor/ligand binding. Robust binding of the ligand to the choroid plexus as well as entry of the ligand into ependymocytes and transport to their apical (brain side) membrane was observed.

Results

Ex Vivo Validation of the Receptor/Ligand System.

Cohesin 7 from the CipA scaffoldin gene13 was fused to the C-terminus of the human transferrin receptor (TfR). This construct was then cloned into a recombinant Adeno-associated virus serotype 9 (rAAV9) vector under the control of a hybrid CMV-β actin promoter to generate AAV9-TfR-cohesin (FIG. 1A). It was hypothesized that AAV transduction would allow the TfR-cohesin protein to be expressed in mammalian cells, that the transferrin receptor would localize the TfR-cohesin protein to the cell surface, and that cohesin would then act as the binding domain for dockerin fused to a therapeutic molecule. For purposes of demonstration, the model therapeutic molecule was a fusion protein of GFP and dockerin. To build the GFP-dockerin ligand, the dockerin sequence from the Cel8A cellulose gene14 was fused to the C terminus of the open reading frame of the Green Fluorescence Protein (GFP) (FIG. 1A). The GFP-dockerin protein was then expressed in bacteria and purified as described in the Methods below. GFP was chosen to allow visualization of the location of the GFP-dockerin protein after intravenous injection into animals expressing TfR-cohesin. The molecular weight of the GFP-dockerin molecule was approximately 37 kDa, which was not expected to cross the brain barriers. To test the receptor/ligand system, AAV9-TfR-cohesin was injected into the right ventricle or into the right striatum of mice. The left side in each case (ventricle or striatum) was left uninjected and used as a control.

To locate the expression of TfR-cohesin in the brain, and to determine if cohesin/dockerin binding functioned in brain tissue, brain slices from animals injected with TfR-cohesin were incubated in the presence or absence of GFP-dockerin two weeks post rAAV injection. In animals injected in the right striatum, a high GFP signal was found in the striatum and surrounding brain regions (FIG. 6B) following incubation with GFP-dockerin protein. As expected, slices incubated in the absence of GFP-dockerin showed no GFP signal (FIG. 6A).

In animals injected with AAV9-TfR-cohesin intraventricularly, a high GFP signal was observed in the brain parenchyma surrounding the right lateral ventricle, where the injection of AAV9-TfR-cohesin had occurred (FIG. 1B). GFP signal was detected from the olfactory bulb/anterior olfactory nucleus to the hippocampus (FIG. 7), which reflects the degree to which the rAAV diffused from cerebrospinal fluid (CSF) into the surrounding brain parenchyma. In addition, GFP signal was also found in cells of the choroid plexus of the lateral ventricles, not only on the right side (FIG. 1D) but also on the left side (FIG. 1C). This was presumably due to the fact that choroid plexus cells in both ventricles were accessible to TfR-cohesin virus injected into the right ventricle via CSF.

To rule out the possibility that the AAV9 capsid or some portion of the TfR protein sequence were involved in GFP-dockerin binding, an alternative engineered receptor was made in which the human nerve growth factor receptor (NGFR) amino acid sequence was fused to cohesin and packaged in an AAV1 (rather than AAV9) serotype capsid (AAV1-NGFR-cohesin). When this rAAV virus was injected into the right striatum of the brain a strong GFP signal was found in the right striatum when brain slices were incubated with GFP-dockerin (FIG. 6D), and no signal was found in the absence of the GFP-dockerin ligand (FIG. 6C). This demonstrated that receptor/ligand binding was specific, i.e., due exclusively to the cohesin/dockerin interaction and not to a fortuitous binding of the GFP protein to the transferrin receptor or to components of the AAV capsid protein that might remain two weeks post injection. These results also showed that both TfR-cohesin and NGFR-cohesin could be expressed on the membrane of mammalian cells, and that GFP-dockerin was able to bind TfR-cohesin and NGFR-cohesin in brain tissue, validating that the engineered receptor/ligand system was working correctly.

Ligand Injected Intravenously In Vivo Labels Cells of the Choroid Plexus in the Brain.

The blood-brain barrier and the blood-cerebrospinal fluid barrier present several differences. The BBB is located in the brain parenchyma and it is formed by the endothelial cells of the capillaries in the brain parenchyma. These cells are connected by tight junctions that block the movement of molecules between blood and brain[15]. The endothelial cells are at the same time in contact with blood through their apical membrane and with the brain parenchyma through their basolateral membrane. The BCSFB, however, is located in the choroid plexus organs, which are located in the lateral ventricles as well as the third and fourth ventricles (FIG. 2A). The choroid plexus is basically composed of a dense network of capillaries surrounded by a single layer of epithelial cells called choroidal ependymocytes, and they do not have the same structure as the blood-brain barrier[16]. In the choroid plexus the capillary endothelial cells lack tight junctions and instead the ependymocytes are the cells that are tightly connected, which blocks the movement of molecules from the blood to the brain. Hence, in this barrier the choroid ependymocytes are the cells that are at the same time in contact with blood fluids and brain tissue. These cells however are oriented in the opposite way, with the basolateral membrane facing the blood side and the apical membrane facing the brain side. It was hypothesized that if ependymocytes of the choroid plexus or endothelial cells in the brain parenchyma could be targeted and infected, it would be possible to express the TfR-cohesin receptor on the side in contact with blood, so that GFP-dockerin injected into the blood could potentially reach TfR-cohesin receptors and bind to them in vivo.

To test this hypothesis in the choroid plexus, AAV9-TfR-cohesin virus was injected into the right lateral ventricle of mouse brains. Two weeks later, a single tail vein injection of GFP-dockerin was performed and 8 hours later, brains were fixed and brain slices were analyzed by fluorescence microscopy. GFP signal was found in the choroid plexus of both lateral ventricles (FIGS. 2B and C, arrows) as well as in the choroid plexus of the third (FIG. 2C, arrowhead) and fourth ventricle (FIG. 2D). However, no other GFP signal was found in other regions of the brain. Injection of GFP-dockerin without previous injection of AAV9-TfR-cohesin did not show any GFP signal, ruling out the possibility that GFP-dockerin was able to accumulate in the choroid plexus on its own.

To test the hypothesis on the endothelial cells of the brain parenchyma, which form the BBB, the same experiment was performed but AAV9-TfR-cohesin virus was injected into the striatum. In this approach, the expectation was that rAAV would infect not only neural cells but also the endothelial cells of the capillary network of the brain parenchyma. This in turn would result in expression of TfR-cohesin on the apical (blood) side of brain endothelial cells near the injection site. Two weeks post virus injection, a single tail vein injection of GFP-dockerin was performed and 8 hr later, brains were fixed and brain slices were analyzed by fluorescence microscopy. No GFP signal was found in brain parenchyma suggesting that the endothelial cells of the BBB could not be infected by rAAV9 via the basolateral (brain) side. Alternatively, it is possible that they could not express the TfR-cohesin cassette or the TfR-cohesin protein did not correctly traffic to the apical membrane. To be sure that the TfR-cohesin was actually expressed in the brain parenchyma of these animals, brain slices were incubated with GFP-dockerin. High GFP signal was observed in the striatum and surrounding regions (FIG. 6B).

Together, these results show that when the receptor, TfR-cohesin, was expressed in cells of the choroid plexus organs, GFP-dockerin, injected intravenously, was able to bind and accumulate in those cells, confirming that the engineered receptor/ligand system worked in vivo. The attempt to express the receptor in capillary endothelial cells via brain parenchymal injection was, however, unsuccessful.

Ligand Binds and Enters Choroidal Ependymocytes.

It was next asked as to which cells of the choroid plexus were binding the GFP-dockerin ligand. As mentioned earlier, because the choroid plexus is mainly composed of endothelial cells and choroidal ependymocytes, immunostaining was performed for these two kinds of cells. When slices were immunostained for CD31, a marker of endothelial cells, co-localization of CD31 with GFP was not observed (FIGS. 3A-C). However, when slices were immunostained for two markers of choroidal ependymocytes, α-tubulin and cytokeratin 8/18[17], colocalization with GFP-dockerin was seen for both ependymocyte markers (FIGS. 3D-I, arrows), indicating that the majority of the cells that were binding GFP-dockerin were choroidal ependymocytes. 3D confocal analysis showed that GFP-dockerin was not only on the membranes of choroidal ependymocytes but also throughout the cytosol of the cells, indicating that GFP-dockerin was being internalized into the ependymocytes, presumably via the transferrin receptor. These results demonstrated that systemically administered GFP-dockerin was binding specifically to choroidal ependymocytes and also that it was being internalized into the cytosol of these cells.

Ligand Crosses the Blood-CSF Barrier.

The presence of GFP-dockerin on the basolateral, apical, or both membranes of choroidal ependymocytes was investigated. The apical (or luminal) membrane faces the ventricles of the brain, while the basolateral membrane faces the capillary network, in close contact with blood. Choroidal ependymocytes are highly polarized cells and express different markers on each membrane side[18]. To perform the analysis, an anti-GFP antibody was used, which highlighted the GFP-dockerin located only on the membrane of the cells (FIGS. 4B, F). To identify the apical membrane, two markers were used: phalloidin coupled with a fluorochrome (FIG. 4C) and an antibody against aquaporin 1 (FIG. 4G). Phalloidin binds to F-actin, which is predominantly present in the apical border of ependymocytes[17,19], and aquaporin 1 has also been found predominantly on the apical membrane[20,21].

As shown earlier, the green fluorescence signal of GFP-dockerin was distributed throughout the cytosol of the ependymocytes (FIG. 4A, E). GFP-dockerin labeling of the membrane showed that the ligand was distributed predominantly on one side of the membrane (compare arrowheads in FIGS. 4B and D, and in FIGS. 4F and H), presumably the basolateral membrane, because that part of the membrane showed lower levels of phalloidin (FIGS. 4C-D, arrowheads) or aquaporin 1 signals (FIGS. 4G-H, arrowheads). However, it was also found that some membrane GFP signal co-located with phalloidin (FIGS. 4B-D, arrows) and with Aquaporin 1 (FIGS. 4F-H, arrows), showing that some GFP-dockerin was located on the apical membrane of the ependymocytes, which is the brain side of the blood-cerebrospinal fluid barrier. Since GFP-dockerin could only have entered from the basolateral side, these observations suggested that GFP-dockerin could enter from the basolateral side and be transcytosed to the apical membrane of choroidal ependymocytes.

To confirm the results found by confocal microscopy, the same samples were examined by electron microscopy. GFP-dockerin was labeled by peroxidase/DAB immunohistochemistry using an anti-GFP monoclonal antibody (FIG. 5A). In the electron micrographs of the choroid plexus tissue, peroxidase activity was revealed by an electron-dense reaction product (FIG. 5B, arrowheads). The brain and blood sides of choroid ependymocytes have different morphology: the apical (ap) (or luminal) membranes display cilia and dense microvilli (FIGS. 5B-C, ap), while the basal and lateral surfaces (bl) are flat with strongly folded labyrinths with the neighboring cells at the transition from lateral to basal surfaces (FIGS. 5B-C, bl). As expected, electron-dense particles corresponding to GFP-dockerin were detected in high number on the basolateral surfaces of ependymocytes (FIGS. 5B-C, arrowheads). However, some cells with electron-dense particles were also observed on the apical membrane, between the microvilli (FIG. 5C, arrow). This result confirmed the findings from the confocal microscopy experiments that some GFP-dockerin was located on the apical membrane of ependymocytes, suggesting that transcytosis of GFP-dockerin from the basolateral to the apical surface had occurred.

Taken together, these results demonstrate that GFP-dockerin injected into blood was able to bind to the TfR-cohesin expressed on the basolateral membrane of choroidal ependymocytes. Furthermore, the bound GFP-dockerin was internalized in the majority of the ependymocytes, and in some cells GFP-dockerin was transported from the basolateral membrane (blood side) to the apical membrane (brain side), hence crossing the blood-cerebrospinal fluid barrier.

One of the most promising methods for brain delivery is the "trojan-horse" strategy[7,8] in which receptors of the blood brain barrier are targeted to transport a therapeutic molecule into the brain by receptor-mediated transcytosis. Previous studies have targeted receptors for insulin, transferrin, insulin-like growth factor, leptin, and lipoprotein[1,22]. However, because these receptors are expressed not only in the brain vasculature, but also in other organs of the body, there is a potential for off-target effects that can cause undesirable toxicity. A well-documented case is transferrin receptor. This receptor is highly expressed in the brain barriers[23,24], but also in other organs[25,26], so when transferrin receptor is targeted with an antibody, the concentration of the antibody increased in the brain but also in TfR-rich organs, like spleen and liver[11,27,28].

In an attempt to target only the brain, the present study aimed to build a simple and very specific receptor-ligand system using the cohesin-dockerin domains from the bacterium C. thermocellum. The cohesin and dockerin binding domains are small (cohesin=143 aa, ~17 kDa; dockerin=62 aa, ~7 kDa) and simple, requiring no post-translational processing or lipid attachment. They also have a dissociation constant that is comparable to high affinity antibodies ($K_d$ between $10^{-8}$-$10^{-11}$M)[29]. The use of GFP in the ligand fusion protein with dockerin allowed the protein to be easily tracked during protein production as well as experimental analysis. In principle, however, any therapeutic protein, peptide or small molecule could be fused to the dockerin peptide for delivery to the brain. Moreover, the dockerin ligand can be produced in large scale bacterial culture, either for complexing with a therapeutic small molecule or as a fusion protein with a therapeutic protein or peptide. The GFP-dockerin ligand tested here contained 328 residues for a combined MW of 37 kDa, but it is possible that larger ligands may work as well. In addition, dockerin can be complexed with artificial nanoparticles or with small viruses such as rAAV that carry gene cassettes expressing cellular genes, shRNAs, or other DNA or gene expression modifying proteins. For example, it has been previously shown that the GFP protein can be fused to the N terminus of the minor AAV capsid protein VP2 and thus, decorate the outside of the rAAV capsid with approximately 6 copies of the 27 kDa GFP protein[30]. A similar approach could be used with the 7 kDa dockerin protein, thus providing specific binding and entry of rAAV vectors into brain ventricles for distribution to brain parenchyma.

The mammalian receptor chosen for modification by fusion with the cohesin domain was the transferrin receptor. It was chosen because it had been previously shown to mediate receptor-mediated transcytosis in the brain barriers[10,31]. However, in principle, any one of the endogenous receptors that have previously been shown to transport molecules across either the BBB or the BCSFB could also be fused to cohesin. Surprisingly, the results herein show that the TfR-cohesin/GFP-dockerin complex is readily internalized in choroid ependymocytes. It is unlikely that binding of cohesin and dockerin triggers the internalization of the TfR-cohesin. Rather, it is possible that the cohesin/GFP-dockerin binding does not prevent the interaction of circulating endogenous transferrin with the TfR docking site of TfR-cohesin, and that when that happens, the entire complex including transferrin and GFP-dockerin is internalized. This phenomena has been seen before when the transferrin receptor was targeted with antibodies that do not target the binding site for transferrin[10,32].

In this study rAAV1 and rAAV9 were used to transduce the choroid plexus. It is noted, however, that rAAV4[33,34] has been shown to be the best serotype for transducing choroid plexus, and the use of rAAV4 to deliver the cohesin-transferrin receptor could potentially improve the efficiency of the trans-BCSFB delivery system. In addition, although AAV was used to transduce choroid plexus cells, other delivery vehicles that express the cohesin-transferrin receptor either transiently (DNA nanoparticles) or permanently (retrovirus vectors) could also potentially be used.

Although the dockerin-cohesin-transferrin system seemed to work in the choroid plexus, no evidence was found of GFP-dockerin binding in endothelial cells of the BBB, which also express transferrin on their surface. It has been shown that the AAV1 and AAV9 serotypes are able to infect endothelial cells when injected intravenously[35,36]. However, in the experiments herein these AAV serotypes were not able to infect endothelial cells when AAV was injected into brain parenchyma. Brain endothelial cells are functionally polarized with distinct apical and basolateral membrane domains[37,38]. Therefore, a possible explanation for the absence of TfR-cohesin expression is that the receptor required for AAV entry in brain endothelial cells is not present on the basolateral membrane (brain side). An alternative explanation is that endothelial cells are surrounded by astrocytic foot processes and pericytes, thereby physically blocking AAV access to endothelial membranes[15].

The experimental findings herein are the first to demonstrate that the bacterial cohesin-dockerin anchoring domains are functional in vivo in a mammalian animal model. They also demonstrate that the engineered receptor/ligand system could potentially be an effective tool for drug delivery in the brain. Unlike other methods that rely on endogenous receptors, an artificial receptor was engineered that was expressed uniquely in the choroid plexus of the brain via AAV gene delivery and, in addition, coded for a ligand binding domain that is foreign to mammals. In principle this allows for maximum specificity for the brain and should reduce off target effects during drug delivery. Furthermore, the high specificity of different cohesin-dockerin pairs would allow for the controlled delivery of two or more drugs simultaneously. In addition, although the system contains bacterial protein domains foreign to mammalian animal models, no evidence of acute toxicity was observed during the experiments. However, several important questions still remain. Among them, it is not yet known if the dockerin binding domain can fortuitously bind to receptors in other organs and it has not yet been determined if the primate immune system will preclude repeated intravenous injections of the dockerin peptide, which is desirable in a drug delivery system.

In conclusion, the study herein shows that the engineered receptor/ligand system has promising features as a potential brain delivery system and as a tool to study receptor-mediated transcytosis. More generally, this system could be used to target other organs in a similar fashion.

Material and Methods

Recombinant Plasmids.

pTR-TfR-cohesin. The cohesin open reading frame (143 amino acids (aa)) from pRSET-A_(I27)3-c7A-(I27)239 was amplified using polymerase chain reaction (PCR) as a BamHI fragment (see Table 1 for primer sequences) and inserted into pTfR-PAmCherry140 (Addgene plasmid 31948, Cambridge, Mass., USA), to produce the pTfR-cohesin-PAmCherry1 plasmid. To construct the pTR-TfR-cohesin plasmid, the TfR-cohesin open reading frame from pTfR-cohesin-PAmcherry1 was PCR amplified as a NotI-SalI fragment and cloned into pTR-UF1141, swapping it with the sequence containing the hGFP and neomycin-resistance genes. The final construct pTR-TfR-cohesin contained the coding sequences for human transferrin receptor fused in frame with the cohesin sequence at the C terminal end of TfR under the control of the synthetic CBA promoter[42] and the human bovine growth hormone poly(A) site, all of it flanked by the AAV2 terminal repeats (FIG. 1A).

TABLE 1

| PCR primers used for clone construction | | |
|---|---|---|
| pTR---TfR---cohesin | | |
| cohesin---Fv---BamHI | ATGGATCCCACTCGAGCCGCAGTAAGGATTAAGG | (SEQ ID NO: 11) |
| cohesin---Rv---BamHI | ATGGATCCTTGGGAATTCCTACTCGAGTTCC | (SEQ ID NO: 12) |
| TfR---cohesin---Fw---NotI | TAGCGGCCGCCACCATGATGGATCAAGCTAGAT | (SEQ ID NO: 13) |
| TfR---cohesin---Rv---Stop---SalI | TAGTCGACTCAAGTTCCAACATTTACTCCACCGT | (SEQ ID NO: 14) |
| pTR---NGFR---cohesin | | |
| RSP---Fw---BamHI | GATCCTCCATGGGGGCAGGTGCCACCGGCCGCGCCA TGGACGGGCCGCGCCTGCTGCTGTTGCTGCTTCTGG GGGTGTCCCTTGGAGGTGCCAC | (SEQ ID NO: 15) |
| RSP---Rv---XhoI | TCGAGTGGCACCTCCAAGGGACACCCCCAGAAGCAG CAACAGCAGCAGGCGCGGCCCGTCCATGGCGCGGC CGGTGGCACCTGCCCCCATGGAG | (SEQ ID NO: 16) |
| NoRSP---ΔNGFR---Fw---EcoRI | CCTTGGAATTCCCAAGGAGGCATGCCCCACAGGC | (SEQ ID NO: 17) |
| NoRSP---ΔNGFR---Rv---NotI | GCAGGGGCGGCCGCTAGATCGATGTGTCGCCGGGCCC | (SEQ ID NO: 18) |
| cohesin---Fw---XhoI | GAAAGAATTGAGATCTCGAGCCGCAGTAAGG | (SEQ ID NO: 19) |
| cohesin---Rv---XhoI | CCACTTCTATTACTCGAGTTCCAACATTTACTCC | (SEQ ID NO: 20) |
| pET28A---GFP---dockerin | | |
| dockerinEcoRI---Fw | GCAGTGAATTCCCGAATCCTTTGAGTGACCTTTCC | (SEQ ID NO: 21) |
| dockerin---XhoI---Rv | GGTGCTCGAGTCAATAAGGTAGG | (SEQ ID NO: 22) |
| GFP---Nde---Fw | GACCATATGAAGGGCGAGGAGCTGTTCACC | (SEQ ID NO: 23) |
| GFP---EcoRI---Rv | ACTGCGAATTCCTTATACAGCTCGTCCATGCCGAG | (SEQ ID NO: 24) | pTR-NGFR-Cohesin.

The cohesin coding sequence was inserted in frame into the nerve growth factor receptor (NGFR) coding sequence between the reticulum signal peptide of NGFR and receptor domain. The reticulum signal peptide (RSP) sequences of NGFR were purchased and the BamHI-XhoI fragment was inserted into a plasmid containing a multicloning site (MCS-plasmid). The NGFR open reading frame without the RSP (NoRSP-ΔNGFR) was PCR amplified from the plasmid ΔNGFR-2A-p4743, as a EcoRI-NotI fragment and inserted in the RSP-MCS-plasmid, in the same open reading frame as the RSP. The cohesin open reading frame was amplified as a XhoI-XhoI fragment and inserted into the RSP-ΔNGFR-MCS-plasmid, between RSP and ΔNGFR in the same open reading frame, producing the RSP-cohesin-NGFR-MCS-plasmid. The fragment RSP-cohesin-NGFR was cut with NotI and SalI and inserted into the pRT-UF11 digested with NotI and SalI, swapping it with the sequence containing the hGFP and neomycin-resistance genes to make pTR-NGFR-cohesin. The final pTR-NGFR-cohesin construct contained the coding sequences of human NGFR fused with cohesin under the control of the synthetic CBA promoter and the human bovine growth hormone poly(A) site, all of it flanked by the AAV2 terminal repeats.

pET28A-GFP-Dockerin.

The *C. thermocellum* dockerin sequence (containing also the linker separating the catalytic unit from the dockerin, at the 5' end) was PCR amplified from pET28-Cel8A44. The EcoRI/XhoI fragment containing a the linker separating the catalytic unit from the dockerin (at the 5') and stop codon insertion before the XhoI site was cloned into a pET28a vector (Novagen). The coding sequence for GFP was PCR amplified from (Hys)6-GFP-ssrA45, as an NdeI/EcoRI fragment and cloned into pET28-dockerin. The resulting construct coded for a protein containing a his tag, GFP, the linker and dockerin, all in the same reading frame.

GFP-Dockerin Protein Production.

*E. Coli* enhanced BL21 strain (T7 express lysY, New England Biolabs, Ipswich, Mass., USA) containing pET28A-GFP-dockerin was grown in 500 mL LB with 50 µg/mL kanamycin and grown for 4 hours at 30° C. Subsequently IPTG (isopropyl-β-D-thiogalactopyranose) was added at a final concentration of 0.5 mM and culture growth was continued for 20 hours at 16° C. to induce protein expression. Cells were harvested by centrifugation (6000 g for 15 min at 4° C.) and resuspended in 20 mL of His buffer (50 mM Tris pH 7.65, 25 mM NaCl, 2 mM $CaCl_2$) supplemented with protease inhibitors (PMSF 0.5 mM, pepstatin A 5 µg/mL, chymostatin 1 µg/mL, leupeptin 1 µg/mL, aprotinin 2 µg/µL) and lysed with a French Press at 1200 psi of pressure. The lysate was centrifuged (20000 g for 30 min at 4° C.), and the supernatant was loaded onto a 5 mL HisTrap HP column (GE Healthcare Life Sciences, Pittsburgh, Pa., USA), pre-equilibrated with His buffer. Proteins were eluted in His buffer using a 30 mL linear gradient of 0-200 mM imidazole. Fractions were collected, analyzed (see below) and loaded onto a 5 mL Hitrap Q HP column (GE Healthcare Life Sciences, Pittsburgh, Pa., USA), pre-equilibrated with Q buffer (25 mM Tris-HCl pH 8.5, 1 mM DTT, 1 mM $CaCl_2$) with protease inhibitor cocktail. GFP-dockerin was eluted in Q buffer using a linear gradient of 0-500 mM NaCl. Analysis of the fractions were performed using a fluorometer to measure GFP signal (excitation filter: 485±20 nm, emission filter: 528±20 nm) and by SDS/PAGE with Comassie staining. The fractions containing relatively pure protein were pooled and dialyzed against PBS pH 8.0 and concentrated in an Apollo 20 kDa concentrator (Orbital biosciences, MA, USA) in 0.1 M PBS pH 8.0. The GFP-dockerin was aliquoted and stored at −20° C.

Production of rAAV.

rAAV was isolated essentially as described[46], with minor modifications. For the production of AAV9-TfR-cohesin, the plasmid pIM45-9 that expresses AAV2 rep and the AAV9 cap, was co-transfected using PEI[47,48] into HEK-293 cells with pTR-TfR-cohesin and pXX649, which contains the adenovirus E4, VA, and E2a helper regions, to produce the AAV9-TfR-cohesin virus. The recombinant virus was purified by iodixanol step gradient, followed by vector concentration and buffer exchange with lactated Ringer's in an Apollo 150 kDa concentrator (Orbital biosciences, MA, USA). The virus was stored at −80° C. AAV1-NGFR-cohesin, was produced by the same method, but using the plasmids pXYZ146 and pTR-NGFR-cohesin during the transfection. Virus titers (vector genomes per mL) were determined by dot blot: AAV1-NGFR-cohesin=$2.47 \times 10^{12}$ vg/mL. AAV9-TfR-cohesin=$5.58 \times 10^{12}$ vg/mL.

Animals.

Balb/cj strain mice 4-5 weeks of age were used for the experiments.

Intracerebral Injection of AAVs.

All surgical procedures were performed using aseptic techniques and isoflurane gas anesthesia. After mice were anesthetized, they were placed in the stereotactic frame (Kopf Instruments, Tujunga, Calif., USA), and rAAV vectors were injected into either the right Striatum (Str) (anterior-posterior (AP) −0.3 mm, lateral (lat) −2.0 mm, dorsoventral (DV) −3.0 mm) or the right Lateral ventricle (LV) (AP −0.3, Lat −1.0, DV −2.0), through a glass micropipette with an inner diameter ~30-40 µm at a rate of 0.5 µL/min. Animals were injected with a total of 2 µL of virus in the Str or 10 µL in the LV. The needle was left in place for 5 min prior to withdrawal from the brain.

Systemic Injection of GFP-Dockerin.

After the animals were anesthetized with isoflurane, a single dose of 100 µL of GFP-dockerin (3 µg/µL) was administrated via the tail vein, using an insulin syringe (30G×½") (Easy touch, TX, USA) over a period of 30 seconds. Animals were perfused 8 hours later.

Brain Tissue Preparation.

Animals were deeply anesthetized with pentobarbital (Beuthanasia-D, Merck Animal Health, Summit, N.J., USA) and perfused through the ascending aorta. Brains were perfused with 10 mL of saline solution, followed by 10 mL of ice-cold 4% paraformaldehyde (PFA) in 0.1 M phosphate buffer (PB), pH 7.4. Brains were removed and postfixed overnight at 4° C. in paraformaldehyde (PFA) solution.

Forty-micrometer-thick brain coronal sections (40 µm) were cut on a vibratome (Leica Microsystems) and mounted for fluorescent microscopy analysis or processed for GFP-dockerin incubation or immunohistochemistry.

GFP-Dockerin Incubation.

Brain sections were incubated overnight at 4° C. with 0.02 mg/mL of dockerin-GFP, 0.1% Triton-X100 (T9284, Sigma-Aldrich, St. Louis, Mo., USA) and 3% goat serum (01-6201, Life Technologies, Grand Island, N.Y., USA). Brain sections were mounted on slides with Mowiol 4-88 (81381, Sigma-Aldrich). Samples were examined with a fluorescent stereo-microscope or a Fluorescence Microscope (Leica Microsystems, Buffalo Grove, Ill., USA) and images were processed with Pixelmator software (UAB Pixelmator Team).

Immunohistochemistry for Confocal Microscopy.

Immunostaining were carried out on free-floating sections as follows: Incubation with 0.1% Triton-X100 (T9284, Sigma-Aldrich), 3% goat serum (01-6201, Life Technologies) or donkey serum (D9663, Sigma-Aldrich) in PBS for 1 hour at room temperature (RT); incubation with Phalloidin-Atto 565 (94072, Sigma-Aldrich) or one of the primary antibodies 4° C. overnight: rabbit anti-α Tubulin (ab18251, Abcam, Cambridge, Mass., USA) diluted 1:500, guinea pig anti-cytokeratin 8/18 (GP11, Progen Biotechnik, Heidelberg, Germany) diluted 1:100, rabbit anti-CD31 (ab28364, Abcam) diluted 1:100 or rabbit anti-Aquaporin 1 (ab15080, Abcam) diluted 1:125; 3 washes with PBS for 10 minutes each wash; incubation with one of the secondary antibodies for 2 hours at RT: Alexa Fluor555 donkey anti-Rabbit (A-31572, Life Technologies) diluted 1:500 or Alexa Fluor555 goat anti-Guinea Pig (A-21435, Life Technologies) diluted 1:500. Sections were then incubated with 4',6-diamidino-2-phenylindole (DAPI) at 1 µg/mL for 10 min, washed with PBS 3 times for 10 minutes each wash, mounted on slides with Mowiol 4-88 (81381, Sigma-Aldrich) and examined with a confocal microscope Leica TCS SP5 (Leica Microsystems).

To label GFP that was present only on the surface of the membranes, sections were stained without Triton-X100, as follows: Incubation with 3% goat serum (01-6201, Life Technologies) in PBS for 1 hour at RT; incubation with the primary rat anti-GFP (04404-84, Nacalai USA, San diego, CA, USA) diluted 1:1000 at 4° C. overnight; 3 washes with PBS for 10 minutes each wash; incubation with the secondary Alexa Fluor647 goat anti-Rat (A-21247, Life Technologies) for 2 hours at RT; 3 washes with PBS for 10 minutes each wash; incubation of the slices with 4% PFA; 3 washes with PBS for 10 minutes each wash. Once the GFP membrane staining was complete, the sections were stained for the other marker using Triton X-100, following the procedure described above, for Aquaporin 1 or Phalloidin.

To label GFP on the surface of membranes for electron microscopy, sections were processed as follows: incubation with 0.5% $H_2O_2$, 10% Methanol in PBS for 15 min; 3 washes of 10 min. each with PBS; incubation with 1% goat serum in PBS for 1 hour at RT; incubation with primary rat anti-GFP antibody (04404-84, Nacalai USA) diluted 1:500 at 4° C. overnight; 3 washes with PBS for 10 minutes each wash; incubation with the secondary biotinylated goat anti-rat antibody (BA-9401, Vector Laboratories, Burlingame, Calif., USA) diluted 1:500 for 2 hours at RT; 3 washes of 10 min. each with PBS; incubation with VECTASTAIN Elite ABC Kit (PK-6100, Vector Laboratories) for 1 hour at RT; 3 washes with PBS for 10 minutes each wash. The sections were then stained using the NovaRED Peroxidase (HRP) Substrate Kit (SK-4800, Vector Laboratories) for 10 min, washed and processed for electron microscopy as described below.

Electron Microscopy.

Transmission electron microscopy was carried out as described previously[50]. After immunohistochemistry, sections were post-fixed with 1% osmium tetroxide, dehydrated and embedded in EMbed812/Araldite epoxy resin. Ultrathin sections (100 nm) were then cut from the block surface, collected on 100 mesh carbon coated Formvar copper grids and examined in an FEI Spirit LaB6 120 kV transmission electron microscope equipped with a Gatan Ultrascan 1000XP, 2kX2k CCD digital camera.

REFERENCES

1. Gabathuler, R. Approaches to transport therapeutic drugs across the blood-brain barrier to treat brain diseases. Neurobiol Dis 37, 48-57 (2010).doi:10.1016/j.nbd.2009.07.028
2. Neuwelt, E. A. Reversible osmotic blood-brain barrier disruption in humans: implications for the chemotherapy of malignant brain tumors. Neurosurgery 7, 204 (1980).
3. Siegal, T., Rubinstein, R., Bokstein, F., Schwartz, A., Lossos, A., Shalom, E., Chisin, R. and Gomori, J. M. In vivo assessment of the window of barrier opening after osmotic blood-brain barrier disruption in humans. J Neurosurg 92, 599-605 (2000).doi:10.3171/jns.2000.92.4.0599
4. Rapoport, S. I. Osmotic opening of the blood-brain barrier: principles, mechanism, and therapeutic applications. Cell Mol Neurobiol 20, 217-30 (2000).
5. Rapoport, S. I. Advances in osmotic opening of the blood-brain barrier to enhance CNS chemotherapy. Expert Opin Investig Drugs 10, 1809-18 (2001).doi:10.1517/13543784.10.10.1809
6. Ikeda, M., Bhattacharjee, A. K., Kondoh, T., Nagashima, T. and Tamaki, N. Synergistic effect of cold mannitol and Na(+)/Ca(2+) exchange blocker on blood-brain barrier opening. Biochem Biophys Res Commun 291, 669-74 (2002).doi:10.1006/bbrc.2002.6495
7. Xiao, G. and Gan, L. S. Receptor-mediated endocytosis and brain delivery of therapeutic biologics. Int J Cell Biol 2013, 703545 (2013).doi:10.1155/2013/703545
8. Pardridge, W. M. Drug and gene targeting to the brain with molecular Trojan horses. Nat Rev Drug Discov 1, 131-9 (2002).doi:10.1038/nrd725
9. Jefferies, W. A., Brandon, M. R., Hunt, S. V., Williams, A. F., Gatter, K. C. and Mason, D. Y. Transferrin receptor on endothelium of brain capillaries. Nature 312, 162-3 (1984).
10. Pardridge, W. M., Buciak, J. L. and Friden, P. M. Selective transport of an anti-transferrin receptor antibody through the blood-brain barrier in vivo. J Pharmacol Exp Ther 259, 66-70 (1991).
11. Moos, T. and Morgan, E. H. Restricted transport of anti-transferrin receptor antibody (OX26) through the blood-brain barrier in the rat. J Neurochem 79, 119-29 (2001).
12. Bayer, E. A., Belaich, J. P., Shoham, Y. and Lamed, R. The cellulosomes: multienzyme machines for degradation of plant cell wall polysaccharides. Annu Rev Microbiol 58, 521-54 (2004).doi:10.1146/annurev.micro.57.030502.091022
13. Gerngross, U. T., Romaniec, M. P., Kobayashi, T., Huskisson, N. S. and Demain, A. L. Sequencing of a *Clostridium thermocellum* gene (cipA) encoding the cellulosomal SL-protein reveals an unusual degree of internal homology. Mol Microbiol 8, 325-34 (1993).
14. Anbar, M., Gul, O., Lamed, R., Sezerman, U. O. and Bayer, E. A. Improved thermostability of *Clostridium thermocellum* endoglucanase Cel8A by using consensus-guided mutagenesis. Appl Environ Microbiol 78, 3458-64 (2012).doi:10.1128/AEM.07985-11
15. Abbott, N. J., Rönnbäck, L. and Hansson, E. Astrocyte-endothelial interactions at the blood-brain barrier. Nat Rev Neurosci 7, 41-53 (2006).doi:10.1038/nrn1824
16. Damkier, H. H., Brown, P. D. and Praetorius, J. Cerebrospinal fluid secretion by the choroid plexus. Physiol Rev 93, 1847-92 (2013).doi:10.1152/physrev.00004.2013
17. Li, Y. C., Bai, W. Z., Sakai, K. and Hashikawa, T. Fluorescence and electron microscopic localization of F-actin in the ependymocytes. J Histochem Cytochem 57, 741-51 (2009).doi:10.1369/jhc.2009.953646
18. Christensen, I. B., Gyldenholm, T., Damkier, H. H. and Praetorius, J. Polarization of membrane associated proteins in the choroid plexus epithelium from normal and slc4a10 knockout mice. Front Physiol 4, 344 (2013).doi:10.3389/fphys.2013.00344
19. Li, Y. C., Bai, W. Z. and Hashikawa, T. Regionally varying F-actin network in the apical cytoplasm of ependymocytes. Neurosci Res 57, 522-30 (2007).doi:10.1016/j.neures.2006.12.009
20. Speake, T., Freeman, L. J. and Brown, P. D. Expression of aquaporin 1 and aquaporin 4 water channels in rat choroid plexus. Biochim Biophys Acta 1609, 80-6 (2003).
21. Longatti, P. L., Basaldella, L., Orvieto, E., Fiorindi, A. and Carteri, A. Choroid plexus and aquaporin-1: a novel explanation of cerebrospinal fluid production. Pediatr Neurosurg 40, 277-83 (2004).doi:10.1159/000083740
22. Larsen, J. M., Martin, D. R. and Byrne, M. E. Recent advances in delivery through the blood-brain barrier. Curr Top Med Chem 14, 1148-60 (2014).
23. Moos, T. and Morgan, E. H. Transferrin and transferrin receptor function in brain barrier systems. Cell Mol Neurobiol 20, 77-95 (2000).

24. Roberts, R. L., Fine, R. E. and Sandra, A. Receptor-mediated endocytosis of transferrin at the blood-brain barrier. J Cell Sci 104 (Pt 2), 521-32 (1993).
25. Lu, J. P., Hayashi, K. and Awai, M. Transferrin receptor expression in normal, iron-deficient and iron-overloaded rats. Acta Pathol Jpn 39, 759-64 (1989).
26. Newman, R., Schneider, C., Sutherland, R., Vodinelich, L. and Greaves, M. The transferrin receptor. Trends in Biochemical Sciences 7, 397-400 (1982).doi:/10.1016/0968-0004(82)90184-0at <http://www.sciencedirect.com/science/article/pii/0968000482901840>
27. Ko, Y. T., Bhattacharya, R. and Bickel, U. Liposome encapsulated polyethylenimine/ODN polyplexes for brain targeting. J Control Release 133, 230-7 (2009).doi:10.1016/j.jconrel.2008.10.013
28. Shi, N., Boado, R. J. and Pardridge, W. M. Receptor-mediated gene targeting to tissues in vivo following intravenous administration of pegylated immunoliposomes. Pharm Res 18, 1091-5 (2001).
29. Slutzki, M., Barak, Y., Reshef, D., Schueler-Furman, O., Lamed, R. and Bayer, E. A. Indirect ELISA-based approach for comparative measurement of high-affinity cohesin-dockerin interactions. J Mol Recognit 25, 616-22 (2012).doi:10.1002/jmr.2178
30. Warrington, K. H., Gorbatyuk, O. S., Harrison, J. K., Opie, S. R., Zolotukhin, S. and Muzyczka, N. Adeno-associated virus type 2 VP2 capsid protein is nonessential and can tolerate large peptide insertions at its N terminus. J Virol 78, 6595-609 (2004).doi:10.1128/JVI.78.12.6595-6609.2004
31. Friden, P. M., Walus, L. R., Musso, G. F., Taylor, M. A., Malfroy, B. and Starzyk, R. M. Anti-transferrin receptor antibody and antibody-drug conjugates cross the blood-brain barrier. Proc Natl Acad Sci USA 88, 4771-5 (1991).
32. Jefferies, W. A., Brandon, M. R., Williams, A. F. and Hunt, S. V. Analysis of lymphopoietic stem cells with a monoclonal antibody to the rat transferrin receptor. Immunology 54, 333-41 (1985).
33. Liu, G., Martins, I., Wemmie, J. A., Chiorini, J. A. and Davidson, B. L. Functional correction of CNS phenotypes in a lysosomal storage disease model using adeno-associated virus type 4 vectors. J Neurosci 25, 9321-7 (2005).doi:10.1523/JNEUROSCI.2936-05.2005
34. Dodge, J. C., Treleaven, C. M., Fidler, J. A., Hester, M., Haidet, A., Handy, C., Rao, M., Eagle, A., Matthews, J. C., Taksir, T. V., Cheng, S. H., Shihabuddin, L. S. and Kaspar, B. K. AAV4-mediated expression of IGF-1 and VEGF within cellular components of the ventricular system improves survival outcome in familial ALS mice. Mol Ther 18, 2075-84 (2010).doi:10.1038/mt.2010.206
35. Chen, S., Kapturczak, M., Loiler, S. A., Zolotukhin, S., Glushakova, O. Y., Madsen, K. M., Samulski, R. J., Hauswirth, W. W., Campbell-Thompson, M., Berns, K. I., Flotte, T. R., Atkinson, M. A., Tisher, C. C. and Agarwal, A. Efficient transduction of vascular endothelial cells with recombinant adeno-associated virus serotype 1 and 5 vectors. Hum Gene Ther 16, 235-47 (2005).doi:10.1089/hum.2005.16.235
36. Varadi, K., Michelfelder, S., Korff, T., Hecker, M., Trepel, M., Katus, H. A., Kleinschmidt, J. A. and Müller, O. J. Novel random peptide libraries displayed on AAV serotype 9 for selection of endothelial cell-directed gene transfer vectors. Gene Ther 19, 800-9 (2012).doi:10.1038/gt.2011.143
37. Betz, A. L., Firth, J. A. and Goldstein, G. W. Polarity of the blood-brain barrier: distribution of enzymes between the luminal and antiluminal membranes of brain capillary endothelial cells. Brain Res 192, 17-28 (1980).
38. Hudson, N., Powner, M. B., Sarker, M. H., Burgoyne, T., Campbell, M., Ockrim, Z. K., Martinelli, R., Futter, C. E., Grant, M. B., Fraser, P. A., Shima, D. T., Greenwood, J. and Turowski, P. Differential apicobasal VEGF signaling at vascular blood-neural barriers. Dev Cell 30, 541-52 (2014).doi:10.1016/j.devcel.2014.06.027
39. Valbuena, A., Oroz, J., Hervás, R., Vera, A. M., Rodríguez, D., Menéndez, M., Sulkowska, J. I., Cieplak, M. and Carrión-Vázquez, M. On the remarkable mechanostability of scaffoldins and the mechanical clamp motif. Proc Natl Acad Sci USA 106, 13791-6 (2009).doi:10.1073/pnas.0813093106
40. Subach, F. V., Patterson, G. H., Manley, S., Gillette, J. M., Lippincott-Schwartz, J. and Verkhusha, V. V. Photoactivatable mCherry for high-resolution two-color fluorescence microscopy. Nat Methods 6, 153-9 (2009).doi:10.1038/nmeth.1298
41. Zolotukhin, S., Potter, M., Hauswirth, W. W., Guy, J. and Muzyczka, N. A "humanized" green fluorescent protein cDNA adapted for high-level expression in mammalian cells. J Virol 70, 4646-54 (1996).
42. Xu, L., Daly, T., Gao, C., Flotte, T. R., Song, S., Byrne, B. J., Sands, M. S. and Parker Ponder, K. CMV-beta-actin promoter directs higher expression from an adeno-associated viral vector in the liver than the cytomegalovirus or elongation factor 1 alpha promoter and results in therapeutic levels of human factor X in mice. Hum Gene Ther 12, 563-73 (2001).doi:10.1089/104303401300042500
43. Wohlgensinger, V., Seger, R., Ryan, M. D., Reichenbach, J. and Siler, U. Signed outside: a surface marker system for transgenic cytoplasmic proteins. Gene Ther 17, 1193-9 (2010).doi:10.1038/gt.2010.73
44. Anbar, M., Lamed, R. and Bayer, E. Thermostability Enhancement of Clostridium thermocellum Cellulosomal Endoglucanase Cel8A by a Single Glycine Substitution. ChemCatChem 2, 997-1003 (2010).doi:10.1002/cctc.201000112
45. Benaroudj, N. and Goldberg, A. L. PAN, the proteasome-activating nucleotidase from archaebacteria, is a protein-unfolding molecular chaperone. Nat Cell Biol 2, 833-9 (2000).doi:10.1038/35041081
46. Zolotukhin, S., Potter, M., Zolotukhin, I., Sakai, Y., Loiler, S., Fraites, T. J., Chiodo, V. A., Phillipsberg, T., Muzyczka, N., Hauswirth, W. W., Flotte, T. R., Byrne, B. J. and Snyder, R. O. Production and purification of serotype 1, 2, and 5 recombinant adeno-associated viral vectors. Methods 28, 158-67 (2002).
47. Choi, V. W., Asokan, A., Haberman, R. A. and Samulski, R. J. Production of recombinant adeno-associated viral vectors for in vitro and in vivo use. Curr Protoc Mol Biol Chapter 16, Unit 16.25 (2007).doi:10.1002/0471142727.mb1625s78
48. Lock, M., Alvira, M., Vandenberghe, L. H., Samanta, A., Toelen, J., Debyser, Z. and Wilson, J. M. Rapid, simple, and versatile manufacturing of recombinant adeno-associated viral vectors at scale. Hum Gene Ther 21, 1259-71 (2010).doi:10.1089/hum.2010.055
49. Xiao, X., Li, J. and Samulski, R. J. Production of High-Titer Recombinant Adeno-Associated Virus Vectors in the Absence of Helper Adenovirus. Journal of Virology 72, 2224-2232 (1998).
50. Tremblay, M. E., Riad, M. and Majewska, A. Preparation of mouse brain tissue for immunoelectron microscopy. J Vis Exp (2010).doi:10.3791/2021

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method of targeted delivery of a therapeutic or a diagnostic agent to a subject, comprising:
administering a ligand associated with a therapeutic or a diagnostic agent to a mammalian subject expressing a receptor for the ligand, wherein the receptor is not naturally expressed in the subject, wherein the receptor comprises a cohesin domain of a non-mammalian protein, and wherein the ligand comprises a dockerin domain.

2. The method of claim 1, wherein the receptor comprises an extracellular domain of a non-mammalian protein that contains the cohesin domain.

3. The method of claim 1, wherein the non-mammalian protein is a bacterial protein.

4. The method of claim 1, wherein the receptor comprises at least one of an intracellular, transmembrane and extracellular domain of a mammalian receptor.

5. The method of claim 4, wherein the intracellular, transmembrane or extracellular domain is an intracellular, transmembrane or extracellular domain of a transferrin receptor or a nerve growth factor receptor.

6. The method of claim 1, wherein the therapeutic or diagnostic agent is a therapeutic agent selected from the group consisting of a protein, a peptide, an adeno-associated virus and a small molecule.

7. The method of claim 1, wherein the therapeutic or diagnostic agent is a diagnostic agent selected from the group consisting of an enzyme, a fluorescent compound, a radioactive compound, an ultrasound contrast agent, an optical dye, and a paramagnetic metal atom.

8. The method of claim 1, wherein the therapeutic or diagnostic agent is conjugated or fused to the ligand.

9. The method of claim 1, wherein the therapeutic or diagnostic agent is contained within a nanoparticle.

10. The method of claim 1, wherein the ligand is administered to the subject by intravenous injection.

11. The method of claim 1, wherein the receptor is expressed in the choroid plexus of the subject.

12. The method of claim 11, wherein the subject has a neurodegenerative disease, a lysosomal storage disease, or a brain or central nervous system cancer.

13. The method of claim 1, wherein the subject is a human subject.

14. The method of claim 1, wherein the therapeutic or diagnostic agent is conjugated or fused to the ligand via a linker.

15. The method of claim 1 further comprising administering a nucleic acid that comprises a sequence encoding the receptor that comprises a cohesin domain to the subject prior to administering the ligand associated with the therapeutic or diagnostic agent.

16. The method of claim 15, wherein the nucleic acid is contained within a recombinant adeno-associated virus (rAAV) particle.

17. The method of claim 15, wherein the nucleic acid further comprises a promoter sequence.

18. The method of claim 17, wherein the promoter sequence is a tissue-specific promoter sequence.

19. The method of claim 16, wherein the rAAV particle is of a serotype rAAV1, rAAV4 or rAAV9.

20. The method of claim 12, wherein the subject has a neurodegenerative disease.

* * * * *